United States Patent
Ogawa et al.

(10) Patent No.: US 9,890,146 B2
(45) Date of Patent: Feb. 13, 2018

(54) COMPOUND HAVING SELECTIVE EP2 AGONIST ACTIVITY

(71) Applicant: ONO PHARMACEUTICAL CO., LTD., Osaka (JP)

(72) Inventors: Seiji Ogawa, Osaka (JP); Toshihide Watanabe, Osaka (JP); Isamu Sugimoto, Osaka (JP); Kousuke Tani, Osaka (JP); Kazumi Moriyuki, Osaka (JP); Yoshikazu Goto, Osaka (JP); Shinsaku Yamane, Osaka (JP)

(73) Assignee: ONO PHARMACEUTICAL CO., LTD., Osaka (JP)

(*) Notice: Subject to any disclaimer, the term of this patent is extended or adjusted under 35 U.S.C. 154(b) by 0 days.

(21) Appl. No.: 15/121,882

(22) PCT Filed: Feb. 26, 2015

(86) PCT No.: PCT/JP2015/055523
§ 371 (c)(1),
(2) Date: Aug. 26, 2016

(87) PCT Pub. No.: WO2015/129782
PCT Pub. Date: Sep. 3, 2015

(65) Prior Publication Data
US 2017/0015657 A1 Jan. 19, 2017

(30) Foreign Application Priority Data
Feb. 27, 2014 (JP) .................. 2014-036617

(51) Int. Cl.
C07D 417/12 (2006.01)
C07D 417/04 (2006.01)
C07D 407/04 (2006.01)
A61K 45/06 (2006.01)

(52) U.S. Cl.
CPC ............ *C07D 417/04* (2013.01); *A61K 45/06* (2013.01); *C07D 407/04* (2013.01); *C07D 417/12* (2013.01)

(58) Field of Classification Search
CPC .... A61K 45/06; C07D 417/12; C07D 407/04; C07D 417/04
USPC ....................................................... 514/314
See application file for complete search history.

(56) References Cited

U.S. PATENT DOCUMENTS

| 4,281,113 A | * | 7/1981 | Axen ................. C07C 405/00 549/396 |
| 4,312,810 A | | 1/1982 | Axen et al. |
| 4,490,537 A | * | 12/1984 | Johnson ............ C07C 405/0016 548/252 |
| 4,740,523 A | | 4/1988 | Galambos et al. |
| 5,877,211 A | | 3/1999 | Woodward |
| 2002/0044953 A1 | | 4/2002 | Michelet et al. |
| 2008/0015219 A1 | | 1/2008 | Old et al. |
| 2008/0015231 A1 | | 1/2008 | Old et al. |
| 2008/0119538 A1 | | 5/2008 | Old et al. |
| 2012/0122964 A1 | | 5/2012 | Kambe et al. |
| 2013/0310438 A1 | | 11/2013 | Maruyama et al. |

FOREIGN PATENT DOCUMENTS

| EP | 193260 | * | 9/1986 |
| JP | 55-89261 A | | 7/1980 |
| JP | 61-218588 A | | 9/1986 |
| JP | 2009-541340 A | | 11/2009 |
| JP | 2009-543792 A | | 12/2009 |
| JP | 2009-543794 A | | 12/2009 |
| JP | 2009-543795 A | | 12/2009 |
| JP | 2010-516779 A | | 5/2010 |
| JP | 2010-532379 A | | 10/2010 |

(Continued)

OTHER PUBLICATIONS

Birrell; British Journal of Pharmacology 2011, 164, 1845-1846.*

(Continued)

*Primary Examiner* — Daniel R Carcanague
(74) *Attorney, Agent, or Firm* — Sughrue Mion, PLLC

(57) ABSTRACT

A compound represented by general formula (I) wherein all symbols are as defined in the specification, a salt or N-oxide of the compound, or a solvate or prodrug of the compound or the salt or N-oxide has a selective EP2 agonist activity and is highly safe, and is therefore useful as a drug, especially as a therapeutic agent for EP2 receptor-related diseases including immune diseases, allergic diseases, neuronal death, dysmenorrhea, premature birth, miscarriage, baldness, ocular diseases, erectile dysfunction, arthritis, lung injury, pulmonary fibrosis, pulmonary emphysema, bronchitis, chronic obstructive pulmonary disease, bone diseases, cartilage injury and others.

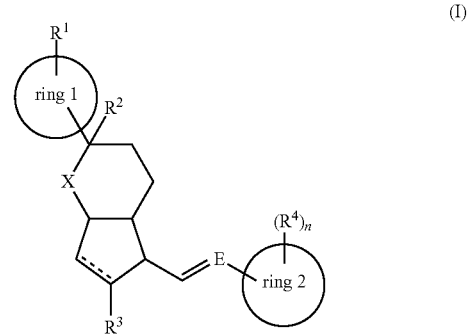

8 Claims, No Drawings

(56) References Cited

FOREIGN PATENT DOCUMENTS

| WO | 2007/149829 A2 | | 12/2007 |
|---|---|---|---|
| WO | 2007/149829 A3 | | 12/2007 |
| WO | 2008/091860 A1 | | 7/2008 |
| WO | 2009/006370 A1 | | 1/2009 |
| WO | 2011/013651 A1 | | 2/2011 |
| WO | WO 2011162562 | * | 12/2011 |
| WO | 2012/102355 A1 | | 8/2012 |
| WO | WO 2017014315 | * | 1/2017 |

OTHER PUBLICATIONS

Prasanna; Experimental Eye Research 2011, 93, 256-264.*
Schachar; Current Eye Research, 2011, 36, 809-817.*
Ogawa; ACS Med. Chem. Lett. 2016, 7, 306-311.*
Ogawa; Bioorganic & Medicinal Chemistry Letters 2016, 26, 2446-2449.*
Ganesh; J. Med. Chem. 2014, 57, 4454-4465.*
International Search Report dated Apr. 14, 2015 issued by International Searching Authority in counterpart International Application No. PCT/JP2015/055523 (PCT/ISA/210).
Written Opinion dated Apr. 14, 2015 issued by International Searching Authority in counterpart International Application No. PCT/JP2015/055523 (PCT/ISA/237).
Nataraj C.et al., "Receptors for prostaglandin $E_2$ that regulate cellular immune responses in the mouse", The Journal of Clinical Investigation, Oct. 2001;108(8):1229-35.
Sheller, J.R. et al., "$EP_2$ receptor mediates bronchodilation by $PGE_2$ in mice", J Appl Physiol., Jun. 2000;88(6):2214-18.
Andrade Da Costa BL et al, "The localization of PGE2 receptor subtypes in rat retinal cultures and the neuroprotective effect of the EP2 agonist butaprost", Neurochem Int. Sep. 2009;55(4):199-207.
Hillock, C. J. et al, "Inhibitory prostanoid EP receptors in human non-pregnant myometrium", European Journal of Pharmacology 378,1999.99-108.
Senior, J. et al, "In vitro characterization of prostanoid EP-receptors in the non-pregnant human myometrium", Br J Pharmacol. Mar. 1991;102(3):747-53.
Woodward,D.F. et al, "Molecular Characterization and Ocular Hypotensive Properties of the Prostanoid EP2 Receptor", J Ocul Pharrnacol Ther. 1995 Fall;11(3):447-54.
Kurihara, Y. et al, "Up-regulation of prostaglandin E receptor EP2 and EP4 subtypes in rat synovial tissues with adjuvant arthritis", Clin Exp Immunol 2001; 123:323-330.
Armstrong, R. A., "Investigation of the inhibitory effects of $PGE_2$ and selective EP agonists on chemotaxis of human neutrophils", Br J Pharmacol. Dec. 1995;116(7):2903-08.
Talpain, E. et al., "Characterization of the PGE receptor subtype mediating inhibition of superoxide production in human neutrophils", Br J Pharmacol. Apr. 1995;114(7):1459-65.
Keerthisingam, C. B. et al, "Cyclooxygenase-2 Deficiency Results in a Loss of the Anti-Proliferative Response to Transforming Growth Factor-β in Human Fibrotic Lung Fibroblasts and Promotes Bleomycin-Induced Pulmonary Fibrosis in Mice", Am J Pathol. Apr. 2001;158(4):1411-22.
Tsuji, T. et al, "Promotion of adipogenesis by an EP2 receptor agonist via stimulation of angiogenesis in pulmonary emphysema", Prostaglandins & Other Lipid Mediators, Aug. 2014;112:9-15.
Sheller, J.R. et al, "$EP_2$ receptor mediates bronchodilation by $PGE_2$ in mice", J Appl Physiol. Jun. 2000;88(6):2214-18.
Fennekohl, A. et al, "Contribution of the two Gs-coupled $PGE_2$-receptors EP2-receptor and EP4-receptor to the inhibition by $PGE_2$ of the LPS-induced TNFα-formation in Kupffer cells from EP2-or EP4-receptor-deficient mice. Pivotal role for the EP4-receptor in wild type Kupffer cells", Journal of Hepatology 36, 3 , Mar. 2002, 328-334.
Hartner, A. et al, "Upregulation of cyclooxygenase-1 and the PGE2 receptor EP2 in rat and human mesangioproliferative glomerulonephritis", Inflamm Res. Jul. 2000,49(7),345-54.
Breyer, M. D. et al, "Prostaglandin E receptors and the kidney", Am J Physiol Renal Physiol. Jul. 2000;279(1):F12-23.
Breyer, M. D. et al, "Functional and Molecular Aspects of Renal Prostaglandin Receptors", J Am Soc Nephrol. Jan. 1996;7(1):8-17.
Kennedy, C. R.J. et al, "Salt-sensitive hypertension and reduced fertility in mice lacking the prostaglandin $EP_2$ receptor", Nat Med Feb. 1999;5(2):217-220.
Németh, K. et al, "Bone marrow stromal cells attenuate sepsis via prostaglandin $E_2$—dependent reprogramming of host macrophages to increase their interleukin-10 production", Nat Med Jan. 2009;15(1):42-49.
Ikegami, R. et al, "The Expression of Prostaglandin E Receptors $EP_2$ and $EP_4$ and Their Different Regulation by Lipopolysaccharide in C3H/HeN Peritoneal Macrophages", J Immunol. Apr. 1, 2001;166(7):4689-96.
Suzawa, T. et al, "The Role of Prostaglandin E Receptor Subtypes (EP1, EP2, EP3, and EP4) in Bone Resorption: An Analysis Using Specific Agonists for the Respective EPs", Endocrinology. Apr. 2000,141(4),1554-59.
Otsuka, S. et al, "PGE2 signal via EP2 receptors evoked by a selective agonist enhances regeneration of injured articular cartilage", Osteoarthritis and Cartilage Apr. 2009;17(4):529-538.

* cited by examiner

COMPOUND HAVING SELECTIVE EP2 AGONIST ACTIVITY

BACKGROUND OF THE INVENTION

Field of the Invention

The present invention relates to a compound represented by general formula (I):

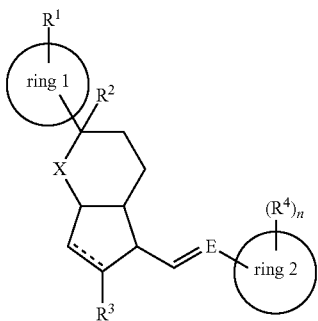

(wherein all symbols are as defined below), a salt or N-oxide of the compound, or a solvate or prodrug of the compound or the salt or N-oxide (hereinbelow, may be sometimes abbreviated as "the compound according to the present invention").

Background of Art

Prostaglandin $E_2$ (hereinbelow, abbreviated as "$PGE_2$") is known as a metabolite in the arachidonate cascade, and is also known to have a cell protection effect, an oxytocic effect, an algogenic effect, an effect of promoting the peristaltic movement of the digestive tract, an awakening effect, a gastric acid secretion inhibiting effect, a blood pressure lowering effect, a diuretic effect and the like.

$PGE_2$ receptors are classified into four subtypes having different roles from one another, i.e., EP1, EP2, EP3, EP4. $PGE_2$ has a wide variety of physiological activities, and therefore has such a problem that, when used as a drug, other undesirable action may be caused besides the intended action. Therefore, it has been attempted to overcome the problem by examining the physiological functions and the expressing sites of the individual subtypes and producing a compound that is effective only on a specific subtype, i.e., a so-called subtype-specific agonist.

For example, an EP2 receptor is considered to be involved in the inhibition of the production of TNF-α and the enhancement of the production of IL-10, and therefore a selective EP2 agonist is considered to be useful for the prevention and/or treatment of immune diseases, allergic diseases, neuronal death, dysmenorrhea, premature birth, miscarriage, baldness, ocular diseases, erectile dysfunction, arthritis, lung injury, pulmonary fibrosis, pulmonary emphysema, bronchitis, chronic obstructive pulmonary disease, liver injury, acute hepatitis, cirrhosis, shock, nephritis, renal failure, cardiovascular diseases, systemic inflammatory response syndrome, sepsis, hemophagocytic syndrome, macrophage activation syndrome, Still's disease, Kawasaki disease, burn injury, systemic granuromatous disease, colitis ulcerosa, Crohn's disease, hypercytokinemia on dialysis, multiple organ failure, bone diseases, cartilage injury and others.

Meanwhile, as compounds which have analogous structures to the structure of the compound according to the present invention, selective FP agonists are disclosed in, for example, International Publication No. 2011/013651 pamphlet (Patent Document 1) and International Publication No. 2012/102355 pamphlet (Patent Document 2), and prostacyclin derivatives are disclosed in, for example, Japanese Patent Laying-Open No. S61-218588 (Patent Document 3) and Japanese Patent Laying-Open No. S55-89261 (Patent Document 4).

However, in these prior art documents, there is found no statement or suggestion about selective EP2 agonists.

PRIOR ART LITERATURE

Patent Document

Patent Document 1: International Publication No. 2011/013651 pamphlet
Patent Document 2: International Publication No. 2012/102355 pamphlet
Patent Document 3: Japanese Patent Laying-Open No. S61-218588
Patent Document 4: Japanese Patent Laying-Open No. S55-89261

SUMMARY OF THE INVENTION

Problems to be Solved by the Invention

An object of the present invention is to provide an excellent selective EP2 agonist in a safe manner.

Means to Solve the Problems

The present inventors have made extensive and intensive studies, and as a result, found that a compound represented by general formula (I) can solve the problems. The present inventors have made further studies, and consequently have completed the present invention.

That is, the present invention relates to:
1. a compound represented by general formula (I):

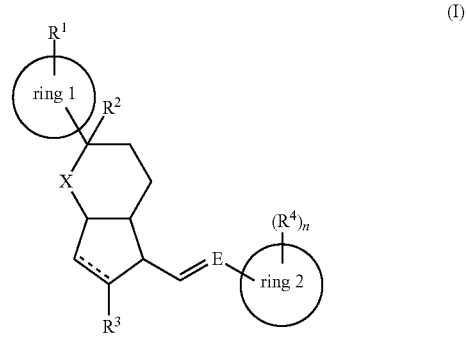

(wherein ring 1 represents a 5- or 6-membered monocyclic aromatic ring;
$R^1$ represents —$(CH_2)_p$—COOH, —$(CH_2)_q$—COOR$^{11}$, —$(CH_2)_r$—OH, —$(CH_2)_s$—OR$^{12}$, —$CH_2NR^{13}R^{14}$ or —$CONR^{13}R^{14}$;
p represents an integer of 0 or 1 to 4;
q represents an integer of 0 or 1 to 4;
r represents an integer of 1 to 4;
s represents an integer of 1 to 4;
$R^{11}$ represents a $C_{1-4}$ alkyl group;
$R^{12}$ represents a $C_{1-4}$ alkyl group or a $C_{1-4}$ acyl group;

$R^{13}$ represents a hydrogen atom or a $C_{1-4}$ alkyl group;

$R^{14}$ represents a hydrogen atom, a $C_{1-4}$ alkyl group, a $C_{1-4}$ acyl group or a $R^{15}O(C=O)$—$C_{1-4}$ alkyl group;

or $R^{13}$ and $R^{14}$ together with a nitrogen atom to which $R^{13}$ and $R^{14}$ are bonded represents a saturated 5 to 8-membered cyclic amine;

$R^{15}$ represents a hydrogen atom or a $C_{1-4}$ alkyl group;

X represents —O—, —S—, —SO—, —SO$_2$—, or —NH—;

$R^2$ represents a hydrogen atom or a $C_{1-4}$ alkyl group;

$R^3$ represents a hydrogen atom or —OR$^{31}$;

$R^{31}$ represents a hydrogen atom, a $C_{1-4}$ alkyl group or a $C_{1-4}$ acyl group;

E represents —O—, —S—, —SO—, —SO$_2$—, —CH$_2$—, =CH— or —NH—;

ring 2 represents a 3 to 15-membered cyclic group;

$R^4$ represents (1) a $C_{1-8}$ alkyl group, (2) a $C_{2-8}$ alkenyl group, (3) a $C_{2-8}$ alkynyl group, (4) a $C_{3-8}$ cycloalkyl group, (5) a $C_{1-8}$ alkoxy group, (6) a $C_{3-8}$ cycloalkyloxy group, (7) a $C_{1-8}$ acyl group, (8) a $C_{1-8}$ acyloxy group, (9) a $C_{1-8}$ alkylthio group, (10) a $C_{3-8}$ cycloalkylthio group, (11) a $C_{1-8}$ alkylsulfinyl group, (12) a $C_{3-8}$ cycloalkylsulfinyl group, (13) a $C_{1-8}$ alkylsulfonyl group, (14) a $C_{3-8}$ cycloalkylsulfonyl group, (15) a $C_{1-8}$ alkoxycarbonyl group, (16) a 5- or 6-membered cyclic group, (17) a (5- or 6-membered cyclic group)-$C_{1-4}$ alkyl group, (18) a (5- or 6-membered cyclic group)-$C_{1-4}$ alkoxy group, (19) a (5- or 6-membered cyclic group)-$C_{1-4}$ acyl group, (20) a halogen atom, (21) a hydroxy group, (22) a nitro group, (23) a cyano group, (24) —NR$^{16}$R$^{17}$, (25) —CONR$^{18}$R$^{19}$ or (26) —SO$_2$NR$^{20}$R$^{21}$;

$R^{16}$ and $R^{17}$ each independently represent a hydrogen atom, a $C_{1-8}$ alkyl group, a $C_{1-8}$ acyl group or a $C_{1-8}$ alkylsulfonyl group;

$R^{18}$, $R^{19}$, $R^{20}$ and $R^{21}$ each independently represent a hydrogen atom or a $C_{1-8}$ alkyl group;

n represents an integer of 0 or 1 to 5, wherein multiple $R^4$'s may be the same as or different from each other when n is 2 or more, and each of groups (1) to (19) among the groups for $R^4$ may be substituted with one to three $R^5$'s;

$R^5$ represents a $C_{1-4}$ alkyl group, a $C_{1-4}$ alkoxy group, a $C_{1-4}$ acyl group, a $C_{3-8}$ cycloalkyl group, —OH, —NR$^{22}$R$^{23}$ or a halogen atom, wherein multiple $R^5$'s may be the same as or different from each other when each of groups (1) to (19) is substituted with the multiple $R^5$'s;

$R^{22}$ and $R^{23}$ each independently represent a hydrogen atom or a $C_{1-4}$ alkyl group;

<u>- - - -</u> represents a single bond or a double bond; and

<img> represents an α-configuration, a β-configuration or a mixture thereof in an arbitrary ratio), a salt or N-oxide of the compound, or a solvate or prodrug of the compound or the salt or N-oxide;

2. the compound according to item 1, wherein E represents —O—, —S—, or —NH—;

3. the compound according to item 1, wherein ring 1 represents a 5-membered monocyclic aromatic heterocyclic ring;

4. the compound according to item 1, wherein X represents —O— or —S—;

5. a compound represented by general formula (I-1):

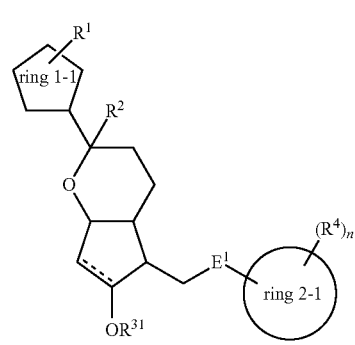

(I-1)

(wherein ring 1-1 represents a 5-membered monocyclic aromatic heterocyclic ring; $E^1$ represents —O—, —S— or —NH—; ring 2-1 represents a benzene ring or a 8- to 15-membered benzene condensed ring which can bind to $E^1$ through a benzene ring; and other symbols are as specified in Claim 1), a salt or N-oxide of the compound, or a solvate or prodrug of the compound or the salt or N-oxide;

6. the compound according to item 5, wherein ring 1-1 represents oxazole, thiazole, furan or thiophene;

7. a pharmaceutical composition comprising a compound represented by general formula (I) or general formula (I-1), a salt or N-oxide of the compound, or a solvate or prodrug of the compound or the salt or N-oxide;

8. a therapeutic and/or prophylactic agent for an EP2 receptor-related disease, the agent comprising a compound represented by general formula (I) or general formula (I-1), a salt or N-oxide of the compound, or a solvate or prodrug of the compound or the salt or N-oxide;

9. use of a compound represented by general formula (I) or general formula (I-1), a salt or N-oxide of the compound, or a solvate or prodrug of the compound or the salt or N-oxide for the production of a therapeutic and/or prophylactic agent for an EP2 receptor-related disease;

10. a compound represented by general formula (I) or general formula (I-1), a salt or N-oxide of the compound, or a solvate or prodrug of the compound or the salt or N-oxide for the production of a therapeutic and/or prophylactic agent for an EP2 receptor-related disease;

11. a compound represented by general formula (I) or general formula (I-1), a salt or N-oxide of the compound, or a solvate or prodrug of the compound or the salt or N-oxide for use in the treatment and/or prevention of an EP2 receptor-related disease;

12. a compound represented by general formula (I) or general formula (I-1), a salt or N-oxide of the compound, or a solvate or prodrug of the compound or the salt or N-oxide for treating and/or preventing an EP2 receptor-related disease; and 13. a method for treating and/or preventing an EP2 receptor-related disease, the method comprising administering an effective amount of a compound represented by general formula (I) or general formula (I-1), a salt or N-oxide of the compound, or a solvate or prodrug of the compound or the salt or N-oxide to a mammal; and the like.

Effect of the Invention

The compound according to the present invention has a selective EP2 agonist activity, and is therefore useful as a therapeutic agent for EP2 receptor-related diseases, including immune diseases (e.g., autoimmune diseases such as amyotrophic lateral sclerosis, multiple sclerosis, Sjogren's syndrome, chronic rheumatoid arthritis and systemic lupus erythematosus; a rejection after organ transplantation, etc.), allergic diseases (e.g., bronchial asthma, allergic rhinitis, allergic conjunctivitis, atopic dermatitis, food allergy, etc.), neuronal death, dysmenorrhea, premature birth, miscarriage, baldness, ocular diseases (e.g., glaucoma, ocular hypertension, macular edema, macular degeneration, retina and optic nerve tensile force rise, myopia, hypermetropia, astigmatism, dry eye, retinal detachment, cataract, intraocular pressure rise, etc.), erectile dysfunction, arthritis, lung injury, pulmonary fibrosis, pulmonary emphysema, bronchitis, chronic obstructive pulmonary disease, liver injury, acute hepatitis, cirrhosis, shock, nephritis (e.g., acute nephritis, chronic nephritis, etc.), renal failure, cardiovascular diseases (e.g., hypertension, myocardial ischemia, chronic arterial occlusive disease, vibration disease, etc.), systemic inflammatory response syndrome, sepsis, hemophagocytic syndrome, macrophage activation syndrome, Still's disease, Kawasaki disease, burn injury, systemic granuromatous disease, colitis ulcerosa, Crohn's disease, hypercytokinemia on dialysis, multiple organ failure, bone diseases (e.g., bone fracture, bone refracture, intractable bone fracture, bone nonunion, pseudarthrosis, osteomalacia, bone Paget's disease, ankylosing spondylitis, cancer bone metastasis, arthrosis deformans, and bone destruction in analogous diseases thereto, etc.), cartilage injury and others.

DETAILED DESCRIPTION OF PREFERRED EMBODIMENTS

The present invention relates to: a compound represented by general formula (I):

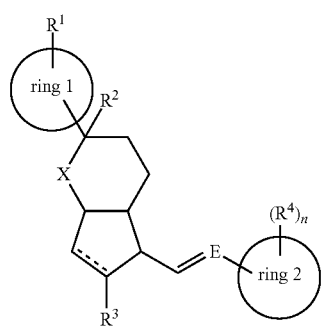

(wherein ring 1 represents a 5- or 6-membered monocyclic aromatic ring;
$R^1$ represents —$(CH_2)_p$—COOH, —$(CH_2)_q$—COOR$^{11}$, —$(CH_2)_r$—OH, —$(CH_2)_s$—OR$^{12}$, —$CH_2NR^{13}R^{14}$ or —CONR$^{13}R^{14}$;
p represents an integer of 0 or 1 to 4;
q represents an integer of 0 or 1 to 4;
r represents an integer of 1 to 4;
s represents an integer of 1 to 4;
$R^{11}$ represents a $C_{1-4}$ alkyl group;
$R^{12}$ represents a $C_{1-4}$ alkyl group or a $C_{1-4}$ acyl group;
$R^{13}$ represents a hydrogen atom or a $C_{1-4}$ alkyl group;
$R^{14}$ represents a hydrogen atom, a $C_{1-4}$ alkyl group, a $C_{1-4}$ acyl group or a
$R^{15}O(C=O)$—$C_{1-4}$ alkyl group;

or $R^{13}$ and $R^{14}$ together with a nitrogen atom to which $R^{13}$ and $R^{14}$ are bonded represents a saturated 5 to 8-membered cyclic amine;
$R^{15}$ represents a hydrogen atom or a $C_{1-4}$ alkyl group;
X represents —O—, —S—, —SO—, —$SO_2$—, or —NH—;
$R^2$ represents a hydrogen atom or a $C_{1-4}$ alkyl group;
$R^3$ represents a hydrogen atom or —$OR^{31}$;
$R^{31}$ represents a hydrogen atom, a $C_{1-4}$ alkyl group or a $C_{1-4}$ acyl group;
E represents —O—, —S—, —SO—, —$SO_2$—, —$CH_2$—, =CH— or —NH—;
ring 2 represents a 3 to 15-membered cyclic group;
$R^4$ represents (1) a $C_{1-8}$ alkyl group, (2) a $C_{2-8}$ alkenyl group, (3) a $C_{2-8}$ alkynyl group, (4) a $C_{3-8}$ cycloalkyl group, (5) a $C_{1-8}$ alkoxy group, (6) a $C_{3-8}$ cycloalkyloxy group, (7) a $C_{1-8}$ acyl group, (8) a $C_{1-8}$ acyloxy group, (9) a $C_{1-8}$ alkylthio group, (10) a $C_{3-8}$ cycloalkylthio group, (11) a $C_{1-8}$ alkylsulfinyl group, (12) a $C_{3-8}$ cycloalkylsulfinyl group, (13) a $C_{1-8}$ alkylsulfonyl group, (14) a $C_{3-8}$ cycloalkylsulfonyl group, (15) a $C_{1-8}$ alkoxycarbonyl group, (16) a 5- or 6-membered cyclic group, (17) a (5- or 6-membered cyclic group)-$C_{1-4}$ alkyl group, (18) a (5- or 6-membered cyclic group)-$C_{1-4}$ alkoxy group, (19) a (5- or 6-membered cyclic group)-$C_{1-4}$ acyl group, (20) a halogen atom, (21) a hydroxy group, (22) a nitro group, (23) a cyano group, (24) —$NR^{16}R^{17}$, (25) —$CONR^{18}R^{19}$ or (26) —$SO_2NR^{20}R^{21}$;
$R^{16}$ and $R^{17}$ each independently represent a hydrogen atom, a $C_{1-8}$ alkyl group, a $C_{1-8}$ acyl group or a $C_{1-8}$ alkylsulfonyl group;
$R^{18}$, $R^{19}$, $R^{20}$ and $R^{21}$ each independently represent a hydrogen atom or a $C_{1-8}$ alkyl group;
n represents an integer of 0 or 1 to 5, wherein multiple $R^4$'s may be the same as or different from each other when n is 2 or more, and each of groups (1) to (19) among the groups for $R^4$ may be substituted with one to three $R^5$'s;
$R^5$ represents a $C_{1-4}$ alkyl group, a $C_{1-4}$ alkoxy group, a $C_{1-4}$ acyl group, a $C_{3-8}$ cycloalkyl group, —OH, —$NR^{22}R^{23}$ or a halogen atom, wherein multiple $R^5$'s may be the same as or different from each other when each of groups (1) to (19) is substituted with the multiple $R^5$'s;
$R^{22}$ and $R^{23}$ each independently represent a hydrogen atom or a $C_{1-4}$ alkyl group;

~~~~ represents a single bond or a double bond; and represents an α-configuration, a β-configuration or a mixture thereof in an arbitrary ratio),
a salt or N-oxide of the compound, or a solvate or prodrug of the compound or the salt or N-oxide (which may be sometimes collectively called "the compound according to the present invention", hereinbelow); a pharmaceutical composition comprising the compound according to the present invention; and a prophylactic and/or therapeutic agent for an EP2 receptor-related disease, the agent comprising the compound according to the present invention.

In the specification, the 5- or 6-membered monocyclic aromatic ring indicates a benzene ring and a 5- or 6-membered monocyclic aromatic heterocyclic ring. Examples of the 5-membered monocyclic aromatic heterocyclic ring include pyrrole, imidazole, triazole, tetrazole, pyrazole, furan, thiophene, oxazole, isoxazole, thiazole, isothiazole, furazan, oxadiazole and thiadiazole ring, etc. Examples of the 6-membered monocyclic aromatic heterocyclic ring include pyridine, pyrazine, pyrimidine and pyridazine ring, etc.

In the specification, the $C_{1-4}$ alkyl group includes a methyl group, an ethyl group, a propyl group, a butyl group and isomers thereof.

In the specification, the $C_{1-4}$ alkoxy group includes a methoxy group, an ethoxy group, a propoxy group, a butoxy group and isomers thereof.

In the specification, the $C_{1-4}$ acyl group includes a methanoyl group, an ethanoyl group, a propanoyl group, a butanoyl group and isomers thereof.

In the specification, examples of the saturated 5- to 8-membered cyclic amine include pyrrolidine, imidazolidine, triazolidine, tetrazolidine, pyrazolidine, piperidine, piperazine, perhydropyrimidine, perhydropyridazine, perhydroazepine, perhydrodiazepine, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, perhydrothiazepine, perhydrothiadiazepine, morpholine and thiomorpholine, etc.

In the specification, the $C_{1-8}$ alkyl group includes a methyl group, an ethyl group, a propyl group, a butyl group, a pentyl group, a hexyl group, a heptyl group, an octyl group and isomers thereof.

In the specification, the $C_{2-8}$ alkenyl group refers to, for example, a $C_{2-8}$ alkenyl group having 1 to 2 double bonds, and specifically includes an ethenyl group, a propenyl group, a butenyl group, a butadienyl group, a pentenyl group, a pentadienyl group, a hexenyl group, a hexadienyl group, a heptenyl group, a heptadienyl group, an octenyl group, an octadienyl group and isomers thereof.

In the specification, the $C_{2-8}$ alkynyl group refers to, for example, a $C_{2-8}$ alkynyl group having 1 to 2 triple bonds, and specifically includes an ethynyl group, a propynyl group, a butynyl group, a butadiynyl group, a pentynyl group, a pentadiynyl group, a hexynyl group, a hexadiynyl group, a heptynyl group, a heptadiynyl group, an octynyl group, an octadiynyl group and isomers thereof.

In the specification, the $C_{3-8}$ cycloalkyl group includes a cyclopropyl group, a cyclobutyl group, a cyclopentyl group, a cyclohexyl group, a cycloheptyl group and a cyclooctyl group.

In the specification, the $C_{1-8}$ alkoxy group includes a methoxy group, an ethoxy group, a propoxy group, a butoxy group, a pentyloxy group, a hexyloxy group, a heptyloxy group, an octyloxy group and isomers thereof.

In the specification, the $C_{3-8}$ cycloalkyloxy group includes a cyclopropyloxy group, a cyclobutyloxy group, a cyclopentyloxy group, a cyclohexyloxy group, a cycloheptyloxy group and a cyclooctyloxy group.

In the specification, the $C_{1-8}$ acyl group includes a methanoyl group, an ethanoyl group, a propanoyl group, a butanoyl group, a pentanoyl group, a hexanoyl group, a heptanoyl group, an octanoyl group and isomers thereof.

In the specification, the $C_{1-8}$ acyloxy group includes a methanoyloxy group, an ethanoyloxy group, a propanoyloxy group, a butanoyloxy group, a pentanoyloxy group, a hexanoyloxy group, a heptanoyloxy group, an octanoyloxy group and isomers thereof.

In the specification, the $C_{1-8}$ alkylthio group includes a methylthio group, an ethylthio group, a propylthio group, a butylthio group, a pentylthio group, a hexylthio group, a heptylthio group, an octylthio group and isomers thereof.

In the specification, the $C_{3-8}$ cycloalkylthio group includes a cyclopropylthio group, a cyclobutylthio group, a cyclopentylthio group, a cyclohexylthio group, a cycloheptylthio group and a cyclooctylthio group.

In the specification, the $C_{1-8}$ alkylsulfinyl group includes a methylsulfinyl group, an ethylsulfinyl group, a propylsulfinyl group, a butylsulfinyl group, a pentylsulfinyl group, a hexylsulfinyl group, a heptylsulfinyl group, an octylsulfinyl group and isomers thereof.

In the specification, the $C_{3-8}$ cycloalkylsulfinyl group includes a cyclopropylsulfinyl group, a cyclobutylsulfinyl group, a cyclopentylsulfinyl group, a cyclohexylsulfinyl group, a cycloheptylsulfinyl group and a cyclooctylsulfinyl group.

In the specification, the $C_{1-8}$ alkylsulfonyl group includes a methylsulfonyl group, an ethylsulfonyl group, a propylsulfonyl group, a butylsulfonyl group, a pentylsulfonyl group, a hexylsulfonyl group, a heptylsulfonyl group, an octylsulfonyl group and isomers thereof.

In the specification, the $C_{3-8}$ cycloalkylsulfonyl group includes a cyclopropylsulfonyl group, a cyclobutylsulfonyl group, a cyclopentylsulfonyl group, a cyclohexylsulfonyl group, a cycloheptylsulfonyl group and a cyclooctylsulfonyl group.

In the specification, the $C_{1-8}$ alkoxycarbonyl group includes a methoxycarbonyl group, an ethoxycarbonyl group, a propoxycarbonyl group, a butoxycarbonyl group, a pentyloxycarbonyl group, a hexyloxycarbonyl group, a heptyloxycarbonyl group, an octyloxycarbonyl group and isomers thereof.

In the specification, the 5- or 6-membered cyclic group indicates a 5- or 6-membered carbon ring and a 5- or 6-membered heterocyclic ring.

Examples of the 5- or 6-membered carbon ring include cyclopentane, cyclohexane, cyclopentene, cyclohexene, cyclopentadiene, cyclohexadiene and benzene, etc.

Examples of the 5- or 6-membered heterocyclic ring include pyrrole, imidazole, triazole, tetrazole, pyrazole, pyridine, pyrazine, pyrimidine, pyridazine, furan, pyran, thiophene, thiopyran, oxazole, isoxazole, thiazole, isothiazole, furazan, oxadiazole, oxazine, oxadiazine, thiadiazole, thiazine, thiadiazine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrofuran, tetrahydrofuran, dihydropyran, tetrahydropyran, dihydrothiophene, tetrahydrothiophene, dihydrothiopyran, tetrahydrothiopyran, dihydrooxazole, tetrahydrooxazole (oxazolidine), dihydroisoxazole, tetrahydroisoxazole (isoxazolidin dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrothiadiazole, tetrahydrothiadiazole (thiadiazolidine), dihydrothiazine, tetrahydrothiazine, dihydrothiadiazine, tetrahydrothiadiazine, morpholine, thiomorpholine, oxathiane, dioxolane, dioxane, dithiolane and dithiane, etc.

In the specification, the 3- to 15-membered cyclic group indicates a 3- to 15-membered carbon ring and a 3- to 15-membered heterocyclic ring.

Examples of the 3- to 15-membered carbon ring include cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, tetrahydronaphthalene, perhydronaphthalene, heptalene, perhydroheptalene, biphenylene, as-indacene, s-indacene, acenaphthylene, acenaphthene, fluorene, phenalene, phenanthrene, anthracene, spiro[4.4]nonane, spiro[4,5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, bicyclo[4.2.0]octa-1,3,5-triene, 2,3-dihydro-1H-indene, 1,2,3,4-tetrahydronaphthalene, 6,7,8,9-tetrahydro-5H-benzo[7]annulene, 5,6,7,8,9,10-hexahydrobenzo[8]annulene, 2',3'-dihydrospirocyclopropane-1,1'-indene, 3',4'-dihydro-2'H-spirocyclopropane-1,1'-naphthalene, adamantane, noradamantane and Cubane ring, etc.

Examples of the 3- to 15-membered heterocyclic ring include pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, bertzofurazan, benzothiadiazole, benzotriazole, carbazole, beta-carbolin, acridine, phenazine, dibenzofuran, xanthene, dibenzothiophene, phenothiazine, phenoxazine, phenoxathiin, thianthrene, phenanthridine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chroman, benzodithiolane, benzodithiane, azaspiro[4.4]nonane, oxazaspiro[4.4]nonane, dioxaspiro[4.4]nonane, azaspiro[4.5]decane, thiaspiro[4.5]decane, dithiaspiro[4.5]decane, dioxaspiro[4.5]decane, oxazaspiro[4.5]decane, azaspiro[5.5]undecane, oxaspiro[5.5]undecane, dioxaspiro[5.5]undecane, azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane and diazabicyclo[2.2.2]octane ring, etc.

In the specification, the halogen atom includes a fluorine atom, a bromine atom, a chlorine atom and an iodine atom.

In the specification, represents a single bond or a double bond, represents that a group is bonded to another side of a paper plane (i.e., an α-configuration).

represents that a group is bonded to a front side of a paper plane (i.e., in a β-configuration), and represents an α-configuration, a β-configuration or a mixture thereof in an arbitrary ratio.

Preferred embodiments of the compound represented by general formula (I) include a compound represented by general formula (I-1):

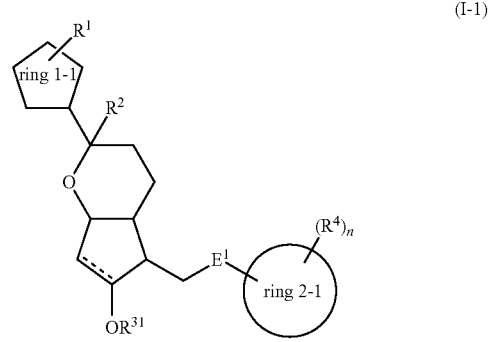

(wherein ring 1-1 represents a 5-membered monocyclic aromatic heterocyclic ring; $E^1$ represents —O—, —S—, or —NH—; film 2-1 represents a benzene ring or a 8- to 15-membered benzene condensed ring which can bond to $E^1$ through the benzene ring; and other symbols are as defined above), and a compound represented by general formula (I-2):

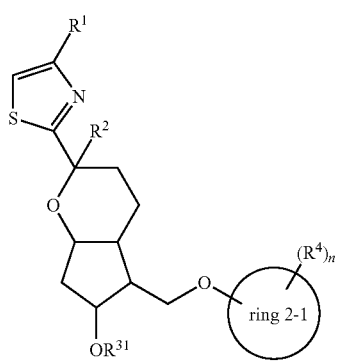

(I-2)

(wherein all symbols are as defined above).

In general formula (I), ring 1 is preferably a 5-membered monocyclic aromatic heterocyclic ring, more preferably an oxazole ring, a thiazole ring, a furan ring or a thiophene ring.

In general formula (I-1), ring 1-1 is preferably an oxazole ring, a thiazole ring, a furan ring or a thiophene ring.

In all of general formula (I), general formula (I-1) and general formula (I-2), p is preferably 0.

In all of general formula (I), general formula (I-1) and general formula (I-2), q is preferably 0.

In all of general formula (I), general formula (I-1) and general formula (I-2), r is preferably 1.

In all of general formula (I), general formula (I-1) and general formula (I-2), s is preferably 1.

In all of general formula (I), general formula (I-1) and general formula (I-2), $R^1$ is preferably —$(CH_2)_p$—COOH, —$(CH_2)_q$—COOR$^{11}$, —$(CH_2)_r$—OH or —$(CH_2)_s$—OR$^{12}$, particularly preferably —COOH, —COOR$^{11}$, —$CH_2$OH or —$CH_2$OR$^{12}$, and $R^{11}$ is preferably an isopropyl group.

In all of general formula (I), general formula (I-1) and general formula (I-2), $R^2$ is preferably a hydrogen atom or a methyl group.

In general formula (I), $R^3$ is preferably —OR$^{31}$.

In general formula (I), E is preferably —O—, —S— or —NH—, more preferably —O— or —S—.

In general formula (I-1), $E^1$ is preferably —O—.

In general formula (I), ring 2 is preferably a benzene ring or an 8- to 15-membered benzene condensed ring. Examples of the 8- to 15-membered benzene condensed ring include indene, indan, naphthalene, dihydronaphthalene, teterahydronaphthalene, biphenylene, acenaphthylene, acenaphthene, fluorene, phenalene, phenanthrene, anthracene, bicyclo[4.2.0]octa-1,3,5-triene, 2,3-dihydro-1H-indene, 1,2,3,4-tetrahydronaphthalene, 6,7,8,9-tetrahydro-5H-benzo[7]annulene, 5,6,7,8,9,10-hexahydrobenzo[8]annulene, 2',3'-dihydrospirocyclopropane-1,1'-indene, 3',4'-dihydro-2'H-spirocyclopropane-1,1'-naphthalene, indole, benzofuran, benzothiophene, dithianaphthalene, indazole, quinolone, isoquinoline, phthalazine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine, indoline, isoindoline, dihydrobenzofuran, dihydroisobenzofuran, dihydrobenzothiophene, dihydroisobenzothiophene, dihydroindazole, dihydroquinoline, tetrahydroquinoline, dihydroisoquinoline, tetrahydroisoquinoline, dihydrophthalazine, tetrahydrophthalazine, dihydroquinoxaline, tetrahydroquinoxaline, dihydroquinazoline, tetrahydroquinazoline, dihydrocinnoline, tetrahydrocinnoline, benzoxathiane, dihydrobenzoxazine, dihydrobenzothiazine, dihydrobenzoxazole, dihydrobenzothiazole, dihydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, dihydroacridine, tetrahydroacridine, dihydrodibenzofuran, dihydrodibenzothiophene, tetrahydrodibenzofuran, tetrahydrodibenzothiophene, dioxaindan, benzodioxane, chroman, benzodithiolane and benzodithiane ring, etc.

Ring 2 is more preferably a benzene ring or an 8- to 15-membered benzene condensed ring below such as indene, indan, naphthalene, dihydronaphthalene, teterahydronaphthalene, bicyclo[4.2.0]octa-1,3,5-triene, 2,3-dihydro-1H-indene, 1,2,3,4-tetrahydronaphthalene, 6,7,8,9-tetrahydro-5H-benzo[7]annulene, 5,6,7,8,9,10-hexahydrobenzo[8]annulene, 2',3'-dihydrospirocyclopropane-1,1'-indene, 3',4'-dihydro-2'H-spirocyclopropane-1,1'-naphthalene, indole, benzofuran, benzothiophene, indazole, quinolone, isoquinoline, phthalazine, quinoxaline, quinazoline, cinnoline, benzoxazole, benzothiazole, benzimidazole, chromene, indoline, isoindoline, dihydrobenzofuran, dihydroisobenzofuran, dihydrobenzothiophene, dihydroisobenzothiophene, dihydroindazole, dihydroquinoline, tetrahydroquinoline, dihydroisoquinoline, tetrahydroisoquinoline, dihydrophthalazine, tetrahydrophthalazine, dihydroquinoxaline, tetrahydroquinoxaline, dihydroquinazoline, tetrahydroquinazoline, dihydrocinnoline, tetrahydrocinnoline, dihydrobenzoxazine, dihydrobenzothiazine, dihydrobenzoxazole, dihydrobenzothiazole, dihydrobenzimidazole or chroman ring, etc.

When ring 2 is the 8- to 15-membered benzene condensed ring, it is preferred that the benzene ring moiety in ring 2 is bonded to E in general formula (I).

Particularly preferred examples of ring 2 include the following rings:

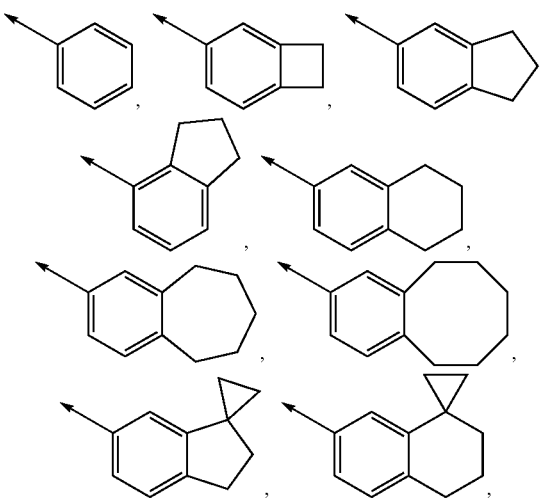

-continued

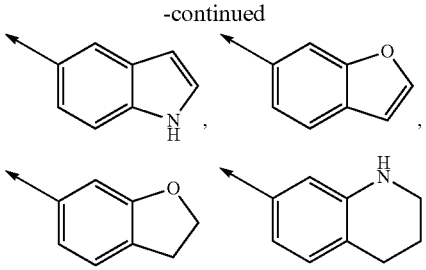

(wherein an arrow represents a bonding site for E).

In both of general formula (I-1) and general formula (I-2), ring 2-1 is preferably a benzene ring or any one of the rings that are mentioned as preferred examples of the 8- to 15-membered benzene condensed ring.

In general formula (I-1), particularly preferred examples of ring 2-1 include the following rings:

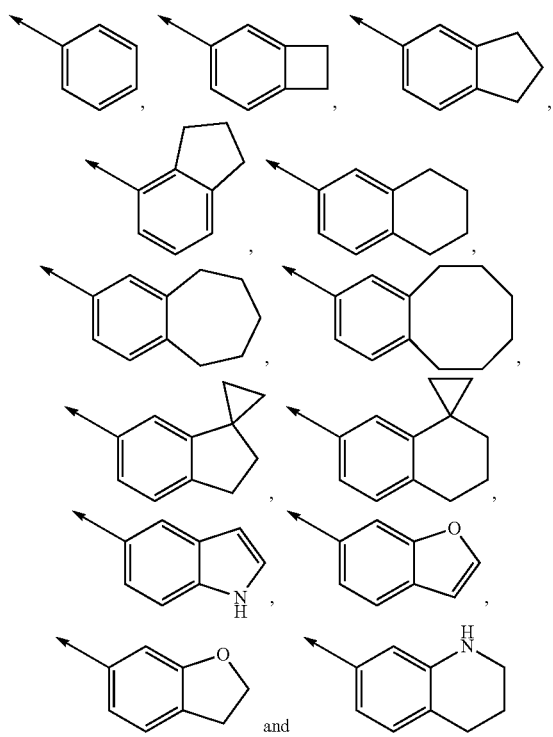

(wherein an arrow represents a bonding site for $E^1$).

In general formula (I-2), particularly preferred examples of ring 2-1 include the following rings:

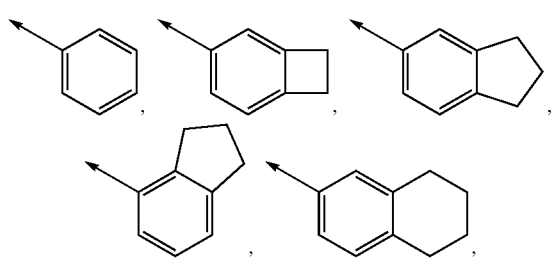

-continued

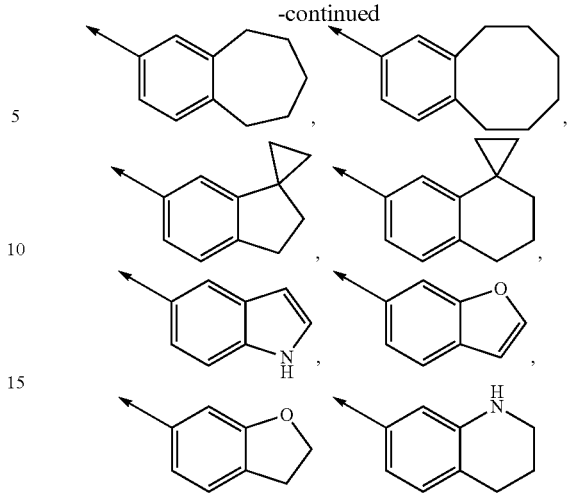

(wherein an arrow represents a bonding site for —O—).

In general formula (I), general formula (I-1) and general formula (I-2), ring 2 or ring 2-1 may be unsubstituted or may be substituted by n pieces, i.e., one to five $R^4$'s. When the ring is substituted with multiple $R^4$s, that is, n is 2 or more, the multiple $R^4$'s may substitute for a single atom that constitutes ring 2 or ring 2-1 or may substitute for different atoms. When the ring is substituted with multiple $R^4$s, the $R^4$'s may be the same as or different from each other.

In all of general formula (I), general formula (I-1) and general formula (I-2), $R^4$ is preferably any one of the above-mentioned substituents (1) to (26), more preferably (1) a $C_{1-8}$ alkyl group, (2) a $C_{2-8}$ alkenyl group, (3) a $C_{2-8}$ alkynyl group, (4) a $C_{3-8}$ cycloalkyl group, (5) a $C_{1-8}$ alkoxy group, (6) a $C_{3-8}$ cycloalkyloxy group, (7) a $C_{1-8}$ acyl group, (9) a $C_{1-8}$ alkylthio group, (20) a halogen atom, (21) a hydroxy group, (22) a nitro group, (23) a cyano group or (24) —$NR^{16}R^{17}$.

In all of general formula (I), general formula (I-1) and general formula (I-2), n is preferably an integer of 0 or 1 to 3.

In general formula (I), general formula (I-1) and general formula (I-2), $R^4$ may be substituted with one to three $R^5$'s.

When $R^4$ is substituted with multiple $R^5$'s, $R^5$'s may be the same as or different from each other.

The compound represented by general formula (I) is preferably such a compound that some or all of the above-mentioned preferred examples for ring 1, $R^1$, $R^2$, $R^3$, E, ring 2, $R^4$ and n are combined.

The compound represented by general formula (I-1) is preferably such a compound that some or all of the above-mentioned preferred ring 1-1, $R^1$, $R^2$, $E^1$, ring 2-1, $R^4$ and n are combined.

The compound represented by general formula (I-2) is preferably such a compound that some or all of the above-mentioned preferred $R^1$, ring 2-1, $R^4$ and n are combined.

In addition, all of compounds mentioned in section "Examples" are preferred.

[Isomer]

In the present invention, an isomer includes all isomers unless otherwise is indicated. For example, an alkyl group, an alkoxy group, an alkylene group and the like include those of linear forms and branched forms. In addition, all of an isomer at a double bond, a ring, or a condensed ring (E isomer, Z isomer, cis isomer, trans isomer), an isomer due to the presence of an asymmetric carbon etc. (R, S isomer, α-configuration, β-configuration, enantiomer, diastereomer), an optically active body having optical rotation (D, L, d, l isomer), a polar body derived from chromatographic separation (high polar compound, low polar compound), an equilibrated compound, a rotation isomer, a mixture of them at an arbitrary ratio, and a racemic mixture are included in the present invention. In addition, in the present invention, the isomer includes all isomers derived from tautomers.

Examples of the isomer of the compound represented by general formula (I) which occurs due to the presence of an asymmetric carbon include, but are not limited to, the following compounds:

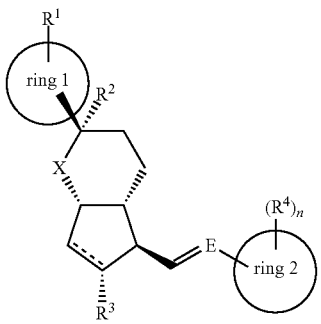

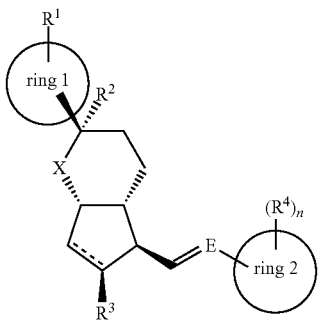

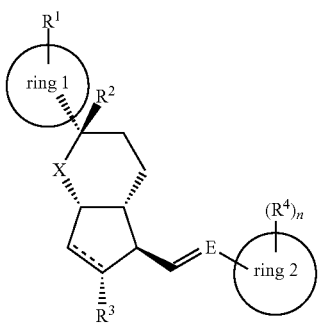

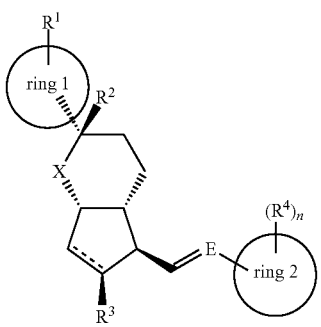

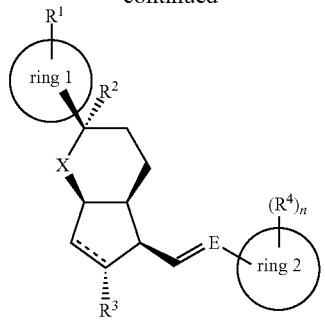

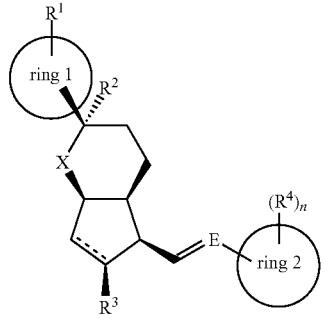

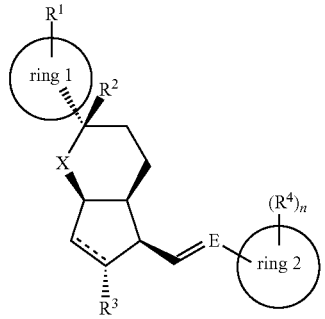

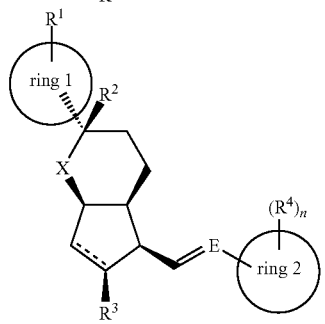

(wherein all symbols are as defined above).

[Salt, N-Oxide, Solvate]

A salt of the compound represented by general formula (I) which is disclosed in the present invention include all of pharmacologically acceptable salts of the compound. The pharmacologically acceptable salt is preferably one which has low toxicity and is soluble in water. Examples of the proper salt include salts with an alkali metal (e.g., potassium, sodium, lithium, etc.), salts with an alkaline earth metal (e.g., calcium, magnesium, etc.), ammonium salts (e.g., a tetramethylammonium salt, a tetrabutylammonium salt, etc.), salts with an organic amine (e.g., alkylamines [e.g., methylamine, dimethylamine, trimethylamine, triethylamine, etc.], heterocyclic amines [e.g., pyridine, picoline, piperidine, etc.], alkanolamines [e.g., monoethanolamine, diethanolamine, triethanolamine, etc.], cyclopentylamine, cyclohexylamine, dicyclohexylamine, benzylamine, dibenzylamine, phenethylamine, N,N'-dibenzylethylenediamine, tris(hydroxymethyl)methylamine, N-methyl-D-glucamine, basic naturally-occurring amino acids [e.g., arginine, lysine, ornithine, histidine, etc.], and acid addition salts (e.g., inorganic acid salts [e.g., hydrochloride, hydrobromide, hydroiodide, sulfate, phosphate, nitrate etc.]), organic acid salts [e.g., acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate etc.], salts with an acidic naturally-occurring amino acid [e.g., aspartate, glutamate], etc.).

In addition, the salt also includes a quaternary ammonium salt. A quaternary ammonium salt is a compound produced by quaternizing a nitrogen atom in the compound represented by general formula (I) with a $R^o$ group. Here, the $R^o$ group includes a $C_{1-8}$ alkyl group which may be substituted with a phenyl group, and the like.

An N-oxide of the compound represented by general formula (I) is a compound produced by oxidizing a nitrogen atom in the compound represented by general formula (I). The N-oxide may be in the form of a salt, such as the salt with an alkali metal, the salt with an alkaline earth metal, the ammonium salt, the salt with an organic amine and the acid addition salt, all are as mentioned above.

The compound represented by general formula (I) or the salt or N-oxide thereof may be in the form of a solvate with water, an alcohol-based solvent (e.g., ethanol) or the like. It is preferred that the solvate has low toxicity and is soluble in water.

The compound represented by general formula (I) can be converted into a salt, an N-oxide or a solvate as mentioned above by a known method.

[Prodrug]

A prodrug of the compound represented by general formula (I) refers to a compound which is converted into the compound represented by general formula (I) by a reaction with an enzyme or gastric acid in a living body. Examples of the prodrug of the compound represented by general formula (I) include as follows: when the compound represented by general formula (I) has a carboxy group, compounds in which the carboxy group is esterified or amidated (e.g., compounds in which a carboxyl group of the compound represented by general formula (I) is methyl-esterified, ethyl-esterified, isopropyl-esterified, phenyl-esterified, carboxymethyl-esterified, dimethylaminomethyl-esterified, pivaloyloxymethyl-esterified, phthalidyl-esterified, 1-{(ethoxycarbonyl)oxy)}ethyl-esterified, (5-methyl-2-oxo-1,3-dioxolen-4-yl)methyl-esterified, 1-{[(cyclohexyloxy)carbonyl]oxy}ethyl-esterified or methyl-amidated, etc.), or the like; when the compound represented by general formula (I) has a hydroxy group, compounds in which the hydroxy group is acylated, alkylated, phosphorylated or borated (e.g., compounds in which a hydroxy group of the compound represented by general formula (I) is acetylated, palmitoylated, propanoylated, pivaloylated, succinylated, fumarylated, alanylated or dimethylaminomethyl-carbonylated, etc.), or the like; and, when the compound represented by general formula (I) has an amino group, compounds in which the amino group is acylated, alkylated or phosphorylated (e.g., compounds in which an amino group of the compound represented by general formula (I) is eicosanoylated, alanylated, pentylamino-carbonylated, (5-methyl-2-oxo-1,3-dioxolen-4-yl)-methoxycarbonylated, tetrahydrofuranylated, pyrrolidylmethylated, pivaloyloxymethylated, acetoxymethylated or tert-butylated, etc.), or the like. The prodrug of the compound represented by general formula (I) may be a prodrug which is changed to the compound represented by general formula (I) under the physiological condition, as described in "Development of Medicaments" published by Hirokawa Shoten Co., Ltd., vol. 7, "Molecular Design", p. 163-198 (1990). The prodrug of the compound represented by general formula (I) can be produced by a method known per se. The prodrug of the compound represented by general formula (I) may be in the form of a salt, such as the salt with an alkali metal, the salt with an alkaline earth metal, the ammonium salt, the salt with an organic amine and the acid addition salt, all are as mentioned above, and may be also in the form of a solvate with water or an alcohol-based solvent (e.g., ethanol, etc.) or so on, likewise the compound represented by general formula (I).

[Labeled Compound]

The compound according to the present invention includes a so-called "labeled compound", i.e., a compound in which some or all of atoms that constitute the present compound are each substituted with its isotopic element. The labeled compound can be produced by a method known per se. Preferred examples of the isotopic element to be used for labeling include, but are not limited to, $^2H$, $^3H$, $^{13}C$, $^{14}C$, $^{15}N$, $^{16}N$, $^{17}O$, $^{18}O$, $^{35}S$, $^{36}Cl$, $^{77}Br$ and $125I$.

[Method for Producing Compound According to Present Invention]

The compound according to the present invention can be produced by properly improving a known method, for example, the method described in "Comprehensive Organic Transformations: A Guide to Functional Group Preparations, 2nd Edition (Richard C. Larock, John Wiley & Sons Inc., 1999)", the method described in the section "Examples" or the like and employing a combination of the methods.

The compound represented by general formula (I) can also be produced by the below-mentioned method.

Among the compounds represented by general formula (I), a compound in which E is —O—, i.e., a compound represented by general formula (Ia):

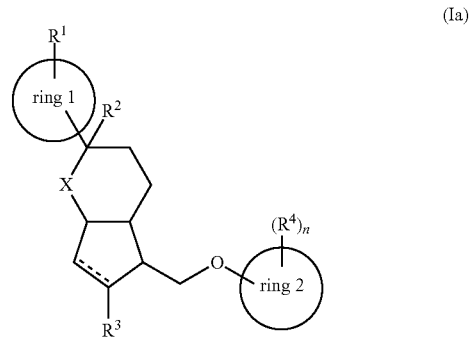

(Ia)

(wherein all symbols are as defined above) can be produced by subjecting a compound represented by general formula (II):

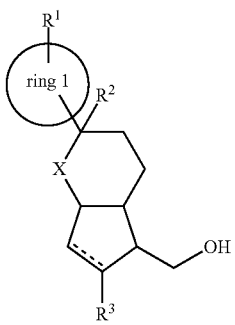

(wherein all symbols are as defined above) and a compound represented by general formula (III):

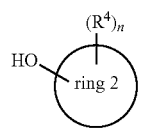

(wherein all symbols are as defined above) to the Mitsunobu reaction.

The Mitsunobu reaction is known, and is carried out by, for example, reacting an alcohol with a phenol derivative in an organic solvent (dichloromethane, diethyl ether, tetrahydrofuran, acetonitrile, benzene, toluene, etc.) at 0 to 60° C. in the presence of an azo compound (diethyl azodicarboxylate (DEAD), diisopropyl azodicarboxylate, 1,1'-(azodicarbonyl)dipiperidine, 1,1'-azobis(N,N-dimethylformamide), etc.) and a phosphine compound (e.g., triphenylphosphine, tributylphosphine, trimethylphosphine, polymer-supported triphenylphosphine, etc.).

A compound in which E is —S— can be produced by the same reaction as mentioned above using a compound represented by general formula (III) in which the hydroxy group is —SH. A compound in which E is —SO— or —SO$_2$— can be produced by subjecting the compound in which E is —S— to an oxidization reaction of a sulfur atom.

The oxidization reaction for converting the compound in which E is —S— to the compound in which E is —SO— is known. For example, the oxidization reaction can be carried out by reacting the compound in which E is —S— at a temperature of −40 to 0° C. in an organic solvent (dichloromethane, chloroform, benzene, hexane, methanol, t-butyl alcohol, acetone, acetonitrile, tetrahydrofuran, acetic acid, N,N-dimethylformamide, etc.), water or a solvent mixture thereof in the presence of 1 to 1.2 equivalents of an oxidizing agent (hydrogen peroxide, sodium periodate, acyl nitrite, sodium perborate, sodium hypochlorite, peracids (3-chloroperbenzoic acid, peracetic acid, etc.), Oxone (trade name, abbreviated as "Oxone", hereinbelow; potassium peroxymonosulfate), potassium permanganate, chromic acid, dimethyldioxolane, etc,).

The oxidization reaction for converting the compound in which E is —S— to the compound in which E is —SO$_2$— is known. For example, the oxidization reaction can be carried out by reacting the compound in which E is —S— at a temperature of 20 to 60° C. in an adequate organic solvent (dichloromethane, chloroform, benzene, hexane, methanol, t-butyl alcohol, acetone, acetonitrile, tetrahydrofuran, acetic acid, N,N-dimethylformamide, etc.), water or a solvent mixture thereof in the presence of an excess amount of an oxidizing agent (hydrogen peroxide, sodium periodate, acyl nitrite, sodium perborate, sodium hypochlorite, peracids (3-chloroperbenzoic acid, peracetic acid), Oxone (trade name), potassium permanganate, chromic acid, dimethyldioxolane, etc.).

Among the compounds represented by general formula (I), a compound in which E is —NH—, i.e., a compound represented by general formula (Ib):

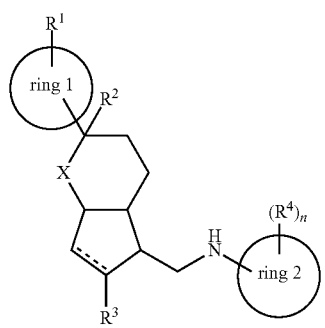

(wherein all symbols are as defined above) can be produced by subjecting a compound represented by general formula (IV):

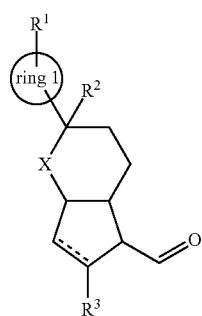

(wherein all symbols are as defined above) and a compound represented by general formula (V):

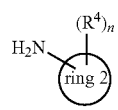

(wherein all symbols are as defined above) to a reductive amination reaction.

The reductive amination reaction is known, and is carried out by, for example, reacting the compounds at a temperature of 0 to 40° C. in an organic solvent (dichloroethane, dichloromethane, etc.) in the presence of a tertiary amine (e.g., triethylamine, diisopropylethylamine, etc.) using an acid (acetic acid, titanium tetrachloride, etc.) and then further carrying out the reaction at a temperature of 0 to 40° C. in the presence of a reducing agent (sodium tri(acetoxy) borohydride, sodium cyanoborohydride, etc.).

Among the compounds represented by general formula (I), a compound in which E is =CH—, i.e., a compound represented by general formula (Ic):

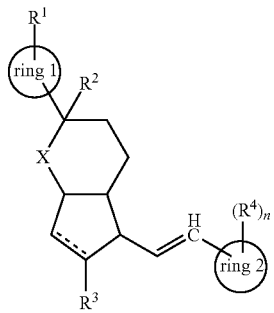
(Ic)

(wherein all symbols are as defined above) can be produced by subjecting a compound represented by general formula (IV) and a compound represented by general formula (VI):

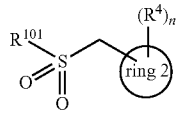
(VI)

(wherein $R^{101}$ represents a phenyl group, a phenyltetrazole group, a benzothiazole group or the like; and other symbols are as defined above) to the below-mentioned reaction.

The reaction is known, and is carried out, for example, at a temperature of −100 to −20° C. in an organic solvent (e.g., anhydrous tetrahydrofuran, dimethoxyethane, toluene, dimethylformamide, etc.) in the presence of a base (e.g., potassium hexamethyldisilazide (KHMDS), lithium diisopropylamide (LDA), butyllithium, etc.).

A compound in which E is —$CH_2$— can be produced by subjecting the compound in which E is =CH— to a known reduction reaction.

The reduction reaction is known, and is carried out, for example, at a temperature of room temperature to about 80° C. under a hydrogen atmosphere in an organic solvent (e.g., methanol, ethanol, ethyl acetate, tetrahydrofuran, acetic acid, 1,2-dimethoxyethane, or a solvent mixture prepared by adequately mixing these organic solvents, etc.) or a solvent mixture of the organic solvent with water in the presence of a palladium catalyst (e.g., palladium-carbon, palladium hydroxide, etc.).

In each of the above-mentioned reactions, the compound which is used as a starting raw material is known or can be produced easily by a known method.

For example, among the compounds represented by general formula (II), a compound represented by general formula (IIa):

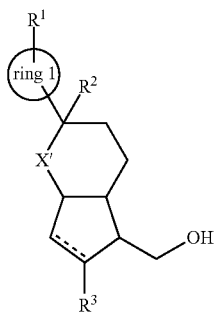
(IIa)

(wherein X' represents —O— or —NH—; and other symbols are as defined above) can be produced in accordance with reaction scheme 1 shown below and optionally carrying out a protection-deprotection reaction.

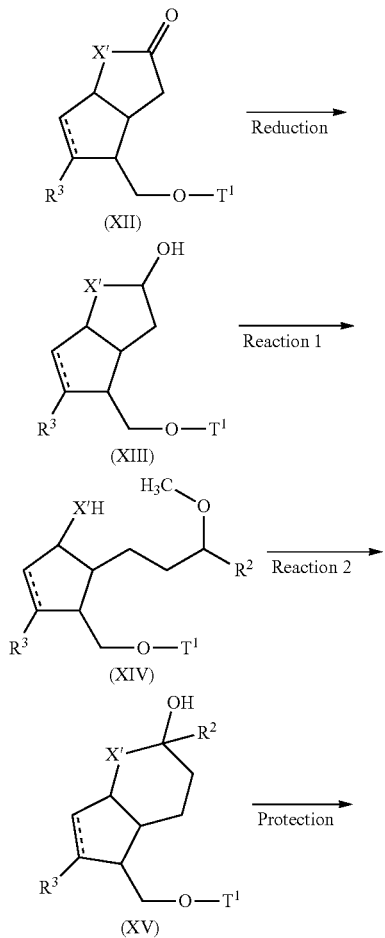

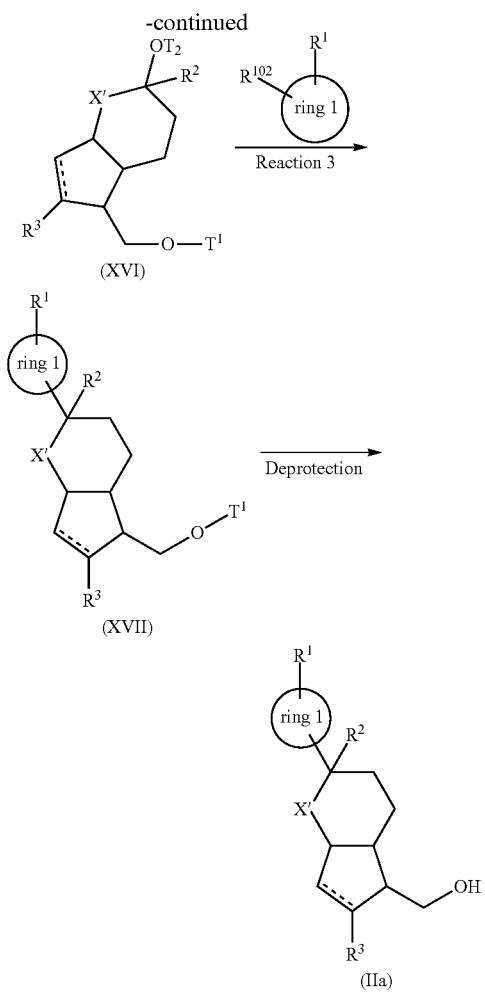

(wherein T¹ and T² represent different hydroxy group-protecting groups (e.g., an acetyl group, a benzoyl group, a 2-tetrahydropyranyl (THP) group, a tert-butyldimethylsilyl (TBDMS or TBS) group, a tert-butyldiphenylsilyl (TBDPS) group, etc.) from each other; $R^{102}$ represents —ZnI, —ZnBr, —ZnCl, —MgI, —MgBr, —MgCl or —Li; and other symbols are as defined above.)

In reaction scheme 1, the reduction reaction is known, and is carried out, for example, at a temperature of −78 to 0° C. in an organic solvent (e.g., toluene, hexane, dichloromethane, tetrahydrofuran, 1,2-dimethoxyethane, diethyl ether, dioxane, etc.) using diisobutylaluminum hydride.

In reaction scheme 1, reaction 1 is known, and is carried out, for example, at a temperature of −78 to 50° C. in an organic solvent (e.g., dry toluene, dimethoxyethane, tetrahydrofuran, etc.) in the presence of a base (e.g., lithium hexamethyldisilazane (LHMDS), lithium diisopropylamide (LDA), butyllithium, potassium tert-butoxide, sodium hydride, etc.) using a Wittig reagent (e.g., (methoxymethyl)triphenylphosphonium chloride, etc.).

In reaction scheme 1, reaction 2 is known, and is carried out, for example, at a temperature of 0 to 100° C. in a solvent mixture of an organic solvent (e.g., dioxane, dry toluene, dimethoxyethane, tetrahydrofuran, etc.) and water using an acid (e.g., hydrochloric acid, acetic acid, paratoluenesulfonic acid, etc.).

In reaction scheme 1, reaction 3 is known, and is carried out, for example, at a temperature of −78 to 50° C. in an organic solvent (e.g., dioxane, dry toluene, dichloromethane, tetrahydrofuran, etc.) in the presence of a Lewis acid (e.g., aluminum chloride, tin chloride, a boron trifluoride-diethyl ether complex, etc.) using an organic metal reagent (e.g., 5-ethoxycarbonyl-2-furanyl zinc bromide, etc.).

In reaction scheme 1, the deprotection reaction is known, and can be carried out in the following manner.

Methyl group, trityl group, methoxymethyl (MOM) group, 1-ethoxyethyl (EE) group, methoxyethoxymethyl (MEM) group, 2-tetrahydropyranyl (THP) group, trimethylsilyl (TMS) group, triethylsilyl (TES) group, t-butyldimethylsilyl (TBDMS) group, t-butyldiphenylsilyl (TBDPS) group, acetyl (Ac) group, pivaloyl group, benzoyl group, benzyl (Bn) group, p-methoxybenzyl group, allyloxycarbonyl (Alloc) group, and 2, 2, 2-trichloroethoxycarbonyl (Troc) group, etc. may be used as protecting groups for hydroxyl group.

Protecting groups which can be removed easily and selectively other than the above protecting groups are also preferred. For example, the groups described in P. G. M. Wuts, T. W. Greene, Green's Protective Groups in Organic Synthesis, Wiley, Fourth Edition, New York, 2007, may be used.

The method of deprotection is known. It includes the method of
(1) Alkaline hydrolysis,
(2) Deprotection under acidic conditions,
(3) Deprotection by Hydrogenolysis,
(4) Deprotection of silyl group,
(5) Deprotection using metal,
(6) Deprotection using metal complex, or the like.

These methods are explained specifically as follows.
(1) Deprotection by alkaline hydrolysis may be carried out, for example, in an organic solvent (e.g. methanol, tetrahydrofuran, dioxane, etc.), using an alkali metal hydroxide (e.g. sodium hydroxide, potassium hydroxide or lithium hydroxide, etc.), an alkaline earth metal hydroxide (e.g. barium hydroxide or calcium hydroxide, etc.) or a carbonate (e.g. sodium carbonate or potassium carbonate, etc.) or an aqueous solution thereof or a mixture thereof at 0-40° C.
(2) Deprotection under acidic conditions may be carried out, for example, in an organic solvent (e.g. dichloromethane, chloroform, dioxane, ethyl acetate, anisole, etc.), using an organic acid (e.g. acetic acid, trifluoroacetic acid, methanesulfonic acid, p-tosylic acid, etc.), or an inorganic acid (e.g. hydrochloric acid or sulfuric acid, etc.) or a mixture thereof (e.g. hydrogen bromide/acetic acid, etc.) at 0-100° C.
(3) Deprotection by hydrogenolysis may be carried out, for example, in a solvent (ethers, (e.g. tetrahydrofuran, dioxane, dimethoxyethane, diethyl ether, etc.), alcohols (e.g. methanol, ethanol, etc.), benzenes (e.g. benzene, toluene, etc.), ketones (e.g. acetone, methyl ethyl ketone, etc.), nitriles (e.g. acetonitrile, etc.), amides (e.g. dimethylformamide, etc.), water, ethyl acetate, acetic acid or two more mixture thereof), in the presence of a catalyst (e.g. palladium on carbon, palladium black, palladium hydroxide, platinum dioxide or Raney-nickel, etc.), at ordinary or elevated pressure of hydrogen gas or in the presence of ammonium formate at 0-200° C.
(4) Deprotection of silyl may be carried out, for example, in water-miscible organic solvent (e.g. tetrahydrofuran, acetonitrile, etc.), using tetrabutylammonium fluoride at 0-40° C.
(5) Deprotection using metal may be carried out, for example, in an acidic solvent (e.g. acetic acid, buffer (pH4.2-

7.2) or a mixture thereof and an organic solvent e.g. tetrahydrofuran), in the presence of a zinc powder, if necessary under sonication, at 0-40° C.

(6) Deprotection using metal complex may be carried out, for example, in an organic solvent (e.g. dichloromethane, dimethylformamide, tetrahydrofuran, ethyl acetate, acetonitrile, dioxane, ethanol, etc.), water or a mixture thereof, in the presence of a trap reagent (e.g. tributyltin hydride, triethylsilane, dimedone, morphorine, diethylamine, pyrrolidine, etc.), an organic acid (e.g. acetic acid, formic acid, 2-ethylhexanoic acid, etc.) and/or an organic acid salt (e.g. sodium 2-ethylhexanate, potassium 2-ethylhexanate, etc.), in the presence or absence of phosphine reagent (e.g. triphenylphosphine, etc.), using a metal complex (e.g. tetrakis (triphenylphosphine)palladium (0), bis(triphenylphosphine) palladium (II) dichloride, palladium (II) acetate, tris (triphenylphosphine)rhodium (I) chloride, etc.) at 0-40° C.

Other methods of deprotection other than the above methods, may be also carried out by methods described in P. G. M. Wuts, T. W. Greene, Green's Protective Groups in Organic Synthesis, Wiley, Fourth Edition, New York, 2007.

As will be apparent to those skilled in the art, the desired compound of the present invention may be easily prepared using a corresponding reaction selected from these deprotection reaction.

Among the compounds represented by general formula (IV), a compound in which X is —O— or —NH— can be produced by subjecting the compound represented by general formula (IIa) to the below-mentioned oxidation reaction.

The oxidation reaction of a hydroxy group is known, and examples thereof include:
(1) A method employing Swern oxidation
(2) A method using a Dess-Martin reagent; and
(3) A method using a TEMPO reagent, or the like.

These methods will be described specifically as follows.

(1) The method employing Swern oxidation is carried out by, for example, reacting oxalyl chloride with dimethyl sulfoxide at −78° C. in an organic solvent (chloroform, dichloromethane, etc.), then reacting an alcohol compound in the resulting solution, and then reacting the resulting product with a tertiary amine (e.g., triethylamine, N,N-diisopropylethylamine, N-methylmorpholine, N-ethylpiperidine, diazabicyclo[5.4.0]undec-7-ene, etc.) at −78 to 20° C.

(2) The method using a Dess-Martin reagent is carried out, for example, at 0 to 40° C. in an organic solvent (e.g., chloroform, dichloromethane, 1,2-dichloroethane, tetrahydrofuran, acetonitrile, t-butyl alcohol, etc.) in the presence of a Dess-Martin reagent (1,1,1-triacetoxy-1,1-dihydro-1,2-benziodoxole-3-(1H)-one) in the presence or absence of a base (e.g., pyridine, etc.).

(3) The method using a TEMPO reagent is carried out, for example, at 20 to 60° C. in an organic solvent (e.g., chloroform, dichloromethane, tetrahydrofuran, toluene, acetonitrile, ethyl acetate, water, etc.) or a solvent mixture thereof, using a TEMPO reagent (2,2,6,6-tetramethyl-1-piperidinyloxy, a free radical) and a reoxidizing agent (e.g., aqueous hydrogen peroxide, sodium hypochlorite, 3-chloroperbenzoic acid, iodobenzene diacetate, potassium peroxymonosulfate (Oxone; trade name), etc.) in the presence or absence of a quaternary ammonium salt (e.g., tetrabutylammonium chloride, tetrabutylammonium bromide, etc.), in the presence or absence of an inorganic salt (e.g., sodium bromide, potassium bromide, etc.), or in the presence or absence of an inorganic base (e.g., sodium hydrogen carbonate, sodium acetate, etc.).

Among the compounds represented by general formula (II), a compound in which X is —S— can be produced with adequately referring to the methods disclosed in International Publication No. 2012/102355 pamphlet and U.S. Pat. No. 4,367,237 and others. A compound in which X is —SO— or —SO$_2$— can be produced by subjecting the compound in which X is —S— to the above-mentioned sulfur atom oxidation reaction.

Among the compounds represented by general formula (II), a compound in which ring 1 is an oxazole or a thiazole, i.e., a compound represented by general formula (IIb):

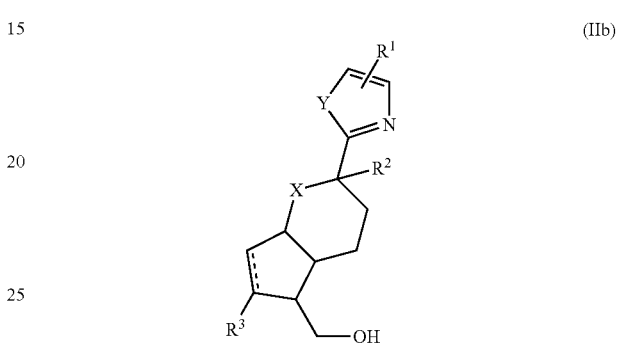

(IIb)

(wherein Y represents —O— or —S—; and other symbols are as defined above) can also be produced through reaction scheme 2 shown below.

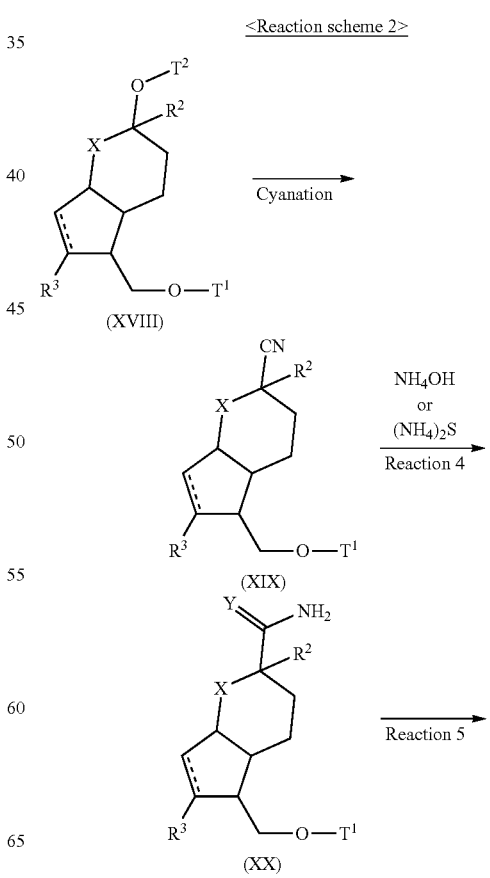

<Reaction scheme 2>

-continued

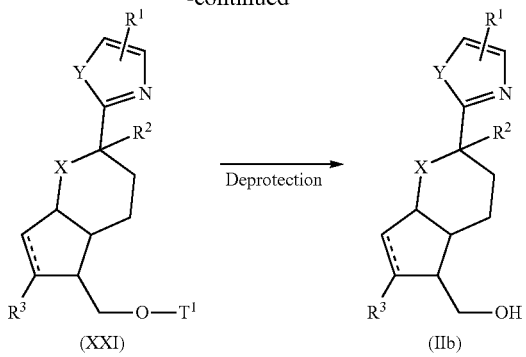

(wherein all symbols are as defined above.)

In reaction scheme 2, the cyanation reaction is known, and is carried out by, for example, at a temperature of −78 to 25° C. in an organic solvent (e.g., dichloromethane, acetonitrile, etc.) in the presence of a Lewis acid (e.g., titanium chloride, iodotrimethylsilane, boron trifluoride-diethyl ether complex, etc.) using a cyanation reagent (e.g., trimethylsilyl cyanide, sodium cyanide, etc.).

In reaction scheme 2, reaction 4 is known. With respect to a compound in which Y=S, reaction 4 is carried out, for example, at a temperature of 0 to 150° C. in an organic solvent (e.g., methanol, dioxane, N,N-dimethylformamide, etc.) in the presence of a base (e.g., pyridine, calcium hydride, sodium methoxide, triethylamine, etc.) or using a sulfurization reagent (e.g., hydrogen sulfide, ammonium sulfide, sodium sulfide, etc.). With respect to a compound in which Y=O, reaction 4 is carried out, for example, at a temperature of 0 to 100° C. in an organic solvent (e.g., methanol, dioxane, N,N-dimethylformamide, etc.) or a solvent mixture of the organic solvent with water, in the presence of a base (e.g., hydroxylamine, sodium hydroxide, potassium carbonate, etc.) or using an acid (sulfuric acid, hydrochloric acid, etc.).

In reaction scheme 2, reaction 5 is known, and is carried out using an α-haloketone compound, for example, at a temperature of −78 to 50° C. in an organic solvent (e.g., dimethoxyethane, ethanol, N,N-dimethylformamide, etc.) in the presence of a base (e.g., sodium hydrogen carbonate, potassium carbonate, sodium hydrogen carbonate, pyridine, etc.) using ethyl bromopyruvate or a dehydration reagent (e.g., trifluoroacetic anhydride, trifluorosulfonic anhydride, etc.).

Among the compounds represented by general formula (XIX) in reaction scheme 2, a compound in which $R^2$ is a $C_{1-4}$ alkyl group can also be produced by subjecting a compound in which $R^2$ is a hydrogen atom among the compounds represented by general formula (XIX) to the below-mentioned reaction.

The reaction is known, and is carried out, for example, at a temperature of −78 to 50° C. in an organic solvent (e.g., diethyl ether, tetrahydrofuran, etc.) in the presence of an alkylating agent (e.g., methyl iodide, ethyl iodide, etc.) using a base (e.g., lithium diisopropylamide, potassium hexamethyldisilazide, etc.).

The compounds which are used as other starting raw materials and the compounds used as reagents are known per se or can be produced easily by combining known methods such as the method disclosed in Comprehensive Organic Transformations: A Guide to Functional Group Preparations, 2nd Edition (Richard C. Larock, John Wiley & Sons Inc., 1999) and the like.

In each of the reactions in the specification, each group may be protected when protection is required, and a compound adequately protected with a protecting group may be subjected to a known deprotection reaction.

In each of the reactions in the specification, a reaction involving heating can be carried out using a water bath, an oil bath or a sand bath or a microwave, as is obvious to persons skilled in the art.

In each of the reactions in the specification, a solid phase-supported reagent which is supported on a high-molecular-weight polymer (e.g., polystyrene, polyacrylamide, polypropylene, polyethylene glycol, etc.) may be used appropriately.

In each of the reactions in the specification, a reaction product can be purified by a normal purification means, for example, a method such as distillation under normal pressure or under reduced pressure, high performance liquid chromatography using silica gel or magnesium silicate, thin layer chromatography, an ion-exchange resin, a scavenger resin, or column chromatography or washing, recrystallization etc. The purification may be carried out after every reaction, or may be carried out after the completion of several reactions.

[Toxicity]

The compound according to the present invention has extremely low toxicity, and is safe enough to be used as a medicament. The toxicity can be evaluated by, for example, employing the following methods.

(1) Histopathological Test

A test compound (30 μL) which is prepared at each of various concentrations is dropwise applied to one eye of a male monkey (a cynomolgus monkey). After the repeated dropwise application for 4 weeks, the monkey is bled to death by cutting the caudal vena cava and the abdominal aorta under anesthesia with sodium thiopental (Ravonal (registered trade name), manufactured by Mitsubishi Tanabe Pharma Corporation), and then eye balls are excised. The excised eye ball is fixed with a fixing solution (a phosphate buffer liquid containing 1% formaldehyde and 2.5% glutaraldehyde) to produce a specimen stained with haematoxylin and eosin. The specimen was subjected to a histopathological test.

(2) Ophthalmic Test

A solution (30 μL) containing a test compound which is prepared at each of various concentrations is dropwise applied to one eye of a male monkey (a cynomolgus monkey) at a single dose to a repeated dose for 4 weeks, and then the below-mentioned ophthalmic test is carried out. With respect to the procedures to be carried out under anesthesia, ketamine hydrochloride [a 0.1 to 0.4 mL/kg intramuscular injection of animal ketamine injection 5% "Fujita" (Fujita Pharmaceutical Co., Ltd.)] and xylazine hydrochloride [a 0.05 to 0.1 mL/kg intramuscular injection of Selactar (registered trade name) 2% (Bayer)] are used for anesthesia. With respect to the procedure to be carried out under mydriasis, a mydriatic agent (an eye drop: Mydrin (registered trade name) P, Santen Pharmaceutical Co., Ltd.) is used.

(2-1) Test with Laser Flare Cell Meter

After dropwise applications of a mydriatic agent to both eyes, an aqueous flare intensity (including the number of cells) is measured with a laser flare cell meter (FC-2000, Kowa Company, Ltd.) under anesthetized conditions. The cornea, crystalline lens and optic media are also observed with the laser flare cell meter in a slit lamp mode. During or after the test, physiological saline is sufficiently applied for the purpose of preventing the cornea from drying caused by ketamine.

(2-2) Measurement of Thickness of Cornea

An animal which is under anesthetized condition is fixed, an ophthalmic surface anesthetic agent (Benoxil (registered trade name) 0.4%, Santen Pharmaceutical Co., Ltd.) is dropwise applied, and then the thickness of the cornea is measured with an ultrasound diagnostic imaging and eye axial length/corneal thickness measurement device (US-4000 Echo scan, Nidek; simply referred to as "a corneal thickness measuring device", hereinbelow). During the measurement, physiological saline is dropwise applied at proper timing for the purpose of preventing the cornea from drying.

[Application to Drug]

The compound according to the present invention has an excellent selective EP2 agonist activity, and is therefore effective as a therapeutic agent for an EP2 receptor-related diseases, including immune diseases (autoimmune diseases such as amyotrophic lateral sclerosis, multiple sclerosis, Sjogren's syndrome, chronic rheumatoid arthritis and systemic lupus erythematosus; a rejection after organ transplantation, etc.), allergic diseases (e.g., bronchial asthma, allergic rhinitis, allergic conjunctivitis, atopic dermatitis, food allergy, etc.), neuronal death, dysmenorrhea, premature birth, miscarriage, baldness, ocular diseases (glaucoma, ocular hypertension, macular edema, macular degeneration, retina and optic nerve tensile force rise, myopia, hypermetropia, astigmatism, dry eye, retinal detachment, cataract, intraocular pressure rise, etc.), erectile dysfunction; arthritis, lung injury, pulmonary fibrosis, pulmonary emphysema, bronchitis, chronic obstructive pulmonary disease, liver injury, acute hepatitis, cirrhosis, shock, nephritis (acute nephritis, chronic nephritis, etc.), renal failure, cardiovascular diseases (hypertension, myocardial ischemia, chronic arterial occlusive disease, vibration disease, etc.), systemic inflammatory response syndrome, sepsis, hemophagocytic syndrome, macrophage activation syndrome, Still's disease, Kawasaki disease, burn injury, systemic granuromatous disease, colitis ulcerosa, Crohn's disease, hypercytokinemia on dialysis, multiple organ failure, bone diseases (bone fracture, bone refracture, intractable bone fracture, bone nonunion, pseudarthrosis, osteomalacia, bone Paget's disease, ankylosing spondylitis, cancer bone metastasis, arthrosis deformans, and bone destruction in analogous diseases thereto, etc.), cartilage injury and others.

The compound according to the present invention may be administered as a combination drug which is combined with other surgical treatment and/or other drug for the purpose of (1) the complementation and/or enhancement of a therapeutic effect, (2) the improvement of pharmacokinetics/absorption of the compound according to the present invention and the reduction of the dose of the compound according to the present invention, and/or (3) the reduction of adverse side effects of the compound according to the present invention.

The combination drug of the compound according to the present invention with other drug may be administered in a form of a compounding agent in which both ingredients are incorporated into one preparation, or may take a form of administration of separate preparations. When administered by formulating into separate preparations, administration by simultaneous administration and time lag is included. In addition, in administration of time lag, the compound according to the present invention may be administered earlier, and other drug may be administered later, or other drug may be administered earlier, and the compound according to the present invention may be administered later. The method for administering a drug to be combined is not particularly limited, oral administration or parenteral administration may be employed.

The above-mentioned other drug may be a low-molecular-weight compound, or a high-molecular-weight protein, a polypeptide, a polynucleotide (DNA, RNA, a gene), an antisense, a decoy, an antibody, a vaccine or the like. The amount of the other drug to be administered can be selected appropriately based on a clinically employed dose amount. The compounding ratio of the compound according to the present invention and the other drug can be selected appropriately depending on the age and body weight of a subject to be administered, the method of administration, the period of administration and the like. For example, the other drug should be used in an amount of 0.01 to 100 parts by weight based on 1 part by weight of the compound according to the present invention. With respect to the other drug, arbitrary two or more of the other drugs may be administered at a proper ratio. The other drug to be combined with the compound according to the present invention include drugs which are so far discovered based on the below-mentioned mechanism, as well as drugs which will be discovered in the future.

For example, when the compound according to the present invention is used as a therapeutic agent for cartilage injury, the compound may be used in combination with, for example, bone morphogenetic protein (BMP), steroidal drug, non-steroidal anti-inflammatory drug, hyaluronic acid preparation, prostaglandins, growth factors, vitamin D derivative, vitamin A derivative, metalloproteinase inhibitor, phosphodiesterase 4 (PDEA) inhibitor, elastase inhibitor, glycosaminoglycan preparation, NFκB decoy oligodeoxynucleotide, opioid analgesic drug, non-opioid analgesic drug, chondroitin sulfate or the like.

For example, when the compound according to the present invention is used as a therapeutic agent for glaucoma, the compound may be used in combination with, for example, sympathetic nerve agonist (α2 agonist: e.g., apraclonidine hydrochloride, etc., β2 agonist: e.g., dipivefrine hydrochloride, etc.), parasympathetic nerve agonist (e.g., pilocarpine hydrochloride, carbachol, demecarium, echothiophate or distigmine bromide, etc.), sympathetic nerve suppressant (α1 blocker: e.g., bunazosin hydrochloride, etc., β blocker: e.g., timolol maleate, befunolol hydrochloride, carteolol hydrochloride or betaxolol hydrochloride, etc., α1β blocker: e.g., levobunolol hydrochloride, nipradilol, etc.), prostaglandin drug (e.g., isopropyl unoprostone, latanoprost, bimatoprost, travoprost, tafluprost, EP2 agonist, EP4 agonist or a DP agonist, etc.), carbonic anhydrase inhibitor (e.g., acetazolamide, diclofenamide, methazolamide, dorzolamide hydrochloride or brinzolamide, etc.), hyperosmotic drug (e.g., glycerin, preparation compounding glycerin and fructose, isosorbide or D-mannitol, etc.), ROCK (Rho kinase) inhibitor (e.g., Y-27632, ripasudil or AR-13324, etc.), NMDA antagonist or the like.

In the combination, the weight ratio of the compound according to the present invention to the other drug is not particularly limited. With respect to the other drug, arbitrary two or more same types or different types of drugs may be used in combination.

The amount of the other drug for administration to be used in combination with the compound according to the present invention can be increased or decreased appropriately based on the clinically employed dose amount of the drug or an analogous drug thereof. The compounding ratio of the compound according to the present invention and the other drug can be controlled appropriately in consideration of the age and weight of a subject to be administered, the method of administration, the period of administration, the disease to be treated, symptom and the like. It is possible to combine about 0.01 to 100 parts by weight of the other drug based on 1 part by weight of the compound according to the present invention. With respect to the other drug, multiple types of drugs may be used. In addition to the above-mentioned drugs, the other drug may be a drug having the same mechanism of action as those of the above-mentioned drugs. The other drug includes drugs which are so far discovered as well as drugs which will be discovered in the future.

The amount of the compound according to the present invention to be administered may vary depending on age, body weight, condition, therapeutic effect, the method of administration, the period of treatment and the like. Generally, the compound may be administered orally at a single dose of 1 mg to 300 mg once or several times per day per adult, or may be administered parenterally at a single dose of 0.1 mg to 150 mg once to several times per day per adult, or may be administered intravenously in a sustainable manner for 1 to 24 hours per day. Among parental administrations, particularly in the case of an eye drop, an eye drop having a concentration of preferably 0.000001 to 5% (w/v), more preferably 0.00001 to 0.05% (w/v) may be dropwise applied one to several drops per one time at a frequency of once to several times (e.g., once to eight times) per day. In the case of an eye ointment, an eye ointment having a concentration of preferably 0.000001 to 5% (w/w), more preferably 0.00001 to 0.05% (w/w) may be applied at a frequency of once to several times (e.g., once to four times) per day.

As mentioned above, the amount to be administered varies depending on various conditions. Therefore, an amount to be administered may be enough to be smaller than the above-mentioned amount to be administered, or an amount to be administered may be required to be larger than the above-mentioned amount to be administered.

To use the compound according to the present invention as a single drug or a companion drug with other drugs for the prevention and/or treatment of said diseases, preparations are usually formed in active substances and various additives or pharmaceutically acceptable excipients, and are administered as oral or parenteral preparation systemically or locally. The pharmaceutically acceptable excipients mean materials except active substances which are generally used for preparations. The pharmaceutically acceptable excipients are preferably excipients which are harmlessness, and do not show any pharmacological effect and inhibit treatment effect of the active substances at the dosage of the drug products. In addition, the pharmaceutically acceptable excipients can be used to enhance effectiveness of the active substances, make production of the drugs easy, stabilize quality and improve usability. Specifically, the material described in "Iyakuhintenkabutujiten" (yakujinippousha, 2000), (edited by International Pharmaceutical Excipients Council Japan)", etc. may be selected according to intentions.

Dosage forms for administration includes, for example, oral preparation (e.g.: tablets, capsules, granules, powders, oral solutions, syrups, oral jelly agents, etc.), oro-mucosal preparation (e.g.: tablets for oro-mucosal application, sprays for oro-mucosal application, semi-solid preparations for oro-mucosal application, gargles, etc.), preparations for injection (e.g.: injections, etc.), preparations for dialysis (e.g.: dialysis agents, etc.), preparation for inhalation (e.g.: inhalations, etc.), preparation for ophthalmic application (e.g.: ophthalmic liquids and solutions, ophthalmic ointments, etc.), preparation for otic application (e.g.: ear preparation, etc.), preparations for nasal application (nasal preparations, etc.), preparation for recta (e.g.: suppositories, semi-solid preparations for rectal application, enemas for rectal application, etc.), preparations for vaginal application (e.g.: tablets for vaginal use, suppositories for vaginal use, etc.) and preparation for cutaneous application (e.g.: solid preparations for cutaneous application, liquids and solutions for cutaneous application, sprays, ointment, creams, gels, patches, etc.).

[Oral Preparation]

Oral preparation include, for example, tablets, capsules, granules, powders, liquids and solution for oral administration, syrups, Jellies for oral administration, etc. As oral preparation, there are Immediate-release dosage forms showing a release pattern of active substances that is not intentionally modified and modified-release dosage forms are preparations showing modified pattern of active substances that is suitably modified for the desired purpose by means of a specific formulation design and/or manufacturing methods. Modified-release dosage forms include enteric-coated and extended-release preparations. Enteric-coated (delayed-release) preparations release the bulk of the active substances not in stomach but mainly in small intestine, in order to prevent degradation or decomposition of the active substances in stomach or to decrease the irritation of the active substances on stomach. Enteric-coated preparations are generally coated with an acid-insoluble enteric film. Extended-release preparations are designed to control the release rate and release period of active substances and to restrict the release to appropriate sites in the gastrointestinal tracts in order to decrease the dosing frequency and/or to reduce adverse or side effects. Extended-release preparations are generally prepared by using suitable agents that prolong the release of the active substances. Oral dosage forms such as capsules, granules and tablets can be coated with appropriate coating agents, such as sugars, sugar alcohols, or polymers, for the purpose of enabling the ingestion easy or of preventing degradation of the active substances.

(1) Tablets

Tablets are solid preparation having a desired shape and size, intended for oral administration, and include orally disintegrating tablets, chewable tablets, effervescent tablets, dispersible tablets, soluble tablets besides generally called tablets such as plain tablets, film-coated tablets, sugar-coated tablets, multi-layered tablets and pressure-coated tablets, etc. Plain tables are usually prepared according to the following methods (a), (b) and (c):

(a) Mix homogeneously active substances and excipients such as diluents, binders and disintegrators, granulate with water or a binder solution by suitable methods, mix with a lubricant, and then compress into a desired shape and size;

(b) Mix homogeneously active substances and excipients such as diluents, binders, and disintegrators, and then directly compress, or compress after adding active substances and lubricant to granules previously prepared from excipients and then mixing homogeneously;

(c) Mix homogeneously active substances and excipients such as diluents and binders, moisten with a solvent, form into a certain shape and size, and then dry by a suitable methods;

Film-coated tablets can be prepared, usually, by coating plain tablets using suitable coating agents such as polymers. Sugar-coated tablets can be prepared, usually, by coating plain tablets using suitable coating agents including sugars and sugar alcohols. Multiple-layer tablets can be prepared by compressing granules of different compositions to form layered tablets by a suitable method. Pressure-coated tablets can be prepared by compressing granules to cover inner core tablets with different compositions. In addition, tablets can be prepared as enteric coated tablets or timed-release tablet by suitable well-known methods. Orally disintegrating tablets, chewable tablets, effervescent tablets, dispersible tablets, soluble tablets are tablets which are added distinct role by selecting suitable excipients, and can be prepared according to said methods. Orally disintegrating tablets are tablets which are quickly dissolved or disintegrated in the oral cavity; Chewable tablets are tablets which are administered by chewing; Effervescent tablets are tablets which are quickly dissolved or dispersed with bubbles in water; Dispersible tablets are tablets which are administered after having been dispersed in water; Soluble tablets are tablets which are administered after having been dissolved in water. Effervescent tablets can be prepared using suitable acidic substances and carbonates or hydrogen carbonates as excipients.

(2) Capsules

Capsules are preparations enclosed in capsules or wrapped with capsule bases, intended for oral administration. Capsules are classified into hard capsules and soft capsules. Hard capsules can be prepared by a method where a homogeneous mixture of active substances with diluents and other suitable excipients, or granules or formed masses prepared by a suitable methods, are filled into capsule shells as they are or after slight compression. Soft capsules can be prepared by a method where active substances and suitable excipients are mixed, enclosed by a suitable capsule base such as gelation plasticized by addition of glycerin, D-sorbitol, etc. and molded in a suitable shape and size. Capsules can be prepared as enteric-coated or extended-release capsules by a suitable well-known method. Coloring agents and preservatives, etc. may be added to the capsule bases.

(3) Granules

Granules are preparations prepared by granulation, and include effervescent granules besides generally called granules. Granules can be prepared by the following methods (a), (b), and (c);

(a) To powdery active substances add diluents, binders, disintegrators, or other suitable excipients, mix to homogenize, and granulate by a suitable method;

(b) To previously granulated active substances add excipients such as diluents, and mix to homogenize;

(c) To previously granulated active substances add excipients such as diluents, and granulate by a suitable method; Granules can be coated if necessary, and can be prepared as enteric-coated or extended-release granules. Effervescent granules can be prepared using suitable acidic substances and carbonates or hydrogen carbonates. Effervescent granules are granules which are quickly dissolved or dispersed with bubbles in water. Granules can be prepared as fine grain agents by adjusting particle size.

(4) Powders

Powders are preparations in powder form, and are usually prepared by homogeneously mixing active substances with diluents or other suitable excipients.

(5) Liquids and Solution for Oral Administration

Liquids and solution for oral administration are preparations in liquid form or flowable and viscous gelatinous state, and elixirs, suspensions, emulsions and lemonades are included in this category besides generally called Liquids and solution for oral administration. Liquids and solution for oral administration are usually prepared by dissolving, emulsifying or suspending active substances in purified water together with excipients, and by filtering if necessary. Elixirs are clear, sweetened and aromatic liquid preparations, containing ethanol, and are usually prepared by dissolving solid active substances or their extractives in ethanol and purified water, adding aromatic agents and sucrose, other sugars or sweetening agents, and clarifying by filtration or other procedure. Suspensions are liquid preparations of active substances suspended finely and homogeneously in a vehicle, and are usually prepared by adding suspending agent or other suitable excipients and purified water or oil to solid active substances, and suspending homogeneously as the whole by a suitable method. Emulsions are liquid preparations of active substances emulsified finely and homogeneously in a liquid vehicle, and are usually prepared by adding emulsifying agents and purified water to liquid active substances, and emulsifying finely and homogeneously by a suitable method. In addition, Lemonades are sweet and sour, clear liquid preparations, intended for oral administration.

(6) Syrups

Syrups are viscous liquid or solid preparations containing sugars or sweetening agents, and include preparation for syrups. Syrups are usually prepared by dissolving, mixing, suspending or emulsifying active substances in a solution of sucrose, other sugars or sweetening agents, or in simple syrup. Where necessary, the mixture is boiled, and filtered while hot. Preparations for syrups are preparations in form of granules or powders, which becomes syrups by adding water. They may be termed "dry syrups". Preparations for syrups are usually prepared with sugars or sweetening agents according to said preparation method of granules or powders.

(7) Jellies for Oral Administration

Jellies for oral administration are non-flowable gelatinous preparations having a certain shape and size, and usually prepared by mixing active substances with suitable excipients and polymer gel base, gelatinizing and forming into a certain shape and size by a suitable method.

[Preparation for Oro-Mucosal Application]

(1) Tablets for Oro-Mucosal Application

Tablets for oro-mucosal application are solid preparations having a certain form, and include troches/lozenges, sublingual tablets, buccal tablets, mucoadhesive tablets and medicated chewing gums. Preparations for oro-mucosal application are usually prepared according to said method of tablets. Troches/lozenges are tablets for oro-mucosal application, which are gradually dissolved or disintegrated in the mouth; Sublingual tablets are tablets for oro-mucosal application, from which active substances are quickly dissolved sublingually and absorbed via the oral mucosa; Buccal tablets are tablets for oro-mucosal applications, from which the active substances are dissolved gradually between the cheek and teeth, and absorbed via the oral mucosa; Mucoadhesive tablets are tablets for oro-mucosal application that are applied by adhesion to the oral mucosa; Medicated chewing gums are tablets for oro-mucosal application, releasing active substances by chewing.

(2) Spray for Oro-Mucosal Application

Spray for oro-mucosal application are preparation that are applied active substances by spraying into the oral cavity in mist, powder, foam or paste forms, and are usually prepared by dissolving or suspending active substances and suitable excipients in a solvent, filter, where necessary, and fill into a container together with liquefied or compressed gas, or dissolving or suspending active substances and suitable excipients in a solvent, and fill into a container, and fit with a pump for spraying.

(3) Semi-Solid Preparations for Oro-Mucosal Application

Semi-solid preparations for oro-mucosal application are preparation in cream, gel or ointment forms, intended for application to the oral mucosa. Semi-solid preparations for oro-mucosal application are usually prepared by emulsifying active substances together with excipients using purified water and oil component such as petrolatum, or by homogenizing active substances together with suitable excipients using polymer gel or oil and fats as the base. Creams are semi-solid preparations, which are in the form of oil-in-water or water-in-oil emulsions. Hydrophobic preparations in the form of water-in-oil emulsions may be termed "Oily creams". Creams are usually prepared by mixing homogeneously and emulsifying an oil-phase component and a water-phase component, both warmed, of which either one contains the active substances. There components have the following constituents. Oil-phase component: Vaseline, fatty alcohols, etc., with or without emulsifying agents or other suitable excipients. Water-phase component: purified water with or without emulsifying agents or other suitable excipients. Gels are gelatinous preparations. There are aqueous gels and oily gels. Aqueous gels are usually prepared by adding polymers, other excipients and purified water to active substances, dissolving or suspending, and gelatinizing by warming and cooling or by adding gelatinizing agents. Oily gels are usually prepared by adding liquid oily bases such as glycols, fatty alcohols and other excipients to active substances and mixing. Ointments are semi-solid preparations, which dissolve or disperse active substances in a base. There are two types, hydrophobic ointments and hydrophilic ointments. Hydrophobic ointments are usually prepared by warming to melt hydrophobic bases such as fatty oils, waxes or paraffin, adding and mixing active substances in the base to be dissolved or dispersed, and kneading the whole to make homogeneous. Hydrophilic ointments are usually prepared by warming to melt hydrophilic bases such as macrogol, adding and mixing active substances in the bases, and kneading the whole to make homogenous.

(4) Preparations for Gargle

Preparations for gargle are liquid preparations intended to apply locally to the oral and throat cavities. Solid type preparations to be dissolved in water before use are also included in this category. Preparations for gargle are usually prepared by dissolving active substances in a solvent together with suitable excipients, and filtering where necessary. Solid preparations are prepared according to said method of tablets or granules.

[Preparation for Injection]

(1) Injections

Injections are sterile preparations to be administered directly into the body through skin, muscle or blood vessel, usually in form of a solution, a suspension or an emulsion of active substances, or of a solid that contains active substances to be dissolved or suspended before use, and include freeze-dried injections, powders, prefilled syringes, cartridges, parenteral infusions, implants/pellets and prolonged-release injections besides generally called injections. Injections are prepared by the following method (a) and (b):

(a) Dissolve, suspend or emulsify active substances with or without excipients in water for injection or an aqueous or non-aqueous vehicle homogeneously, fill into containers for injection, seal, and sterilize.

(b) Dissolve, suspend or emulsify active substances with or without excipients in water for injection or an aqueous or non-aqueous vehicle, and filtrate aseptically, or prepare aseptically a homogeneous liquid, fill into containers for injection, and seal;

Freeze-dried injections are usually prepared by dissolving active substances with or without excipients such as diluents in water for injection, sterilizing the solution by aseptic filtration, filling the filtrate directly into individual containers for injection and being freeze-dried, or dividing the filtrate in special containers, being freeze-dried and transferred into individual containers for injection. Powder for injections are usually prepared by filtrating aseptically a solution of active substances, obtaining powders by crystallization from the solution or mixing additionally the powders with sterilized excipients, and filling the powders into individual containers for injections. Prefilled syringes for injections are usually prepared by dissolving, suspending or emulsifying active substances with or without excipients in a vehicle, and filling into syringes. Cartridges are used by fixing in an injection device for exclusive use. Cartridges for injection are usually prepared by dissolving, suspending or emulsifying active substances with or without excipients in a vehicle, and filling into cartridges. Parenteral infusions are usually injections of not less than 100 mL, intended for intravenous administration. Implants/Pellets are solid or gel-like form injections, intended for subcutaneous or intramuscular administration by means of an implant device or operative treatment, for the purpose of releasing active substances for a long period of time. Implants/Pellets are usually prepared in a form of pellet, microsphere or gel using biodegradable polymers. Prolonged release injections are injections to be used for intramuscular administration, for the purpose of releasing active substances for a long period of time, and usually prepared by dissolving or suspending active substances in a non-aqueous vehicle such as vegetable oil, or by suspending microspheres prepared with biodegradable polymers.

[Preparations for Dialysis]

(1) Dialysis Agents

Dialysis agents are preparations in liquid, or in solid which are to be dissolved before use, intended for peritoneal dialysis or hemodialysis, and include peritoneal dialysis agents and hemodialysis agents. Peritoneal dialysis agents are sterile dialysis agents, intended to be used for peritoneal dialysis, and are usually prepared by dissolving active substances with suitable excipients in a vehicle to make a certain volume, or by filling active substances combined with suitable excipients in a container, and sealing it. Sterilize if necessary. In the case of solid preparations to be dissolved before use, it can be prepared according to said preparation method of tablets or granules. Hemodialysis agents are dialysis agents to be used for hemodialysis, and are usually prepared by dissolving active substances with excipients in a vehicle to make a certain volume, or by filling active substances with excipients in a container. In the case of the solid preparations to be dissolved before use, it can be prepared according to said preparation method of tablets or granules.

[Preparation for Inhalation]

Inhalations (1) Inhalations are preparations intended for administration as aerosols to the bronchial tubes or lung. Inhalations are classified to dry powder inhalers, inhalation liquid preparations and metered-dose inhalers. Dry powder inhalers are preparations which deliver a constant respiratory intake, intended for administration as solid particle aerosols, and are usually prepared by pulverizing active substances into fine particles. Where necessary, lactose or other suitable excipients are added to make homogeneous mixture. Inhalation liquid preparations are liquid inhalations which are administered by an inhalation device such as operating nebulizer.

Inhalation liquid preparations are usually prepared by mixing active substances with a vehicle and suitable isotonic agents and/or pH adjusting agents to make a solution or suspension, and by filtering where necessary. Metered-dose inhalers are preparations which deliver a constant dose of active substances from the container together with propellant filled in. Metered-dose inhalers are usually prepared by dissolving active substances with a suitable dispersing agents and stabilizers in a vehicle to make a solution or suspension, and by filling in pressure-resistant containers together with liquid propellant, and setting metering valves.

[Preparation for Ophthalmic Application]

(1) Ophthalmic Liquids and Solutions

Ophthalmic liquids and solutions are sterile preparations of liquid, or solid to be dissolved or suspended before use, intended for application to the conjunctival sac or other ocular tissues. Ophthalmic liquids and solutions are usually prepared by dissolving, suspending active substances in a vehicle after adding excipients to make a constant volume, or mixing active substances and excipients, and filling into containers.

(2) Ophthalmic Ointments

Ophthalmic ointments are sterile preparations of semi-solid, intended for application to the conjunstival sac and other ocular tissues. Ophthalmic ointments are usually prepared by mixing homogeneously solution of or finely powdered active substances with petrolatum or other bases, and filling into containers.

[Preparation for Otic Application]

(1) Ear Preparation

Ear preparations are liquid, semi-solid, or solid preparations which are to be dissolved or suspended before use, intended for application to the external or internal ear. Ear preparations are usually prepared by filling in containers with liquids in which active substances and excipients are dissolved or suspended in a vehicle to make a constant volume, or with powders in which active substances and excipients are mixed.

[Preparations for Nasal Application]

(1) Nasal Preparations

Nasal preparations are preparations intended for application to the nasal cavities or nasal mucous membrane. Nasal preparations are classified into Nasal dry powder inhalers and Nasal liquid preparations. Nasal dry powder inhalers are fine powdered preparations, intended for application to the nasal cavities. Nasal dry powder inhalers are usually prepared by pulverizing active substances into moderately fine particles, or by mixing homogeneously with excipients where necessary. Nasal liquids and solutions are liquid preparations, or solid preparations to be dissolved or suspended before use, intended for application to the nasal cavities. Nasal liquids and solutions are usually prepared by dissolving or suspending active substances in a vehicle together with excipients, and filtering where necessary. Isotonic agents and/or pH adjusting agents may be used.

[Preparations for Rectal Application]

(1) Suppositories for Rectal Application

Suppositories for rectal application are semi-solid preparations of a desired shape and size, intended for intrarectal application, which release active substances by melting at body temperature or dissolving or dispersing gradually in the secretions. Suppositories for rectal application are usually prepared by mixing homogeneously active substances and excipients such as dispersing agents and emulsifying agents, dissolving or suspending uniformly in a base which is liquefied by warming, filling a constant volume of the resultant material into containers, and molding it into a shape and size. Lipophilic bases or hydrophilic bases are usually used.

(2) Semi-Solid Preparations for Rectal Application

Semi-solid preparations for rectal application are preparations which are in a form of cream, gel or ointment intended for application to around or inside of the anus. Semi-solid preparations for rectal application are usually prepared by emulsifying active substances with excipients in purified water and oil component such as Vaseline, or by homogeneously mixing active substances and excipients in a base of polymer gel or grease. Creams for rectal application are usually prepared by mixing homogeneously and emulsifying an oil-phase component (such as vaseline, fatty alcohols, etc.) and a water phase component (such as purified water with or without emulsifying agents or other suitable excipients), both warmed, of which either one contains the active substances. Gels for rectal application are gelatinous preparation. There are aqueous gels and oily gels. Aqueous gels are prepared adding polymers, other excipients and purified water to active substances, and dissolving or suspending, and gelatinizing by warming and cooling or by adding gelatinizing agents. Oily gels are prepared by adding liquid oily bases such as glycols, fatty alcohols and other excipients to active substances and mixing. Ointments for rectal application are semi-solid preparations, which dissolve or disperse active substances in a base. There are two types, hydrophobic ointment and hydrophilic ointments. Hydrophobic ointments are usually prepared by warming to melt hydrophobic bases such as fatty oils, waxes or paraffin, adding and mixing active substances in the bases to be dissolved or dispersed, and kneading the whole to make homogeneous. Hydrophilic ointments are usually prepared by warming to melt hydrophilic bases such as macrogol, adding and mixing active substances in the bases, and kneading the whole to make homogeneous.

(3) Enemas for Rectal Application

Enemas for rectal application are preparations in liquid form or viscous and gelatinous state, intended for applications via anus. Enemas for rectal application are preparations are usually prepared by dissolving or suspending active substances in purified water or suitable aqueous vehicle to make a given volume, and filling in containers. Dispersing agents, stabilizers and/or pH adjusting agents may be used.

[Preparations for Vaginal Application]

(1) Tablets for Vaginal Use

Tablets for vaginal use are solid applications of a desired shapes and size, intended for application to the vagina, which release active substances by dissolving or dispersing gradually in the secretions. Tablets for vaginal use are usually prepared according to said preparation method of tablets.

(2) Suppositories for Vaginal Use

Suppositories for vaginal use are semi-solid preparations of a desired shapes and size, intended for application to the vagina, which release active substances by melting at body temperature or by dissolving or dispersing gradually in the secretions. Suppositories for vaginal use are usually prepared according to said preparation method of suppositories for rectal applications.

[Preparation for Cutaneous Application]

(1) Solid Preparations for Cutaneous Application

Solid preparations for cutaneous application are solid preparations for cutaneous application skin (including scalp) or nails. Powders for cutaneous application are included in this category. Powders for cutaneous application are powdery solid preparations intended for external application.

Powders for cutaneous application are usually prepared by mixing homogeneously active substances and excipients such as diluents and pulverizing the mixture.

(2) Liquids and Solutions for Cutaneous Application

Liquids and solutions for cutaneous application are liquid preparations intended for application to the skin (including scalp) or nails. Liniments and lotions are included in this category. Liquids and solutions for cutaneous application are usually prepared by mixing active substances and excipients in a vehicle, and filtering if necessary. Liniments are liquid or muddy preparations intended for external application to the skin by rubbing. Lotions are external liquids in which active substances are dissolved, emulsified or finely dispersed in an aqueous vehicle. Lotions are usually prepared by dissolving, suspending or emulsifying active substances in purified water with excipients and making homogeneous as a whole.

(3) Spray for Cutaneous Application

Spray for cutaneous application are preparations intended for spraying active substances onto the skin in mists, powders, forms or paste state. Spray for cutaneous application are classified into aerosols for cutaneous application and pump sprays for cutaneous application. Spray for cutaneous applications are usually prepared by dissolving or suspending active substances in a vehicle, filtering where necessary, and filling in containers. Aerosols for cutaneous application are sprays which atomize active substances together with liquefied or compressed gas filled in containers. Aerosols for cutaneous application are usually prepared by dissolving or suspending active substances in a vehicle, filling with liquefied propellants in pressure-resistant containers, and setting a continuous spray valve. If necessary, dispersing agents and stabilizer may be used. Pump sprays for cutaneous application are sprays which atomize active substances in containers by pumping. Pump sprays for cutaneous application are usually prepared by dissolving or suspending active substances with excipients in a vehicle, filling in containers and setting pumps to the containers.

(4) Ointments

Ointments are semi-solid preparations to be applied to the skin, which dissolve or disperse active substances in a base. There are two types, hydrophobic ointments and hydrophilic ointments. Hydrophobic ointments are usually prepared by warming to melt hydrophobic bases such as fatty oils, waxes or paraffin, adding and mixing active substances in the base to be dissolved or dispersed, and Kneading the whole to make homogeneous. Hydrophilic ointments are usually prepared by warming to melt hydrophilic bases such as macrogol, adding and mixing active substances in the bases, and kneading the whole to make homogenous.

(5) Creams

Creams are semi-solid preparations to be applied to the skin, which are in the form of oil-in-water or water-in-oil emulsions. Hydrophobic preparations in the form of water-in-oil emulsions may be termed "Oily creams". Creams are usually prepared by mixing homogeneously and emulsifying an oil-phase component and a water-phase component, both warmed, of which either one contains the active substances. There components have the following constituents. Oil-phase component: Vaseline, fatty alcohols, etc., with or without emulsifying agents or other suitable excipients. Water-phase component: purified water with or without emulsifying agents or other suitable excipients.

(6) Gels

Gels are gelatinous preparations intended for application to the skin. There are aqueous gels and oily gels. Aqueous gels are usually prepared by adding polymers, other excipients and purified water to active substances, dissolving or suspending, and gelatinizing by warming and cooling or by adding gelatinizing agents. Oily gels are usually prepared by adding liquid oily bases such as glycols, fatty alcohols and other excipients to active substances and mixing.

(7) Patches

Patches are preparations intended to be attached on the skin. Patched are classified into Tapes/Plasters and Cataplasms/Gel patches. Patches are usually prepared by mixing active substances homogeneously with a base such as a polymer or a mixture of polymers, spreading on a backing layer or liner, and cutting into a given size. Percutaneous absorption type preparations may be prepared by using a release rate-controlling membrane. Where necessary, adhesive agents or penetration enhancers may be used. Tapes/Plasters are patches which are prepared with bases of practically no water contain. Tapes/Plasters are usually prepared by mixing homogeneously active substances with or without excipients and a base of non water-soluble natural or synthetic polymers such as resins, plastics or rubber, and spreading on a cloth or spreading and sealing on a cloth or plastic film, cutting into a given size. The preparations may be also prepared by filling a mixture of active substances and a base with or without other excipients in releasers composed with a release-controlling film, supporter and liner. Cataplasms/Gels are patches using water containing bases. Cataplasms/Gels patches are usually prepared by mixing active substances, purified water, and glycerin or other liquid materials, or by mixing and kneading natural or synthetic polymers, which are soluble in water or absorbent of water, with purified water, adding active substances, mixing the whole homogeneously, spreading on a cloth or film, and cutting into a given size.

EXAMPLES

Hereinbelow, the present invention will be described in detail with reference to examples. However, the present invention is not intended to be limited to these examples.

The solvents shown in parentheses in the section of separation by chromatography and in TLC represent eluting solvents or developing solvents used, and the ratios are by volume.

NMR data are $^1$H-NMR data as measured at 300 MHz, unless otherwise specified.

The solvents in parentheses in the sections of NMR are solvents used for the measurements.

The compound names used herein are named using a computer program, ACD/Name Batch (registered trade name), which performs naming according to the rule of IUPAC, or according to IUPAC nomenclature. For example, a compound represented by the following formula:

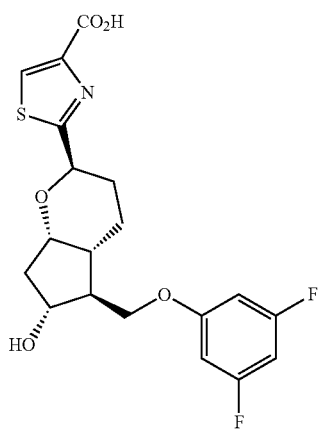 [SMILES: O=C(O)c1csc([C@H]2CC[C@@H]3[C@@H](COc4cc(F)cc(F)c4)[C@H](O)C[C@@H]3O2)n1]

is named as 2-{(2R,4aR,5S,6R,7aS)-5-[(3,5-difluorophenoxy)methyl]-6-hydroxyoctahydrocyclopenta[b]pyran-2-yl}-1,3-thiazole-4-carboxylic acid.

Production Examples

Reference Example 1: (3aR,4S,5R,6aS)-4-(((tert-butyldiphenylsilyl)oxy)methyl)-5-((tetrahydro-2H-pyran-2-yl))oxy)hexahydro-2H-cyclopenta[b]furan-2-one (Reference compound 1)

N,N-Dimethylformamide (2.1 L) and imidazole (183 g) were added to (3aR,4S,5R,6aS)-4-(hydroxymethyl)-5-((tetrahydro-2H-pyran-2-yl)oxy)hexahydro-2H-cyclopenta[b]furan-2-one (458 g) under nitrogen stream, and then tert-butyldiphenylchlorosilane (541 g) was added dropwise thereto under ice cooling. The resulting product was stirred at room temperature for 1 hour, then ethanol (57 mL) was added to the reaction solution, and then the resulting solution was stirred for 30 minutes. Methyl tert-butyl ether and 0.5 N hydrochloric acid were added to the reaction solution. The organic layer was washed with water and saturated brine, then dried over anhydrous sodium sulfate, and then filtrated. The filtrate was concentrated under reduced pressure to produce the title compound having the following physical property value. The compound thus produced was used in the subsequent reaction without purification.
TLC: Rf 0.45 (hexane:ethyl acetate=2:1).

Reference Example 2: (3aR,4S,5R,6aS)-4-(((tert-butyldiphenylsilyl)oxy)methyl)-5-((tetrahydro-2H-pyran-2-yl)oxy)hexahydro-2H-cyclopenta[b]furan-2-ol (Reference compound 2)

Toluene (1.5 L) was added to Reference compound 1 (463 g) under nitrogen stream, the resulting product was cooled with dry ice/methanol, and then 1.00 M diisobutylaluminum hydride/toluene (995 mL) was added dropwise to the solution. The resulting solution was stirred at the same temperature for 1 hour, and then an aqueous solution (600 mL) of potassium sodium L-tartrate (434 g) was added dropwise thereto. The resulting solution was stirred at room temperature overnight, and then methyl tert-butyl ether (500 mL) and water (500 mL) were added to the reaction solution. The organic layer was washed with water and saturated brine, then dried over anhydrous sodium sulfate, and then filtrated. The filtrate was concentrated under reduced pressure to produce the title compound having the following physical property value. The compound thus produced was used in the subsequent reaction without purification.
TLC: Rf 0.25 (hexane:ethyl acetate=2:1).

Reference Example 3: (1 S,2R,3S,4R)-3-(((tert-butyldiphenylsilyl)oxy)methyl)-2-(3-methoxyallyl)-4-((tetrahydro-2H-pyran-2-yl)oxy)cyclopentanol (Reference compound 3)

Tetrahydrofuran (2.3 L) was added to 85% potassium tert-butoxide (298 g) under nitrogen stream, and then (methoxymethyl)triphenylphosphonium chloride (775 g) was added to the resulting solution under ice cooling. The reaction solution was stirred for 30 minutes under ice cooling, and then a solution of Reference compound 2 (488 g) in tetrahydrofuran (600 mL) was added dropwise to the reaction solution. The reaction solution was stirred for 30 minutes under ice cooling, and then water (100 mL) was added dropwise to the reaction solution. Water and saturated brine were added to the reaction solution, and the reaction solution was extracted with ethyl acetate. The organic layer was washed with saturated brine, then dried over anhydrous sodium sulfate, and then filtrated. The filtrate was concentrated under reduced pressure, diisopropyl ether (400 mL) and hexane (400 mL) were added to the residue (1100 g), and the resulting solution was filtrated, and then concentrated under reduced pressure. The residue was purified by silica gel column chromatography (hexane:ethyl acetate=1:0→10:1→5:1→2:1) to produce the title compound (418 g) having the following physical property value.
TLC: Rf 0.45 (hexane:ethyl acetate=2:1).

Reference Example 4: (4aR,5S,6R,7aS)-5-(((tert-butyldiphenylsilyl)oxy)methyl)octahydrocyclopenta[b]pyran-2,6-diol (Reference compound 4)

Tetrahydrofuran (600 mL), water (600 mL) and acetic acid (1.2 L) were added to Reference compound 3 (418 g) under nitrogen stream, and the resulting solution was stirred for 3 hours at an inside temperature of 55° C. The reaction solution was cooled to room temperature, and then toluene (1.5 L) and saturated brine (400 mL) were added to the reaction solution. The organic layer was washed with water, a saturated aqueous sodium hydrogen carbonate solution and saturated brine, then dried over anhydrous sodium sulfate, then filtrated, and then concentrated under reduced pressure. The residue was purified by silica gel column chromatography (hexane:ethyl acetate=1:0→4:1→2:1→1:3) to produce the title compound (229 g) having the following physical property value.
TLC: Rf 0.20 (hexane:ethyl acetate=1:1).

Reference Example 5: (4aR,5S,6R,7aS)-5-(((tert-butyldiphenylsilyl)oxy)methyl)octahydrocyclopenta[b]pyran-2,6-diyl diacetate (Reference compound 5)

Pyridine (900 mL) was added to Reference compound 4 (229 g) under nitrogen stream, and then acetic anhydride (182 g) was added dropwise to the reaction solution over 10 minutes under ice cooling. The reaction solution was stirred at room temperature overnight, and the reaction solution was poured into a solution composed of toluene (500 mL), water (1.2 L) and ice (600 g) to terminate the reaction. The reaction solution was extracted with toluene, and then the organic layer was washed with water, 1 N hydrochloric acid, a saturated aqueous sodium hydrogen carbonate solution and saturated brine, then dried over anhydrous sodium sulfate, and then filtrated. The filtrate was concentrated under reduced pressure to produce the title compound having the following physical property value. The compound thus produced was used in the subsequent reaction without purification.

TLC: Rf 0.25 (hexane:ethyl acetate=4:1).

Reference Example 6: (2R,4aR,5S,6R,7aS)-5-(((tert-butyldiphenylsilyl)oxy)methyl)-2-cyanooctahydrocyclopenta[b]pyran-6-yl acetate (Reference compound 6)

Anhydrous acetonitrile (1.4 L) and 96%-trimethylsilyl cyanide (91.9 g) were added to Reference compound 5 (268 g) under nitrogen stream, and then 1 M tin tetrachloride/dichloromethane (494 mL) was added dropwise to the resulting solution under ice cooling. The reaction solution was stirred for 40 minutes under ice cooling, and the reaction solution was then poured into a solution composed of sodium hydrogen carbonate (468 g), ice (600 g) and water (600 mL) to terminate the reaction. Water and ethyl acetate were added to the mixed solution, and then the reaction solution was extracted, and the aqueous layer was extracted with ethyl acetate/hexane (1:1). The organic layer was washed with water and saturated brine, then dried over anhydrous sodium sulfate, and then filtrated. The filtrate was concentrated under reduced pressure to produce the title compound having the following physical property value. The compound thus produced was used in the subsequent reaction without purification.

TLC: Rf 0.35 (hexane:ethyl acetate=4:1).

Reference Example 7: (2R,4aR,5S,6R,7aS)-5-(((tert-butyldiphenylsilyl)oxy)methyl)-2-carbamothioyloctahydrocyclopenta[b]pyran-6-yl acetate (Reference compound 7)

Pyridine (1.2 L) was added to Reference compound 6 (238 g), then a 20% ammonium sulfide solution (490 g) was added dropwise to the resulting solution under ice cooling, and then the reaction solution was stirred at 10° C. or lower for 24 hours. Ice (300 g) and water (2.0 L) were added to the reaction solution, and the reaction solution was extracted with toluene. The organic layer was washed with water and saturated brine, then dried over anhydrous sodium sulfate, and then filtrated. The filtrate was concentrated under reduced pressure, and then azeotropically dried with toluene (500 mL) three times to produce a concentrated residue. The residue was purified by silica gel column chromatography (hexane:ethyl acetate=9:1→5:1→4:1→3:1→2:1) to produce the title compound (95.4 g) having the following physical property value.

TLC: Rf 0.30 (hexane:ethyl acetate=2:1).

Reference Example 8: ethyl 2-((2R,4aR,5S,6R,7aS)-6-acetoxy-5-(((tert-butyldiphenylsilyl)oxy)methyl)octahydrocyclopenta[b]pyran-2-yl)thiazole-4-carboxylate (Reference compound 8)

A solution of Reference compound 7 (145 g) in dimethoxyethane (1.1 L) was cooled with dry ice/methanol under nitrogen stream, and then potassium hydrogen carbonate (202 g) was added thereto. 90% Ethyl bromopyruvate (164 g) was added dropwise to the reaction solution, and then stirred for 4 hours. Pyridine (160 g) was added to the reaction solution, then trifluoroacetic anhydride (212 g) was added dropwise to the solution, then the resulting solution was stirred for 30 minutes, and then water (600 mL) was added thereto. The reaction solution was heated to room temperature, and then the reaction solution was extracted with ethyl acetate. The organic layer was washed with water and saturated brine, then dried over anhydrous sodium sulfate, then filtrated, and the filtrate was concentrated under reduced pressure. The residue was purified by silica gel column chromatography (hexane:ethyl acetate=1:0→10:1→6:1→4:1→3:1) to produce the title compound (156 g) having the following physical property value.

TLC: Rf 0.45 (hexane:ethyl acetate=2:1).

Reference Example 9: ethyl 2-((2R,4aR,5S,6R,7aS)-6-acetoxy-5-(hydroxymethyl)octahydrocyclopenta[b]pyran-2-yl)thiazole-4-carboxylate (Reference compound 9)

Tetrahydrofuran (370 mL) and acetic acid (38.5 g) were added to Reference compound 8 (156 g) under nitrogen stream, and then 1 M tetra-n-butylammonium fluoride/tetrahydrofuran (642 mL) was added dropwise to the resulting solution. The reaction solution was stirred at an inside temperature of 44° C. for 2 hours and then cooled to room temperature, and then a saturated aqueous sodium hydrogen carbonate solution (600 mL) was added to the reaction solution. Water was added to the resulting mixture, and then the reaction solution was extracted with ethyl acetate. The organic layer was washed with water and saturated brine, then dried over anhydrous sodium sulfate, and then filtrated. The filtrate was concentrated under reduced pressure, and the residue was purified by silica gel column chromatography (hexane:ethyl acetate=1:1→1:2) to produce the title compound (80.1 g) having the following physical property value.

TLC: Rf 0.20 (hexane:ethyl acetate=2:3).

Example A: ethyl 2-{(2R,4aR,5S,6R,7aS)-6-(acetoxy)-5-[(3,5-difluorophenoxy)methyl]octahydrocyclopenta[b]pyran-2-yl}-1,3-thiazole-4-carboxylate (Compound A)

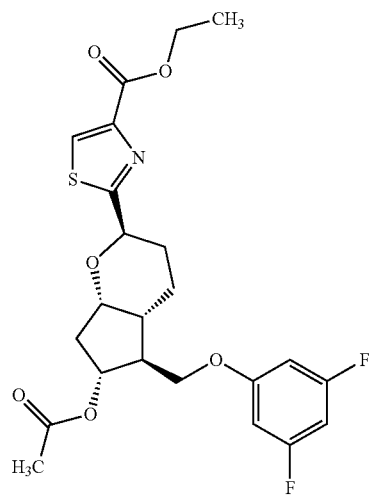 [SMILES: CCOC(=O)c1csc([C@H]2CC[C@@H]3[C@@H](COc4cc(F)cc(F)c4)[C@H](OC(C)=O)C[C@@H]3O2)n1]

Tetrahydrofuran (0.80 mL), N,N,N',N'-tetramethyl azodicarboxamide (28 mg) and 3,5-difluorophenol (14 mg) were added to Reference compound 9 (30 mg), and then tributylphosphine (40 µL) was added dropwise to the mixed solution. The reaction solution was stirred at room temperature overnight. The reaction solution was concentrated under reduced pressure, and the residue was purified by silica gel column chromatography (hexane:ethyl acetate=1:1→1:2) to produce the title compound (31 mg) having the following physical property values.

TLC: Rf 0.74 (hexane:ethyl acetate=1:2);

$^1$H-NMR (CDCl$_3$): δ 1.40, 1.68-1.79, 1.92-2.07, 2.10, 2.15-2.28, 2.36-2.48, 2.50, 4.05, 4.30, 5.18, 6.39-6.44, 8.18.

Example 1: 2-{(2R,4aR,5S,6R,7aS)-5-[(3,5-difluorophenoxy)methyl]-6-hydroxyoctahydrocyclopenta[b]pyran-2-yl}-1,3-thiazole-4-carboxylic acid (Compound 1)

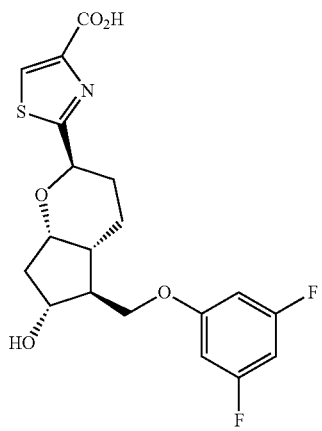 [SMILES: O=C(O)c1csc([C@H]2CC[C@@H]3[C@@H](COc4cc(F)cc(F)c4)[C@H](O)C[C@@H]3O2)n1]

Ethanol (1.0 mL), a 2 M aqueous sodium hydroxide solution (140 μL) were added to Compound A (31 mg), and then stirred at room temperature for 2 hours. AG50W-X8 resin (trade name) (200 mg) was added to the reaction solution, and then stirred at room temperature for 30 minutes. The reaction solution was filtrated through a glass filter, and the filtrate was concentrated under reduced pressure to produce the title compound (31 mg) having the following physical property values.

TLC: Rf 0.40 (dichloromethane:methanol:acetic acid=90:10:1);

$^1$H-NMR (DMSO-d$_6$): δ 1.58-1.94, 2.01-2.24, 3.85, 4.01, 4.05-4.18, 5.07, 6.65-6.80, 8.25.

Examples 1 (1) to 1 (28)

The same procedures as in Example A→Example 1 were carried out except that in place of 3,5-difluorophenol, a corresponding substituted phenol was used. In this manner, the following compounds were produced.

Example 1 (1): 2-[(2R,4aR,5S,6R,7aS)-6-hydroxy-5-{[3-(trifluoromethoxy)phenoxy]methyl}octahydrocyclopenta[b]pyran-2-yl]-1,3-thiazole-4-carboxylic acid (Compound 1-1)

TLC: Rf 0.42 (dichloromethane:methanol:acetic acid=9:1:0.1);

$^1$H-NMR (CDCl$_3$): δ 1.77, 1.87, 2.00-2.11, 2.12-2.22, 2.27, 2.47, 3.96, 4.06, 4.21, 5.22, 6.74, 6.81, 7.27, 8.30.

Example 1 (2): 2-{(2R,4aR,5S,6R,7aS)-5-[(3-fluorophenoxy)methyl]-6-hydroxyoctahydrocyclopenta[b]pyran-2-yl}-1,3-thiazole-4-carboxylic acid (Compound 1-2)

TLC: Rf 0.41 (dichloromethane:methanol:acetic acid=9:1:0.1);

$^1$H-NMR (CDCl$_3$): δ 1.75, 1.88, 1.98-2.20, 2.27, 2.46, 3.95, 4.04, 4.15, 4.22, 5.22, 6.57-6.68, 7.20, 8.30.

Example 1 (3): 2-{(2R,4aR,5S,6R,7aS)-5-[(3,4-difluorophenoxy)methyl]-6-hydroxyoctahydrocyclopenta[b]pyran-2-yl}-1,3-thiazole-4-carboxylic acid (Compound 1-3)

TLC: Rf 0.38 (chloroform:methanol:acetic acid=90:10:1);

$^1$H-NMR (CDCl$_3$): δ 1.66-1.79, 1.81-1.91, 1.97-2.20, 2.25-2.34, 2.41-2.50, 3.91, 4.01, 4.14-4.27, 5.22, 6.58, 6.71, 7.05, 8.32.

Example 1 (4): 2-{(2R,4aR,5S,6R,7aS)-6-hydroxy-5-[(3-methyl-4-nitrophenoxy)methyl]octahydrocyclopenta[b]pyran-2-yl}-1,3-thiazole-4-carboxylic acid (Compound 1-4)

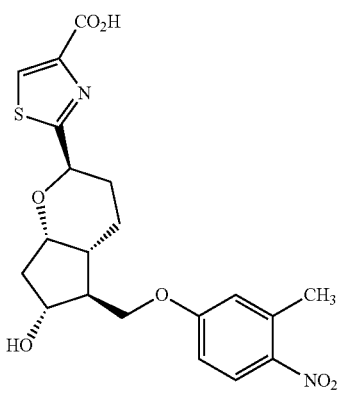 [SMILES: Cc1cc(OC[C@@H]2[C@H]3CC[C@H](c4nc(C(=O)O)cs4)O[C@H]3C[C@H]2O)ccc1[N+](=O)[O-]]

TLC: Rf 0.44 (chloroform:methanol:acetic acid=90:10:1);

$^1$H-NMR (CDCl$_3$): δ 1.65-1.81, 1.83-1.94, 1.97-2.21, 2.25-2.35, 2.44-2.56, 2.63, 4.04, 4.09-4.27, 5.23, 6.78, 6.79, 8.07, 8.32.

Example 1 (5): 2-{(2R,4aR,5S,6R,7aS)-5-[(4-chloro-3-methylphenoxy)methyl]-6-hydroxyoctahydrocyclopenta[b]pyran-2-yl}-1,3-thiazole-4-carboxylic acid (Compound 1-5)

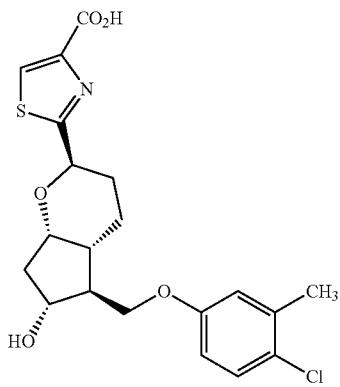 [SMILES: Cc1cc(OC[C@@H]2[C@H]3CC[C@H](c4nc(C(=O)O)cs4)O[C@H]3C[C@H]2O)ccc1Cl]

TLC: Rf 0.41 (dichloromethane:methanol:acetic acid=90:10:1);

$^1$H-NMR (DMSO-$d_6$): δ 1.60-1.94, 2.02-2.23, 2.28, 3.85, 3.94, 4.06, 4.12, 4.89, 5.08, 6.79, 6.95, 7.27, 8.35.

Example 1 (6): 2-{(2R,4aR,5S,6R,7aS)-5-[(2,3-dihydro-1H-inden-5-yloxy)methyl]-6-hydroxyoctahydrocyclopenta[b]pyran-2-yl}-1,3-thiazole-4-carboxylic acid (Compound 1-6)

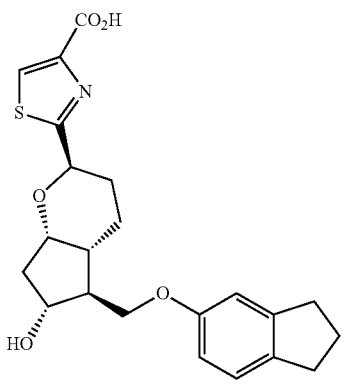 [SMILES: O=C(O)c1csc([C@H]2CC[C@@H]3[C@@H](COc4ccc5c(c4)CCC5)[C@H](O)C[C@@H]3O2)n1]

TLC: Rf 0.42 (dichloromethane:methanol:acetic acid=90:10:1);

$^1$H-NMR (DMSO-$d_6$): δ 1.60-1.94, 1.95-2.23, 2.69-2.84, 3.80-3.96, 4.03, 4.11, 5.06, 6.66, 6.80, 7.07, 8.31.

Example 1 (7): 2-{(2R,4aR,5S,6R,7aS)-5-[(3,4-dimethylphenoxy)methyl]-6-hydroxyoctahydrocyclopenta[b]pyran-2-yl}-1,3-thiazole-4-carboxylic acid (Compound 1-7)

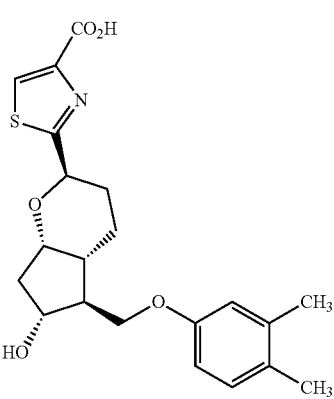

TLC: Rf 0.47 (dichloromethane:methanol:acetic acid=90:10:1);

$^1$H-NMR (DMSO-$d_6$): δ 1.60-1.94, 2.01-2.23, 2.12, 2.16, 3.80-3.95, 4.02, 4.12, 4.89, 5.07, 6.64, 6.73, 7.00, 8.33.

Example 1 (8): 2-{(2R,4aR,5S,6R,7aS)-6-hydroxy-5-[(4-nitrophenoxy)methyl]octahydrocyclopenta[b]pyran-2-yl}-1,3-thiazole-4-carboxylic acid (Compound 1-8)

TLC: Rf 0.37 (dichloromethane:methanol:acetic acid=90:10:1);

$^1$H-NMR (DMSO-$d_6$): δ 1.59-1.95, 2.02-2.25, 3.88, 4.09-4.20, 4.23, 5.05, 7.15, 8.08, 8.19.

Example 1 (9): 2-{(2R,4aR,5S,6R,7aS)-5-[(4-chlorophenoxy)methyl]-6-hydroxyoctahydrocyclopenta[b]pyran-2-yl}-1,3-thiazole-4-carboxylic acid (Compound 1-9)

TLC: Rf 0.37 (dichloromethane:methanol:acetic acid=90:10:1);

$^1$H-NMR (DMSO-$d_6$): δ 1.59-1.94, 2.02-2.25, 3.86, 3.95, 4.07, 4.11, 4.90, 5.08, 6.95, 7.30, 8.40.

Example 1 (10): 2-{(2R,4aR,5S,6R,7aS)-6-hydroxy-5-[(2,3,4-trifluorophenoxy)methyl]octahydrocyclopenta[b]pyran-2-yl}-1,3-thiazole-4-carboxylic acid (Compound 1-10)

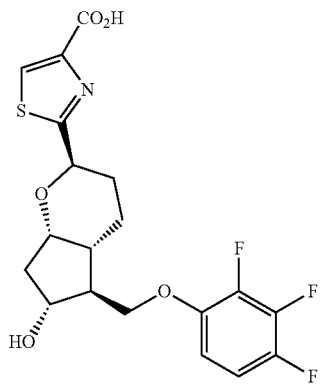 [SMILES: O=C(O)c1csc([C@H]2CC[C@@H]3[C@@H](COc4ccc(F)c(F)c4F)[C@H](O)C[C@@H]3O2)n1]

TLC: Rf 0.43 (dichloromethane:methanol:acetic acid=90:10:1);
$^1$H-NMR (DMSO-$d_6$): δ 1.59-1.96, 2.02-2.25, 3.86, 4.06, 4.10, 4.19, 5.06, 6.99-7.10, 7.19-7.32, 8.20.

Example 1 (11): 2-{(2R,4aR,5S,6R,7aS)-5-[(4-cyano-3-methylphenoxy)methyl]-6-hydroxyoctahydrocyclopenta[b]pyran-2-yl}-1,3-thiazole-4-carboxylic acid (Compound 1-11)

TLC: Rf 0.04 (hexane:ethyl acetate=2:1);
$^1$H-NMR (CDCl$_3$): δ 1.28, 1.74, 1.87, 2.01, 2.06-2.19, 2.29, 2.47, 2.50, 4.00, 4.07, 4.20, 4.23, 5.22, 6.75, 6.79, 7.50, 8.32.

Example 1 (12): 2-{(2R,4aR,5S,6R,7aS)-6-hydroxy-5-[(1H-indol-5-yloxy)methyl]octahydrocyclopenta[b]pyran-2-yl}-1,3-thiazole-4-carboxylic acid (Compound 1-12)

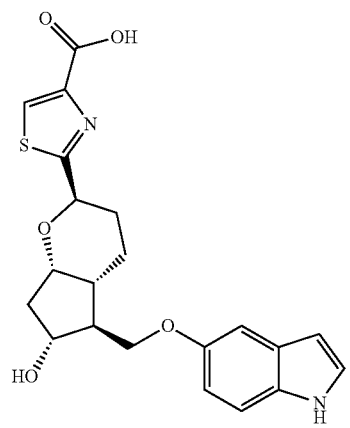 [SMILES: O=C(O)c1csc([C@H]2CC[C@@H]3[C@@H](COc4ccc5[nH]ccc5c4)[C@H](O)C[C@@H]3O2)n1]

TLC: Rf 0.26 (chloroform:methanol:acetic acid=9:1:0.1);
$^1$H-NMR (CDCl$_3$): δ 1.76, 1.92, 1.98-2.12, 2.16-2.37, 2.48, 3.99, 4.13, 4.24, 5.21, 6.46, 6.83, 7.10, 7.18, 7.30, 8.06, 8.30.

Example 1 (13): 2-{(2R,4aR,5S,6R,7aS)-5-[(2,3-dihydro-1H-inden-4-yloxy)methyl]-6-hydroxyoctahydrocyclopenta[b]pyran-2-yl}-1,3-thiazole-4-carboxylic acid (Compound 1-13)

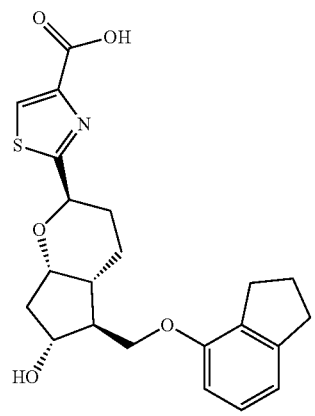 [SMILES: O=C(O)c1csc([C@H]2CC[C@@H]3[C@@H](COc4cccc5c4CCC5)[C@H](O)C[C@@H]3O2)n1]

TLC: Rf 0.50 (chloroform:methanol:acetic acid=9:1:0.1);
$^1$H-NMR (CDCl$_3$): δ 1.77, 1.90, 1.98-2.10, 2.12-2.21, 2.28, 2.47, 2.82, 2.91, 3.99, 4.09, 4.23, 5.21, 6.64, 6.85, 7.10, 8.30.

Example 1 (14): 2-{(2R,4aR,5S,6R,7aS)-5-[(4-ethyl-3-methylphenoxy)methyl]-6-hydroxyoctahydrocyclopenta[b]pyran-2-yl}-1,3-thiazole-4-carboxylic acid (Compound 1-14)

TLC: Rf 0.70 (dichloromethane:methanol=4:1);
$^1$H-NMR (CDCl$_3$): δ 1.16, 1.74, 1.86, 1.99, 2.12, 2.12-2.21, 2.27, 2.27-2.32, 2.44, 2.56, 3.92, 4.05, 4.16-4.22, 5.20, 6.67, 6.69, 7.04, 8.29.

Example 1 (15): 2-{(2R,4aR,5S,6R,7aS)-5-[(bicyclo[4.2.0]octa-1,3,5-trien-3-yloxy)methyl]-6-hydroxyoctahydrocyclopenta[b]pyran-2-yl}-1,3-thiazole-4-carboxylic acid (Compound 1-15)

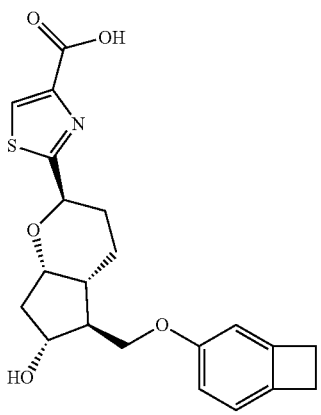 [SMILES: O=C(O)c1csc([C@H]2CC[C@@H]3[C@@H](COc4ccc5c(c4)CC5)[C@H](O)C[C@@H]3O2)n1]

TLC: Rf 0.45 (chloroform:methanol:acetic acid=9:1:0.1);
$^1$H-NMR (CDCl$_3$): δ 1.73, 1.88, 1.98, 2.22, 2.28, 2.44, 3.10, 3.91, 4.04, 4.23, 5.21, 6.65, 6.72, 6.93, 8.32.

Example 1 (16): 2-{(2R,4aR,5S,6R,7aS)-5-[(1-benzofuran-6-yloxy)methyl]-6-hydroxyoctahydrocyclopenta[b]pyran-2-yl}-1,3-thiazole-4-carboxylic acid (Compound 1-16)

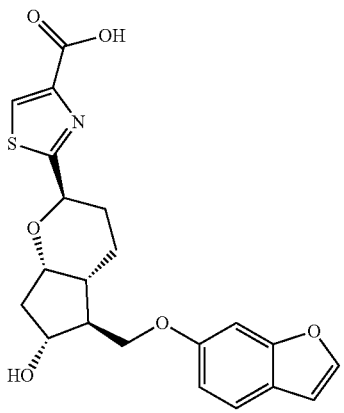 [SMILES: O=C(O)c1csc([C@H]2CC[C@@H]3[C@@H](COc4ccc5ccoc5c4)[C@H](O)C[C@@H]3O2)n1]

TLC: Rf 0.41 (chloroform:methanol:acetic acid=9:1:0.1);
$^1$H-NMR (CDCl$_3$): δ 1.76, 1.92, 2.02, 2.08-2.23, 2.30, 2.49, 3.99, 4.11, 4.24, 5.22, 6.68, 6.85, 7.02, 7.43, 7.52, 8.31.

Example 1 (17): 2-{(2R,4aR,5S,6R,7aS)-5-[(3-ethyl-4-methylphenoxy)methyl]-6-hydroxyoctahydrocyclopenta[b]pyran-2-yl}-1,3-thiazole-4-carboxylic acid (Compound 1-17)

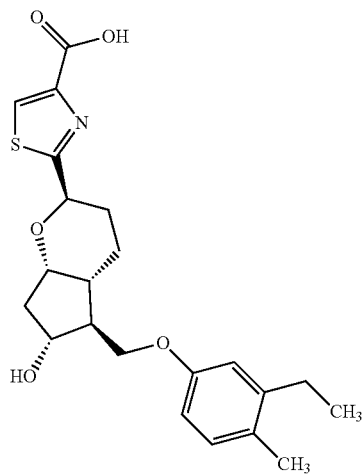 [SMILES: CCc1cc(OC[C@@H]2[C@H]3CC[C@H](c4nc(C(=O)O)cs4)O[C@H]3C[C@H]2O)ccc1C]

TLC: Rf 0.68 (dichloromethane:methanol=4:1);
$^1$H-NMR (CDCl$_3$): δ 1.20, 1.79, 1.89, 1.95-2.08, 2.12-2.32, 2.23, 2.44, 2.58, 3.92, 4.07, 4.17, 4.24, 5.21, 6.62, 6.71, 7.02, 8.30.

Example 1 (18): 2-[(2R,4aR,5S,6R,7aS)-5-{[(4-chloro-2,3-dihydro-1H-inden-5-yl)oxy]methyl}-6-hydroxyoctahydrocyclopenta[b]pyran-2-yl]-1,3-thiazole-4-carboxylic acid (Compound 1-18)

TLC: Rf 0.59 (dichloromethane:methanol=4:1);
$^1$H-NMR (CDCl$_3$): δ 1.76, 1.93, 2.01-2.16, 2.24-2.33, 2.50, 2.92, 3.95, 4.20, 4.25, 5.21, 6.70, 7.02, 8.30.

Example 1 (19): 2-[(2R,4aR,5S,6R,7aS)-5-{[(4-fluoro-2,3-dihydro-1H-inden-5-yl)oxy]methyl}-6-hydroxyoctahydrocyclopenta[b]pyran-2-yl]-1,3-thiazole-4-carboxylic acid (Compound 1-19)

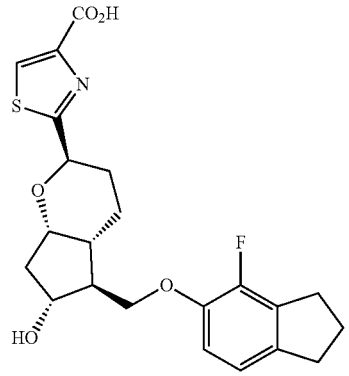 [SMILES: O=C(O)c1csc([C@H]2CC[C@@H]3[C@@H](COc4ccc5c(c4F)CCC5)[C@H](O)C[C@@H]3O2)n1]

TLC: Rf 0.19 (dichloromethane:methanol:water=90:10:1);
$^1$H-NMR (DMSO-d$_6$): δ 1.60-1.95, 1.99-2.22, 2.78-2.90, 3.86, 3.96, 4.08-4.18, 4.28, 4.90, 5.08, 6.88-6.98, 8.42.

Example 1 (20): 2-[(2R,4aR,5S,6R,7aS)-6-hydroxy-5-{[(4-methyl-2,3-dihydro-1H-inden-5-yl)oxy]methyl}octahydrocyclopenta[b]pyran-2-yl]-1,3-thiazole-4-carboxylic acid (Compound 1-20)

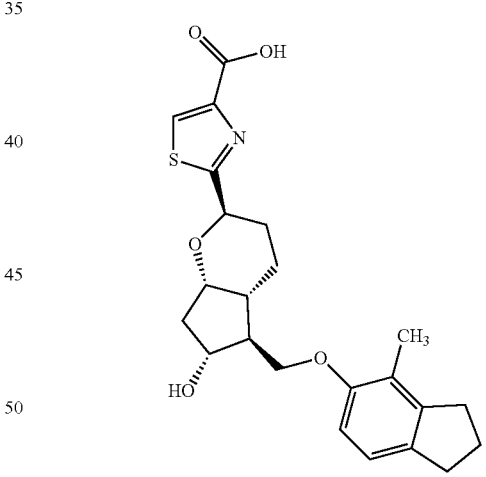

TLC: Rf 0.44 (dichloromethane:methanol=4:1);
$^1$H-NMR (CDCl$_3$): δ 1.76, 1.95, 1.96-2.22, 2.11, 2.29, 2.47, 2.84, 3.94, 4.06, 4.23, 5.22, 6.64, 6.98, 8.31.

Example 1 (21): 2-[(2R,4aR,5S,6R,7aS)-6-hydroxy-5-{[(6-methyl-2,3-dihydro-1H-inden-5-yl)oxy]methyl}octahydrocyclopenta[b]pyran-2-yl]-1,3-thiazole-4-carboxylic acid (Compound 1-21)

TLC: Rf 0.44 (dichloromethane:methanol=4:1);
$^1$H-NMR (CDCl$_3$): δ 1.77, 1.95, 1.96-2.22, 2.15, 2.29, 2.47, 2.83, 3.95, 4.07, 4.22, 5.22, 6.72, 6.98, 8.30.

Example 1 (22): 2-{(2R,4aR,5S,6R,7aS)-5-[(4-chloro-3-cyclopropylphenoxy)methyl]-6-hydroxyoctahydrocyclopenta[b]pyran-2-yl}-1,3-thiazole-4-carboxylic acid (Compound 1-22)

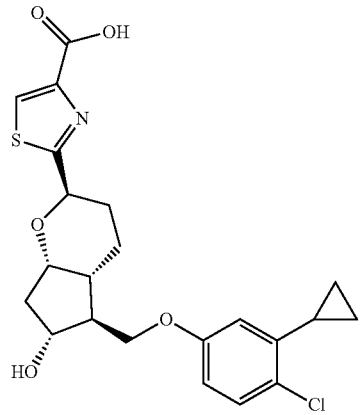 [SMILES: O=C(O)c1csc([C@H]2CC[C@@H]3[C@@H](COc4ccc(Cl)c(C5CC5)c4)[C@H](O)C[C@@H]3O2)n1]

TLC: Rf 0.42 (chloroform:methanol:acetic acid=9:1:0.1);
$^1$H-NMR (CDCl$_3$): δ 0.66, 1.01, 1.73, 1.85, 1.98, 2.15, 2.28, 2.43, 3.89, 4.01, 4.18, 4.22, 5.21, 6.44, 6.62, 7.22, 8.31.

Example 1 (23): 2-{(2R,4aR,5S,6R,7aS)-5-[(4-ethyl-3-fluorophenoxy)methyl]-6-hydroxyoctahydrocyclopenta[b]pyran-2-yl}-1,3-thiazole-4-carboxylic acid (Compound 1-23)

TLC: Rf 0.45 (dichloromethane:methanol=10:1) COOH Silica plate;
$^1$H-NMR (CDCl$_3$): δ 1.19, 1.74, 1.87, 1.99, 2.02-2.20, 2.27, 2.45, 3.92, 4.04, 4.19, 4.22, 5.21, 6.57, 6.60, 7.07, 8.30.

Example 1 (24): 2-{(2R,4aR,5S,6R,7aS)-5-[(3-cyclopropyl-4-ethylphenoxy)methyl]-6-hydroxyoctahydrocyclopenta[b]pyran-2-yl}-1,3-thiazole-4-carboxylic acid (Compound 1-24)

TLC: Rf 0.28 (dichloromethane:methanol=10:1) COOH Silica plate;
$^1$H-NMR (CDCl$_3$): δ 0.64, 0.93, 1.23, 1.49-2.36, 2.39-2.48, 2.75, 3.90, 4.03, 4.20, 5.20, 6.49, 6.65, 7.05, 8.29.

Example 1 (25): 2-[(2R,4aR,5S,6R,7aS)-6-hydroxy-5-{[4-(methoxymethyl)-3-methylphenoxy]methyl}octahydrocyclopenta[b]pyran-2-yl]-1,3-thiazole-4-carboxylic acid (Compound 1-25)

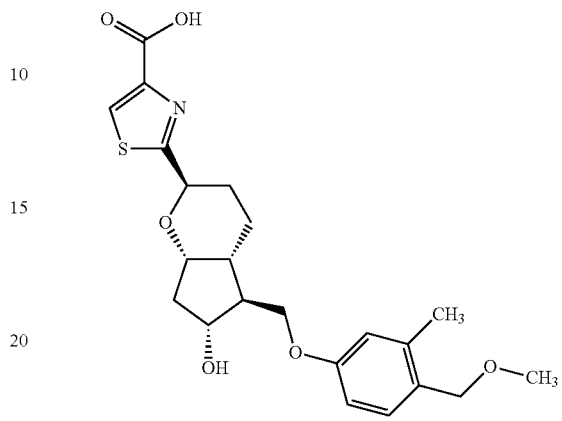

TLC: Rf 0.48 (dichloromethane:methanol=10:1) COOH Silica plate;
$^1$H-NMR (CDCl$_3$): δ 1.60-2.29, 2.32, 2.39-2.50, 3.36, 3.94, 4.06, 4.14-4.25, 4.38, 5.20, 6.68, 6.72, 7.18, 8.29.

Example 1 (26): 2-{(2R,4aR,5S,6R,7aS)-5-[(4-ethyl-3-propylphenoxy)methyl]-6-hydroxyoctahydrocyclopenta[b]pyran-2-yl}-1,3-thiazole-4-carboxylic acid (Compound 1-26)

TLC: Rf 0.48 (dichloromethane:methanol=10:1) COOH Silica plate;
$^1$H-NMR (CDCl$_3$): δ 0.99, 1.18, 1.50-2.38, 2.39-2.49, 2.50-2.61, 3.92, 4.05, 4.14-4.24, 5.20, 6.62-6.70, 7.05, 8.29.

Example 1 (27): 2-[(2R,4aR,5S,6R,7aS)-6-hydroxy-5-(phenoxymethyl)octahydrocyclopenta[b]pyran-2-yl]-1,3-thiazole-4-carboxylic acid (Compound 1-27)

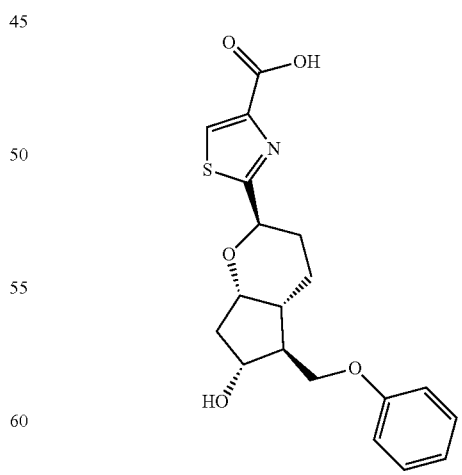

TLC: Rf 0.29 (dichloromethane:methanol:water=70:10:1);
$^1$H-NMR (CDCl$_3$): δ 1.75, 1.92, 2.00, 2.17, 2.27, 2.44, 3.96, 4.09, 4.23, 5.22, 6.88, 6.96, 7.29, 8.32.

Example 1 (28): 2-{(2R,4aR,5S,6R,7aS)-5-[(3,5-dichlorophenoxy)methyl]-6-hydroxyoctahydrocyclopenta[b]pyran-2-yl}-1,3-thiazole-4-carboxylic acid (Compound 1-28)

TLC: Rf 0.29 (dichloromethane:methanol:water=70:10:1);
$^1$H-NMR (CDCl$_3$): δ 1.72, 1.85, 2.00, 2.03-2.14, 2.27, 2.45, 3.95, 4.03, 4.17, 4.23, 5.22, 6.80, 6.96, 8.30.

Example 2: (2R,4aR,5S,6R,7aS)-5-[(3,5-difluorophenoxy)methyl]-2-[4-(hydroxymethyl)-1,3-thiazol-2-yl]octahydrocyclopenta[b]pyran-6-ol (Compound 2)

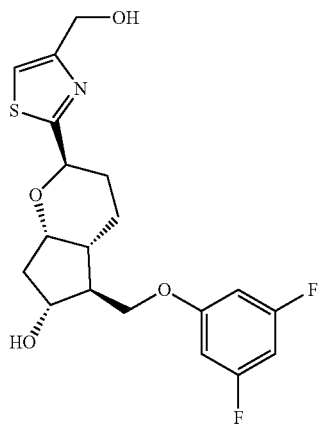 [SMILES: OCc1csc([C@H]2CC[C@@H]3[C@@H](COc4cc(F)cc(F)c4)[C@H](O)C[C@@H]3O2)n1]

Tetrahydrofuran (1.0 mL) and lithium borohydride (12 mg) were added to Compound A (20 mg) and then stirred at 50° C. for 17 hours. A 1 M aqueous hydrochloric acid solution was added to the reaction solution, and the reaction solution was extracted with ethyl acetate. The organic layer was washed with water and saturated brine, then dried over anhydrous sodium sulfate, and then filtrated. The filtrate was concentrated under reduced pressure, and the residue was purified by silica gel column chromatography (hexane:ethyl acetate=1:1→0:100) to produce the title compound (8.2 mg) having the following physical property values.

TLC: Rf 0.46 (ethyl acetate);
$^1$H-NMR (CDCl$_3$): δ 1.69, 1.82, 2.00, 2.09, 2.20, 2.24, 2.46, 2.70, 3.93, 4.04, 4.17, 4.27, 4.77, 5.21, 6.37-6.45, 7.22.

Examples 2 (1) to 2 (21)

The same procedures as in Example A→Example 2 were carried out except that in place of 3,5-difluorophenol, a corresponding substituted phenol was used. In this manner, the following compounds were produced.

Example 2 (1): (2R,4aR,5S,6R,7aS)-2-[4-(hydroxymethyl)-1,3-thiazol-2-yl]-5-(phenoxymethyl)octahydrocyclopenta[b]pyran-6-ol (Compound 2-1)

TLC: Rf 0.23 (hexane:ethyl acetate=1:4);
$^1$H-NMR (CDCl$_3$): δ 1.69-1.77, 1.83-1.89, 1.96-2.16, 2.19-2.29, 2.47, 3.95, 4.08, 4.17, 4.27, 4.77, 5.19, 6.87, 6.94, 7.20, 7.28.

Example 2 (2): (2R,4aR,5S,6R,7aS)-5-[(3,5-dichlorophenoxy)methyl]-2-[4-(hydroxymethyl)-1,3-thiazol-2-yl]octahydrocyclopenta[b]pyran-6-ol (Compound 2-2)

TLC: Rf 0.21 (hexane:ethyl acetate=1:4);
$^1$H-NMR (CDCl$_3$): δ 1.67-1.72, 1.73-1.85, 1.97-2.14, 2.22-2.28, 2.46, 3.93, 4.03, 4.14, 4.26, 4.77, 5.19, 6.79, 6.95, 7.21.

Example 2 (3): (2R,4aR,5S,6R,7aS)-2-[4-(hydroxymethyl)-1,3-thiazol-2-yl]-5-[(3-methyl-4-nitrophenoxy)methyl]octahydrocyclopenta[b]pyran-6-ol (Compound 2-3)

TLC: Rf 0.19 (ethyl acetate);
$^1$H-NMR (DMSO-d$_6$): δ 1.62-1.87, 2.05-2.26, 2.54, 3.87, 4.14, 4.21, 4.53, 5.03, 5.28, 6.97, 7.03, 8.04.

Example 2 (4): (2R,4aR,5S,6R,7aS)-5-[(2,3-dihydro-1H-inden-5-yloxy)methyl]-2-[4-(hydroxymethyl)-1,3-thiazol-2-yl]octahydrocyclopenta[b]pyran-6-ol (Compound 2-4)

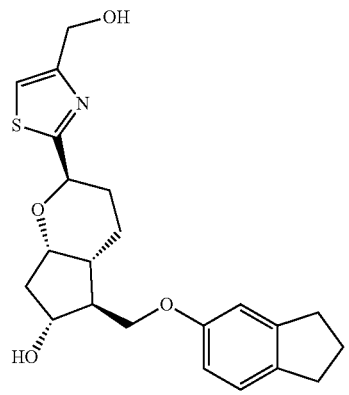 [SMILES: OCc1csc([C@H]2CC[C@@H]3[C@@H](COc4ccc5c(c4)CCC5)[C@H](O)C[C@@H]3O2)n1]

TLC: Rf 0.18 (hexane:ethyl acetate=2:8);
$^1$H-NMR (CDCl$_3$): δ 1.64-1.78, 1.80-1.88, 1.94-2.18, 2.19-2.35, 2.79-2.90, 3.91, 4.04, 4.16, 4.25, 4.76, 5.18, 6.66, 6.77, 7.09, 7.20.

Example 2 (5): (2R,4aR,5S,6R,7aS)-2-[4-(hydroxymethyl)-1,3-thiazol-2-yl]-5-[(1H-indol-5-yloxy)methyl]octahydrocyclopenta[b]pyran-6-ol (Compound 2-5)

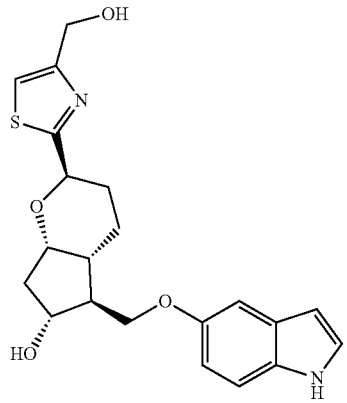 [SMILES: OCc1csc([C@H]2CC[C@@H]3[C@@H](COc4ccc5[nH]ccc5c4)[C@H](O)C[C@@H]3O2)n1]

TLC: Rf 0.21 (hexane:ethyl acetate=1:2);
$^1$H-NMR (CDCl$_3$): δ 1.73, 1.88, 2.00, 2.06-2.26, 2.49, 2.79, 3.98, 4.12, 4.22, 4.28, 4.77, 5.19, 6.46, 6.83, 7.10, 7.19, 7.27, 8.05.

Example 2 (6): (2R,4aR,5S,6R,7aS)-5-[(4-ethyl-3-methylphenoxy)methyl]-2-[4-(hydroxymethyl)-1,3-thiazol-2-yl]octahydrocyclopenta[b]pyran-6-ol (Compound 2-6)

TLC: Rf 0.21 (hexane:ethyl acetate=1:2);
$^1$H-NMR (CDCl$_3$): δ 1.17, 1.71, 1.83, 1.97, 2.06-2.15, 2.23, 2.27, 2.45, 2.55, 2.74, 3.90, 4.04, 4.15, 4.26, 4.76, 5.19, 6.67, 6.68, 7.03, 7.19.

Example 2 (7): (2R,4aR,5S,6R,7aS)-5-[(bicyclo[4.2.0]octa-1,3,5-trien-3-yloxy)methyl]-2-[4-(hydroxymethyl)-1,3-thiazol-2-yl]octahydrocyclopenta[b]pyran-6-ol (Compound 2-7)

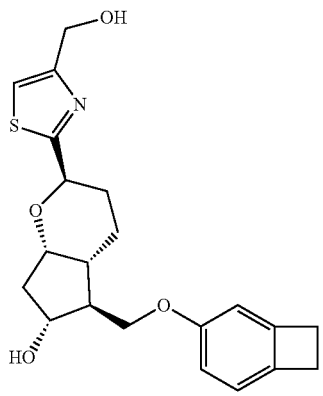 [SMILES: OCc1csc([C@H]2CC[C@@H]3[C@@H](COc4ccc5c(c4)CC5)[C@H](O)C[C@@H]3O2)n1]

TLC: Rf 0.48 (ethyl acetate);
$^1$H-NMR (CDCl$_3$): δ 1.71, 1.84, 1.98, 2.11-2.16, 2.25, 2.45, 3.10, 3.90, 4.03, 4.17, 4.26, 5.19, 6.65, 6.71, 6.93, 7.21.

Example 2 (8): (2R,4aR,5S,6R,7aS)-5-[(1-benzofuran-6-yloxy)methyl]-2-[4-(hydroxymethyl)-1,3-thiazol-2-yl]octahydrocyclopenta[b]pyran-6-ol (Compound 2-8)

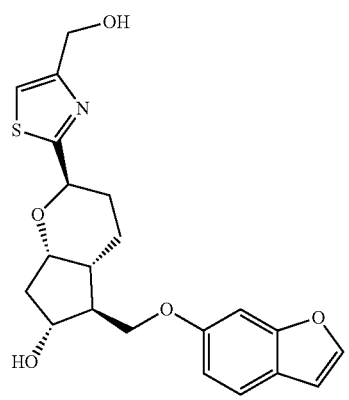 [SMILES: OCc1csc([C@H]2CC[C@@H]3[C@@H](COc4ccc5ccoc5c4)[C@H](O)C[C@@H]3O2)n1]

TLC: Rf 0.46 (ethyl acetate);
$^1$H-NMR (CDCl$_3$): δ 1.74, 1.86, 1.99, 2.06-2.17, 2.25, 2.49, 3.99, 4.10, 4.20, 4.28, 4.77, 5.20, 6.68, 6.85, 7.02, 7.20, 7.43, 7.52.

Example 2 (9): (2R,4aR,5S,6R,7aS)-5-[(3-ethyl-4-methylphenoxy)methyl]-2-[4-(hydroxymethyl)-1,3-thiazol-2-yl]octahydrocyclopenta[b]pyran-6-ol (Compound 2-9)

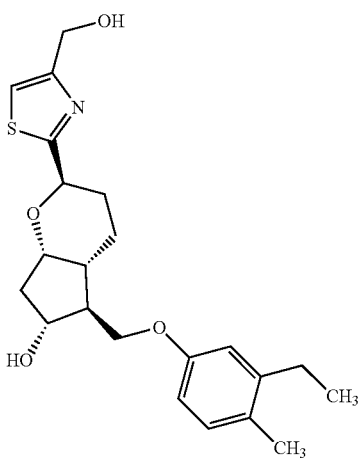 [SMILES: CCc1cc(OC[C@@H]2[C@H]3CC[C@H](c4nc(CO)cs4)O[C@H]3C[C@H]2O)ccc1C]

TLC: Rf 0.19 (hexane:ethyl acetate=1:3);
$^1$H-NMR (CDCl$_3$): δ 1.20, 1.71, 1.84, 1.98, 2.04-2.28, 2.22, 2.45, 2.58, 3.91, 4.04, 4.17, 4.26, 4.77, 5.19, 6.62, 6.70, 7.02, 7.20.

Example 2 (10): (2R,4aR,5S,6R,7aS)-5-[(4-chloro-3-cyclopropylphenoxy)methyl]-2-[4-(hydroxymethyl)-1,3-thiazol-2-yl]octahydrocyclopenta[b]pyran-6-ol (Compound 2-10)

TLC: Rf 0.41 (ethyl acetate);

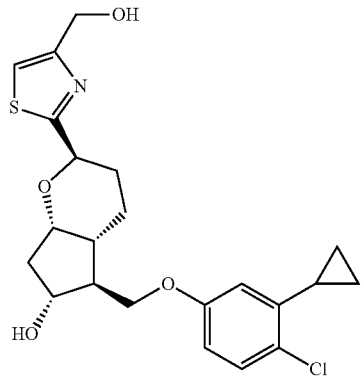 [SMILES: OCc1csc([C@H]2CC[C@@H]3[C@@H](COc4ccc(Cl)c(C5CC5)c4)[C@H](O)C[C@@H]3O2)n1]

$^1$H-NMR (CDCl$_3$): δ 0.66, 1.01, 1.70, 1.81, 1.98, 2.05-2.19, 2.23, 2.44, 2.70, 3.88, 4.00, 4.15, 4.25, 4.76, 5.19, 6.43, 6.62, 7.20, 7.22.

Example 2 (11): (2R,4aR,5S,6R,7aS)-5-[(3-cyclopropyl-4-ethylphenoxy)methyl]-2-[4-(hydroxymethyl)-1,3-thiazol-2-yl]octahydrocyclopenta[b]pyran-6-ol (Compound 2-11)

TLC: Rf 0.71 (ethyl acetate);
$^1$H-NMR (CDCl$_3$): δ 0.64, 0.93, 1.22, 1.62-2.30, 2.38-2.47, 2.76, 3.88, 4.03, 4.16, 4.25, 4.76, 5.18, 6.49, 6.65, 7.04, 7.20.

Example 2 (12): (2R,4aR,5S,6R,7aS)-5-[(3,4-dimethylphenoxy)methyl]-2-[4-(hydroxymethyl)-1,3-thiazol-2-yl]octahydrocyclopenta[b]pyran-6-ol (Compound 2-12)

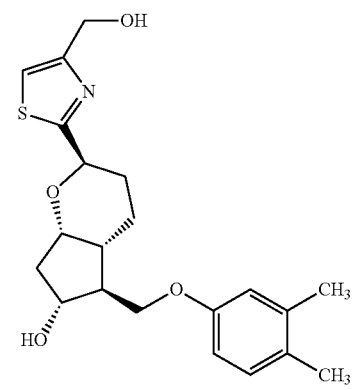 [SMILES: Cc1ccc(OC[C@@H]2[C@H]3CC[C@H](c4nc(CO)cs4)O[C@H]3C[C@H]2O)cc1C]

TLC: Rf 0.24 (hexane:ethyl acetate=2:8);
$^1$H-NMR (CDCl$_3$): δ 1.64-1.78, 1.79-1.88, 1.93-2.34, 1.99, 2.22, 2.39-2.50, 2.73, 3.91, 4.04, 4.13-4.22, 4.26, 4.77, 5.19, 6.63, 6.70, 7.02, 7.21.

Example 2 (13): (2R,4aR,5S,6R,7aS)-5-[(4-chloro-3-methylphenoxy)methyl]-2-[4-(hydroxymethyl)-1,3-thiazol-2-yl]octahydrocyclopenta[b]pyran-6-ol (Compound 2-13)

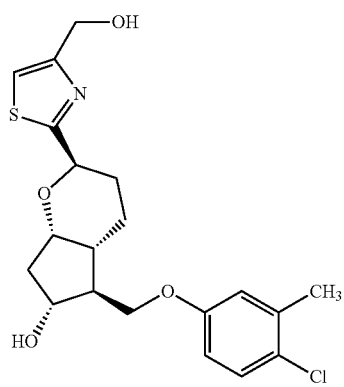 [SMILES: Cc1cc(OC[C@@H]2[C@H]3CC[C@H](c4nc(CO)cs4)O[C@H]3C[C@H]2O)ccc1Cl]

TLC: Rf 0.21 (hexane:ethyl acetate=2:8);
$^1$H-NMR (CDCl$_3$): δ 1.64-1.78, 1.79-1.87, 1.93-2.10, 2.13, 2.39-2.50, 2.72, 3.91, 4.02, 4.10-4.21, 4.26, 4.77, 5.19, 6.66, 6.76, 7.21, 7.21.

Example 2 (14): (2R,4aR,5S,6R,7aS)-5-[(2,3-dihydro-1H-inden-4-yloxy)methyl]-2-[4-(hydroxymethyl)-1,3-thiazol-2-yl]octahydrocyclopenta[b]pyran-6-ol (Compound 2-14)

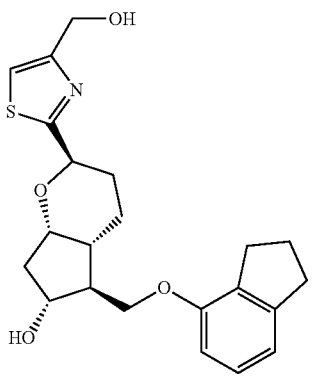 [SMILES: OCc1csc([C@H]2CC[C@@H]3[C@@H](COc4cccc5c4CCC5)[C@H](O)C[C@@H]3O2)n1]

TLC: Rf 0.48 (ethyl acetate);
$^1$H-NMR (CDCl$_3$): δ 1.74, 1.87, 1.99, 2.02-2.16, 2.26, 2.82, 2.91, 3.99, 4.09, 4.18, 4.27, 5.20, 6.64, 6.84, 7.10, 7.20.

Example 2 (15): (2R,4aR,5S,6R,7aS)-5-{[(4-chloro-2,3-dihydro-1H-inden-5-yl)oxy]methyl}-2-[4-(hydroxymethyl)-1,3-thiazol-2-yl]octahydrocyclopenta[b]pyran-6-ol (Compound 2-15)

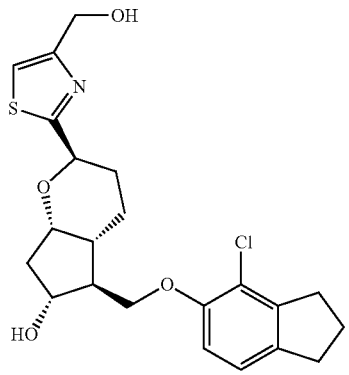 [SMILES: OCc1csc([C@H]2CC[C@@H]3[C@@H](COc4ccc5c(c4Cl)CCC5)[C@H](O)C[C@@H]3O2)n1]

TLC: Rf 0.40 (ethyl acetate);
$^1$H-NMR (CDCl$_3$): δ 1.76, 1.94, 1.98, 2.00-2.14, 2.19-2.28, 2.50, 2.92, 3.95, 4.10-4.22, 4.28, 4.76, 5.19, 6.70, 7.01, 7.20.

Example 2 (16): (2R,4aR,5S,6R,7aS)-5-{[(4-fluoro-2,3-dihydro-1H-inden-5-yl)oxy]methyl}-2-[4-(hydroxymethyl)-1,3-thiazol-2-yl]octahydrocyclopenta[b]pyran-6-ol (Compound 2-16)

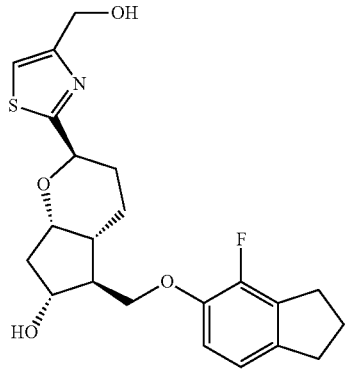 [SMILES: OCc1csc([C@H]2CC[C@@H]3[C@@H](COc4ccc5c(c4F)CCC5)[C@H](O)C[C@@H]3O2)n1]

TLC: Rf 0.35 (ethyl acetate);
$^1$H-NMR (CDCl$_3$): δ 1.64-1.79, 1.82-1.93, 1.94-2.35, 2.42-2.54, 2.78-2.95, 3.98, 4.08-4.29, 4.77, 5.18, 6.76, 6.87, 7.21.

Example 2 (17): (2R,4aR,5S,6R,7aS)-2-[4-(hydroxymethyl)-1,3-thiazol-2-yl]-5-{[(4-methyl-2,3-dihydro-1H-inden-5-yl)oxy]methyl}octahydrocyclopenta[b]pyran-6-ol (Compound 2-17)

TLC: Rf 0.23 (hexane:ethyl acetate=1:3);
$^1$H-NMR (CDCl$_3$): δ 1.75, 1.93, 1.97-2.17, 2.10, 2.26, 2.49, 2.84, 3.93, 4.06, 4.21, 4.28, 4.77, 5.20, 6.64, 6.98, 7.20.

Example 2 (18): (2R,4aR,5S,6R,7aS)-5-[(4-ethyl-3-fluorophenoxy)methyl]-2-[4-(hydroxymethyl)-1,3-thiazol-2-yl]octahydrocyclopenta[b]pyran-6-ol (Compound 2-18)

TLC: Rf 0.23 (ethyl acetate:hexane=2:1);
$^1$H-NMR (CDCl$_3$): δ 1.19, 1.74, 1.83, 1.99, 2.04-2.14, 2.24, 2.45, 2.57, 2.72, 3.91, 4.02, 4.15, 4.26, 4.77, 5.19, 6.57, 6.60, 7.06, 7.20.

Example 2 (19): (2R,4aR,5S,6R,7aS)-5-[(3,4-difluorophenoxy)methyl]-2-[4-(hydroxymethyl)-1,3-thiazol-2-yl]octahydrocyclopenta[b]pyran-6-ol (Compound 2-19)

TLC: Rf 0.15 (ethyl acetate:hexane=2:1);
$^1$H-NMR (CDCl$_3$): δ 1.71, 1.82, 1.98, 2.04-2.17, 2.25, 2.46, 2.70, 3.90, 4.00, 4.13, 4.26, 4.76, 5.19, 6.57, 6.70, 7.05, 7.21.

Example 2 (20): (2R,4aR,5S,6R,7aS)-2-[4-(hydroxymethyl)-1,3-thiazol-2-yl]-5-{[4-(methoxymethyl)-3-methylphenoxy]methyl}octahydrocyclopenta[b]pyran-6-ol (Compound 2-20)

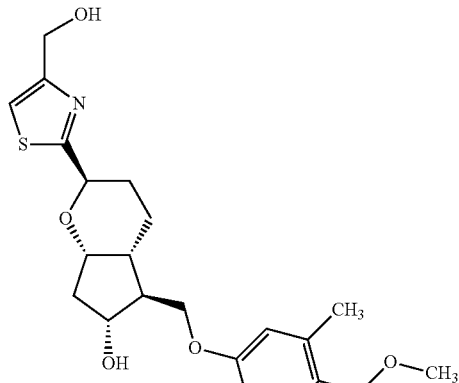

TLC: Rf 0.55 (ethyl acetate);
$^1$H-NMR (CDCl$_3$): δ 1.62-1.78, 1.79-1.87, 1.95-2.27, 2.31, 2.40-2.50, 2.74, 3.35, 3.93, 4.05, 4.16, 4.26, 4.38, 4.76, 5.19, 6.68, 6.71, 7.18, 7.20.

Example 2 (21): (2R,4aR,5S,6R,7aS)-5-[(4-ethyl-3-propylphenoxy)methyl]-2-[4-(hydroxymethyl)-1,3-thiazol-2-yl]octahydrocyclopenta[b]pyran-6-ol (Compound 2-21)

TLC: Rf 0.67 (ethyl acetate);
$^1$H-NMR (CDCl$_3$): δ 0.99, 1.18, 1.50-1.79, 1.80-1.89, 1.94-2.29, 2.39-2.49, 2.50-2.62, 2.74, 3.91, 4.04, 4.17, 4.27, 4.77, 5.19, 6.62-6.70, 7.05, 7.20.

Example 3: isopropyl 2-{(2R,4aR,5S,6R,7aS)-6-hydroxy-5-[(4-nitrophenoxy)methyl]octahydrocyclopenta[b]pyran-2-yl}-1,3-thiazole-4-carboxylate (Compound 3)

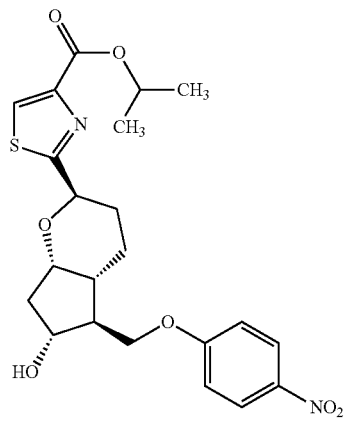 [SMILES: CC(C)OC(=O)c1csc([C@H]2CC[C@@H]3[C@@H](COc4ccc([N+](=O)[O-])cc4)[C@H](O)C[C@@H]3O2)n1]

N,N-Dimethylformamide (1.0 mL), potassium carbonate (70 mg) and 2-iodopropane (30 μL) were added to 2-{(2R,4aR,5S,6R,7aS)-6-hydroxy-5-[(4-nitrophenoxy)methyl]octahydrocyclopenta[b]pyran-2-yl}-1,3-thiazole-4-carboxylic acid (20 mg) that was produced by carrying out the same procedures as in Example A→Example 1 except that 4-nitrophenol was used in place of 3,5-difluorophenol. The resulting solution was stirred at room temperature overnight. The reaction solution was filtrated, and then washed with N,N-dimethylformamide (1.0 mL). A 1 M aqueous hydrochloric acid solution (40 μL) was added to the filtrate thus produced, and then the solution was concentrated under reduced pressure. The residue was purified by silica gel column chromatography (hexane:ethyl acetate=9:1→1:4) to produce the title compound (11 mg) having the following physical property values.

TLC: Rf 0.58 (hexane:ethyl acetate=1:3);
$^1$H-NMR (CDCl$_3$): δ 1.38, 1.71, 1.86, 2.00-2.17, 2.21-2.40, 2.50, 2.59, 4.06, 4.15, 4.16, 4.26, 5.22, 5.27, 6.95, 8.14, 8.19.

Examples 3 (1) to 3 (12)

The same procedure as in Example 3 was carried out except that in place of 4-nitrophenol, a corresponding substituted phenol was used. In this manner, the following compounds were produced.

Example 3 (1): isopropyl 2-[(2R,4aR,5S,6R,7aS)-6-hydroxy-5-(phenoxymethyl)octahydrocyclopenta[b]pyran-2-yl]-1,3-thiazole-4-carboxylate (Compound 3-1)

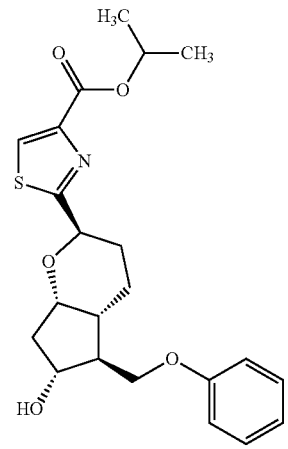 [SMILES: CC(C)OC(=O)c1csc([C@H]2CC[C@@H]3[C@@H](COc4ccccc4)[C@H](O)C[C@@H]3O2)n1]

TLC: Rf 0.58 (hexane:ethyl acetate=1:4);
$^1$H-NMR (CDCl$_3$): δ 1.38, 1.68-1.76, 1.88, 1.96-2.20, 2.28, 2.46, 2.64, 3.94, 4.07, 4.14, 4.26, 5.22, 5.27, 6.88, 6.94, 7.28, 8.14.

Example 3 (2): isopropyl 2-{(2R,4aR,5S,6R,7aS)-5-[(3,5-dichlorophenoxy)methyl]-6-hydroxyoctahydrocyclopenta[b]pyran-2-yl}-1,3-thiazole-4-carboxylate (Compound 3-2)

TLC: Rf 0.65 (hexane:ethyl acetate=1:4);
$^1$H-NMR (CDCl$_3$): δ 1.38, 1.65-1.74, 1.85, 1.97-2.16, 2.21-2.37, 2.45, 2.59, 3.94, 4.05, 4.16, 4.25, 5.21, 5.27, 6.79, 6.96, 8.15.

Example 3 (3): isopropyl 2-{(2R,4aR,5S,6R,7aS)-6-hydroxy-5-[(3-methyl-4-nitrophenoxy)methyl]octahydrocyclopenta[b]pyran-2-yl}-1,3-thiazole-4-carboxylate (Compound 3-3)

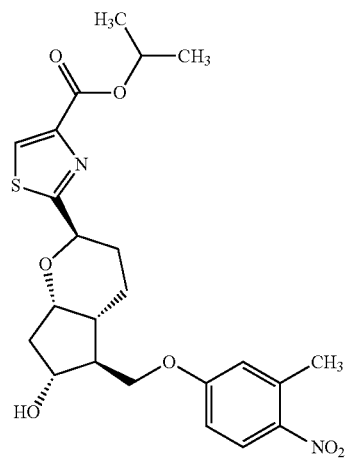 [SMILES: Cc1cc(OC[C@@H]2[C@H]3CC[C@H](c4nc(C(=O)OC(C)C)cs4)O[C@H]3C[C@H]2O)ccc1[N+](=O)[O-]]

TLC: Rf 0.30 (hexane:ethyl acetate=1:1);
$^1$H-NMR (CDCl$_3$): δ 1.38, 1.73, 1.85, 2.00, 2.08-2.16, 2.27-2.34, 2.47, 2.59, 2.63, 4.03, 4.12, 4.17, 4.25, 5.22, 5.27, 6.77, 6.78, 8.08, 8.14.

Example 3 (4): isopropyl 2-{((2R,4aR,5S,6R,7aS)-5-[(2,3-dihydro-1H-inden-5-yloxy)methyl]-6-hydroxyoctahydrocyclopenta[b]pyran-2-yl}-1,3-thiazole-4-carboxylate (Compound 3-4)

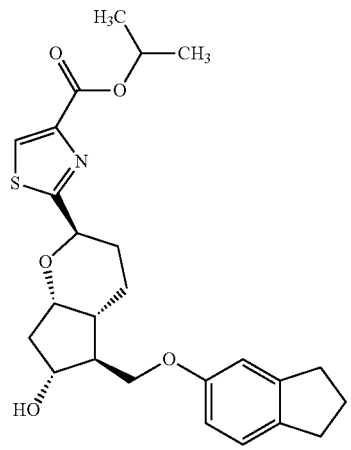 [SMILES: CC(C)OC(=O)c1csc([C@H]2CC[C@@H]3[C@@H](COc4ccc5c(c4)CCC5)[C@H](O)C[C@@H]3O2)n1]

TLC: Rf 0.78 (hexane:ethyl acetate=1:4);
$^1$H-NMR (CDCl$_3$): δ 1.37, 1.72, 1.85, 2.00, 2.02-2.17, 2.27, 2.43, 2.63, 2.87, 3.89, 4.04, 4.15, 4.24, 5.20, 5.26, 6.66, 6.77, 7.09, 8.13.

Example 3 (5): isopropyl 2-[(2R,4aR,5S,6R,7aS)-6-hydroxy-5-{[3-(trifluoromethoxy)phenoxy]methyl}octahydrocyclopenta[b]pyran-2-yl]-1,3-thiazole-4-carboxylate (Compound 3-5)

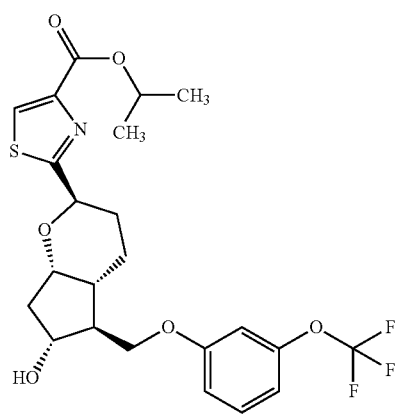 [SMILES: CC(C)OC(=O)c1csc([C@H]2CC[C@@H]3[C@@H](COc4cccc(OC(F)(F)F)c4)[C@H](O)C[C@@H]3O2)n1]

TLC: Rf 0.74 (dichloromethane:methanol=9:1);
$^1$H-NMR (CDCl$_3$): δ 1.38, 1.70, 1.87, 2.00, 2.09-2.18, 2.31, 2.46, 2.61, 3.95, 4.07, 4.18, 4.26, 5.21, 5.27, 6.74, 6.81, 7.18-7.29, 8.14.

Example 3 (6): isopropyl 2-{(2R,4aR,5S,6R,7aS)-5-[(3-fluorophenoxy)methyl]-6-hydroxyoctahydrocyclopenta[b]pyran-2-yl}-1,3-thiazole-4-carboxylate (Compound 3-6)

TLC: Rf 0.71 (hexane:ethyl acetate=1:4);
$^1$H-NMR (CDCl$_3$): δ 1.38, 1.71, 1.85, 2.01, 2.09-2.18, 2.30, 2.43, 2.61, 3.93, 4.05, 4.17, 4.26, 5.21, 5.27, 6.57-6.68, 7.19, 8.14.

Example 3 (7): isopropyl 2-{(2R,4aR,5S,6R,7aS)-6-hydroxy-5-[(2,3,4-trifluorophenoxy)methyl]octahydrocyclopenta[b]pyran-2-yl}-1,3-thiazole-4-carboxylate (Compound 3-7)

TLC: Rf 0.56 (hexane:ethyl acetate=1:4);
$^1$H-NMR (CDCl$_3$): δ 1.38, 1.70, 1.89, 2.00, 2.08-2.20, 2.30, 2.45, 2.62, 4.00, 4.12, 4.20, 4.26, 5.21, 5.24, 6.65, 6.86, 8.14.

Example 3 (8): isopropyl 2-{(2R,4aR,5S,6R,7aS)-5-[(4-cyano-3-methylphenoxy)methyl]-6-hydroxyoctahydrocyclopenta[b]pyran-2-yl}-1,3-thiazole-4-carboxylate (Compound 3-8)

TLC: Rf 0.36 (hexane:ethyl acetate=1:2);
$^1$H-NMR (CDCl$_3$): δ 1.38, 1.71, 1.85, 2.00, 2.05, 2.08-2.17, 2.27-2.33, 2.47, 2.51, 2.59, 3.99, 4.09, 4.16, 4.26, 5.22, 5.25, 6.76, 6.80, 7.52, 8.15.

Example 3 (9): isopropyl 2-{(2R,4aR,5S,6R,7aS)-5-[(2,3-dihydro-1H-inden-4-yloxy)methyl]-6-hydroxyoctahydrocyclopenta[b]pyran-2-yl}-1,3-thiazole-4-carboxylate (Compound 3-9)

TLC: Rf 0.65 (hexane:ethyl acetate=1:2);
$^1$H-NMR (CDCl$_3$): δ 1.38, 1.74, 1.89, 1.96-2.20, 2.31, 2.45, 2.70, 2.82, 2.91, 3.98, 4.09, 4.17, 4.26, 5.21, 5.26, 6.64, 6.84, 7.10, 8.14.

Example 3 (10): isopropyl 2-[(2R,4aR,5S,6R,7aS)-5-{[(4-fluoro-2,3-dihydro-1H-inden-5-yl)oxy]methyl)}-6-hydroxyoctahydrocyclopenta[b]pyran-2-yl]-1,3-thiazole-4-carboxylate (Compound 3-10)

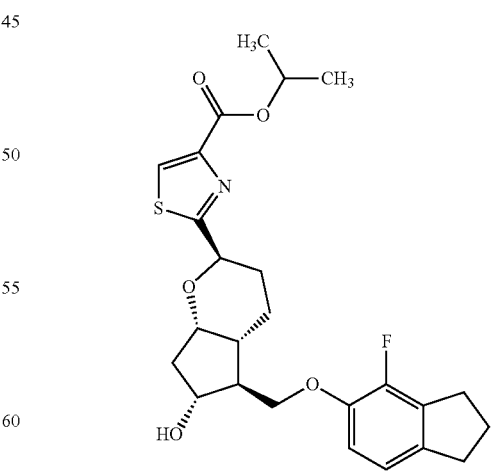

TLC: Rf 0.58 (hexane:ethyl acetate=3:7);
$^1$H-NMR (CDCl$_3$): δ 1.38, 1.65-1.77, 1.83-2.31, 2.40-2.50, 2.87, 2.93, 3.97, 4.14, 4.18-4.28, 5.20, 5.27, 6.75, 6.87, 8.14.

Example 3 (11): isopropyl 2-[(2R,4aR,5S,6R,7aS)-6-hydroxy-5-{[(6-methyl-2,3-dihydro-1H-inden-5-yl)oxy]methyl}octahydrocyclopenta[b]pyran-2-yl]-1,3-thiazole-4-carboxylate (Compound 3-11)

TLC: Rf 0.59 (hexane:ethyl acetate=1:1);
$^1$H-NMR (CDCl$_3$): δ 1.38, 1.72, 1.92, 1.99-2.20, 2.15, 2.31, 2.46, 2.70, 2.83, 3.93, 4.06, 4.20, 4.26, 5.21, 5.26, 6.72, 6.98, 8.14.

Example 3 (12): isopropyl 2-{(2R,4aR,5S,6R,7aS)-5-[(4-chlorophenoxy)methyl]-6-hydroxyoctahydrocyclopenta[b]pyran-2-yl}-1,3-thiazole-4-carboxylate (Compound 3-12)

TLC: Rf 0.74 (hexane:ethyl acetate=1:4);
$^1$H-NMR (CDCl$_3$): δ 1.38, 1.70, 1.85, 1.98, 2.06-2.17, 2.29, 2.44, 2.60, 3.92, 4.04, 4.17, 4.24, 5.20, 5.26, 6.80, 7.22, 8.14.

Example 4: 2-{(2R,4aR,5S,6R,7aS)-5-[(2,3-dihydro-1H-inden-5-yloxy)methyl]-6-hydroxyoctahydrocyclopenta[b]pyran-2-yl}-N-ethyl-1,3-thiazole-4-carboxamide (Compound 4)

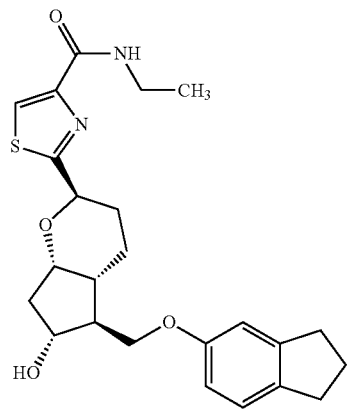 [SMILES: CCNC(=O)c1csc([C@H]2CC[C@@H]3[C@@H](COc4ccc5c(c4)CCC5)[C@H](O)C[C@@H]3O2)n1]

Dichloromethane (1.0 mL), a 2 M ethylamine/tetrahydrofuran solution (120 μL), 1-hydroxybenzotriazole (32 mg) and 1-ethyl-3-(3-dimethylaminopropyl)carbodiimide hydrochloride (46 mg) were added to 2-{(2R,4aR,5S,6R,7aS)-5-[(2,3-dihydro-1H-inden-5-yloxy)methyl]-6-hydroxyoctahydrocyclopenta[b]pyran-2-yl}-N-ethyl-1,3-thiazole-4-carboxylic acid (50 mg) that was produced by carrying out the same procedures as in Example A→Example 1 except that 2,3-dihydro-1H-inden-5-ol was used in place of 3,5-difluorophenol. The resulting solution was stirred at 60° C. for 2.5 hours. The reaction solution was purified by silica gel column chromatography (hexane:ethyl acetate=1:1→0:100) to produce the title compound (45 mg) having the following physical property values.

TLC: Rf 0.56 (ethyl acetate);
$^1$H-NMR (CDCl$_3$): δ 1.26, 1.76, 1.86, 1.95-2.23, 2.25-2.31, 2.46, 2.68, 2.85, 3.49, 3.93, 4.05, 4.21, 4.22, 5.18, 6.67, 6.78, 7.10, 7.28, 8.12.

Examples 4 (1) to 4 (3)

The same procedure as in Example 4 was carried out except that 2,3-dihydro-H-inden-5-ol or a corresponding substituted phenol was used and, in place of ethylamine, a corresponding amine was used. In this manner, the following compounds were produced.

Example 4 (1): 2-{(2R,4aR,5S,6R,7aS)-5-[(2,3-dihydro-1H-inden-5-yloxy)methyl]-6-hydroxyoctahydrocyclopenta[b]pyran-2-yl}-N-isopropyl-1,3-thiazole-4-carboxamide (Compound 4-1)

TLC: Rf 0.67 (ethyl acetate);
$^1$H-NMR (CDCl$_3$): δ 1.27, 1.73, 1.86, 1.95-2.19, 2.25, 2.45, 2.68, 2.85, 3.93, 4.05, 4.18, 4.21-4.30, 5.17, 6.67, 6.78, 7.07, 7.10, 8.10.

Example 4 (2): (2-{(2R,4aR,5S,6R,7aS)-6-hydroxy-5-[(3-methyl-4-nitrophenoxy)methyl]octahydrocyclopenta[b]pyran-2-yl}-1,3-thiazol-4-yl)(4-morpholinyl)methanone (Compound 4-2)

TLC: Rf 0.20 (ethyl acetate);
$^1$H-NMR (CDCl$_3$): δ 1.74, 1.81, 1.99, 2.04-2.16, 2.23-2.27, 2.51, 2.63, 2.64, 3.65-3.84, 3.90-3.99, 4.04, 4.12, 4.16-4.21, 5.21, 6.77, 6.78, 7.99, 8.07.

Example 4 (3): ethyl (2S)-2-{[(2-{(2R,4aR,5S,6R,7aS)-5-[(4-ethyl-3-methylphenoxy)methyl]-6-hydroxyoctahydrocyclopenta[b]pyran-2-yl}-1,3-thiazol-4-yl)carbonyl]amino}-3-methylbutanoate (Compound 4-3)

TLC: Rf 0.74 (ethyl acetate);
$^1$H-NMR (CDCl$_3$): δ 1.00, 1.19, 1.30, 1.77, 1.86, 1.97, 2.04-2.18, 2.27, 2.45, 2.50, 2.56, 2.66, 3.91, 4.05, 4.13-4.67, 4.69, 5.20, 6.68, 6.70, 7.05, 7.75, 8.13.

Example 4 (4): (2S)-2-{[(2-{(2R,4aR,5S,6R,7aS)-5-[(4-ethyl-3-methylphenoxy)methyl]-6-hydroxyoctahydrocyclopenta[b]pyran-2-yl}-1,3-thiazol-4-yl)carbonyl]amino}-3-methylbutanoic acid (Compound 4-4)

The same procedure as in Example 1 was carried out except that compound 4 (3) was used in place of Compound A, thereby producing the title compound having the following physical property values.

TLC: Rf 0.61 (dichloromethane:methanol=4:1);
$^1$H-NMR (CDCl$_3$): δ 1.04, 1.17, 1.75, 1.86, 1.97, 2.04-2.16, 2.27, 2.36-2.49, 2.55, 3.93, 4.06, 4.18, 4.20, 4.66, 5.19, 6.67, 6.69, 7.04, 7.73, 8.16.

Reference Example 11: isopropyl 2-{(2R,4aR,5S,6R,7aS)-6-hydroxy-5-[(3-methyl-4-nitrophenoxy)methyl]octahydrocyclopenta[b]pyran-2-yl}-1,3-thiazole-4-carboxylate (Reference compound 11)

The same procedures as in Example A→Example 1→Example 3 were carried out except that 3-methyl-4-nitrophenol was used in place of 3,5-difluorophenol, thereby producing the title compound having the following physical property values.

TLC: Rf 0.30 (hexane:ethyl acetate=1:1);
$^1$H-NMR (CDCl$_3$): δ 1.38, 1.73, 1.85, 2.00, 2.08-2.16, 2.27-2.34, 2.47, 2.59, 2.63, 4.03, 4.12, 4.17, 4.25, 5.22, 5.27, 6.77, 6.78, 8.08, 8.14.

Reference Example 12: isopropyl 2-{(2R,4aR,5S, 6R,7aS)-6-{(tert-butyl(dimethyl)silyl]oxy}-5-[(3-methyl-4-nitrophenoxy)methyl]octahydrocyclopenta[b]pyran-2-yl}-1,3-thiazole-4-carboxylate (Reference compound 12)

Dichloromethane (3.5 mL) and 2,6-dimethylpyridine (62 µL) were added to Reference compound 11 (170 mg) under argon stream, and the mixed solution was stirred at 0° C. for 5 minutes. tert-Butyldimethylsilyltrifluoromethanesulfonate (90 µL) was added to the resulting solution, and the solution was stirred at 0° C. for 2.5 hours. Water was added to the reaction solution, and the reaction solution was extracted with ethyl acetate. The organic layer was dried over anhydrous sodium sulfate, and then filtrated. The filtrate was concentrated under reduced pressure, and the residue was purified by silica gel column chromatography (hexane:ethyl acetate=9:1→3:1) to produce the title compound (128 mg) having the following physical property value.

TLC: Rf 0.71 (hexane:ethyl acetate=2:1).

Reference Example 13: (2-{(2R,4aR,5S,6R,7aS)-6-{(tert-butyl(dimethyl)silyl]oxy}-5-[(3-methyl-4-nitrophenoxy)methyl]octahydrocyclopenta[b]pyran-2-yl}-1,3-thiazole-4-yl) methanol (Reference compound 13)

The same procedure as in Example 2 was carried out except that Reference compound 12 was used in place of Compound A, thereby producing the title compound having the following physical property value.

TLC: Rf 0.71 (hexane:ethyl acetate=1:2).

Reference Example 14: 2-{(2R,4aR,5S,6R,7aS)-6-{(tert-butyl(dimethyl)silyl]oxy}-5-[(3-methyl-4-nitrophenoxy)methyl]octahydrocyclopenta[b]pyran-2-yl}-4-(methoxymethyl)-1,3-thiazole (Reference compound 14)

Tetrahydrofuran (1.0 mL) and 60% sodium hydride (3.8 mg) were added to Reference compound 13 (39 mg) under argon stream, and the mixed solution was stirred at room temperature for 5 minutes. Iodomethane (22 µL) was added to the resulting solution, and the reaction solution was stirred at room temperature for 5 hours. Water was added to the reaction solution, and the reaction solution was extracted with ethyl acetate. The organic layer was washed with saturated brine, then dried over anhydrous sodium sulfate, and then filtrated. The filtrate was concentrated under reduced pressure, and the residue was purified by silica gel column chromatography (hexane:ethyl acetate=9:1→2:1) to produce the title compound (32 mg) having the following physical property value.

TLC: Rf 0.50 (hexane:ethyl acetate=2:1).

Example 5: (2R,4aR,5S,6R,7aS)-2-[4-(methoxymethyl)-1,3-thiazol-2-yl]-5-[(3-methyl-4-nitrophenoxy)methyl]octahydrocyclopenta[b]pyran-6-ol (Compound 5)

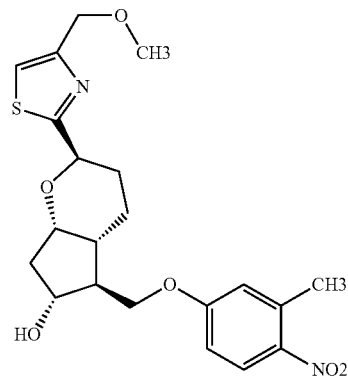 [SMILES: COCc1csc([C@H]2CC[C@@H]3[C@@H](COc4ccc([N+](=O)[O-])c(C)c4)[C@H](O)C[C@@H]3O2)n1]

Tetrahydrofuran (1.0 mL) and a 1 M tetra-n-butylammonium fluoride/tetrahydrofuran solution (116 µL) were added to Reference compound 14 (32 mg) under argon stream, and the mixed solution was stirred at room temperature for 2.5 hours. A saturated aqueous ammonium chloride solution was added to the reaction solution, and the reaction solution was extracted with ethyl acetate. The organic layer was washed with water and saturated brine, then dried over anhydrous sodium sulfate, and then filtrated. The filtrate was concentrated under reduced pressure, and the residue was purified by silica gel column chromatography (hexane:ethyl acetate=1:1→0:100) to produce the title compound (25 mg) having the following physical property values.

TLC: Rf 0.29 (hexane:ethyl acetate=1:2);

$^1$H-NMR (CDCl$_3$): δ 1.71, 1.84, 2.02-2.14, 2.27, 2.49, 2.62, 2.71, 3.48, 4.02, 4.12, 4.14, 4.27, 4.56, 5.20, 6.77, 6.78, 7.26, 8.07.

Reference Example 15: (2-{(2R,4aR,5S,6R,7aS)-6-{(tert-butyl(dimethyl)silyl]oxy}-5-[(3-methyl-4-nitrophenoxy)methyl]octahydrocyclopenta[b]pyran-2-yl}-1,3-thiazole-4-yl)methyl-2-methylpropionate (Reference compound 15)

Dichloromethane (1.0 mL), pyridine (17 µL), isobutyryl chloride (8.4 µL) were added to Reference compound 13 (39 mg) under argon stream, and the mixed solution was stirred at room temperature for 3 hours. A 1 M aqueous hydrochloric acid solution was added to the reaction solution, and the reaction solution was extracted with ethyl acetate. The organic layer was washed with water and saturated brine, then dried over anhydrous sodium sulfate, and then filtrated. The filtrate was concentrated under reduced pressure, and the residue was purified by silica gel column chromatography (hexane:ethyl acetate=9:1→2:1) to produce the title compound (43 mg) having the following physical property value.

TLC: Rf 0.75 (hexane:ethyl acetate=2:1).

Example 6: (2-{(2R,4aR,5S,6R,7aS)-6-hydroxy-5-[(3-methyl-4-nitrophenoxy)methyl]octahydrocyclopenta[b]pyran-2-yl}-1,3-thiazol-4-yl)methyl 2-methylpropanoate (Compound 6)

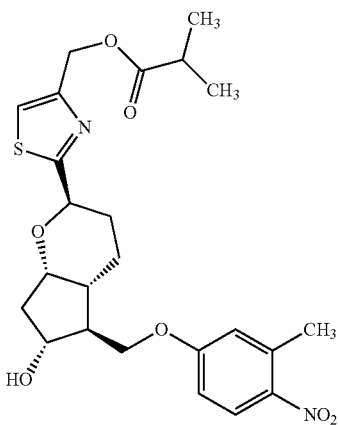 [SMILES: Cc1cc(OC[C@@H]2[C@H]3CC[C@H](c4nc(COC(=O)C(C)C)cs4)O[C@H]3C[C@H]2O)ccc1[N+](=O)[O-]]

The same procedure as in Example 5 was carried out except that Reference compound 15 was used in place of Reference compound 14, thereby producing the title compound having the following physical property values.

TLC: Rf 0.59 (hexane:ethyl acetate=1:2);
$^1$H-NMR (CDCl$_3$): δ 1.20, 1.72, 1.84, 1.98-2.16, 2.26, 2.50, 2.62, 4.03, 4.12, 4.18, 4.26, 5.16-5.26, 6.77, 6.78, 7.26, 8.07.

Examples 6 (1), 6 (2)

The same procedures as in Example A→Example 1→Example 3→Reference example 12→Example 2→Reference example 15→Example 6 were carried out except that, in place of 3,5-difluorophenol, a corresponding substituted phenol was used. In this manner, the following compounds were produced.

Example 6 (1): (2-{(2R,4aR,5S,6R,7aS)-5-[(2,3-dihydro-1H-inden-5-yloxy)methyl]-6-hydroxyoctahydrocyclopenta[b]pyran-2-yl}-1,3-thiazol-4-yl) methyl 2-methylpropanoate (Compound 6-1)

TLC: Rf 0.26 (hexane:ethyl acetate=2:1);
$^1$H-NMR (CDCl$_3$): δ 1.20, 1.70, 1.84, 2.00-2.16, 2.22, 2.45, 2.63, 2.85, 3.91, 4.06, 4.17, 4.26, 5.17-5.27, 6.67, 6.78, 7.10, 7.27.

Example 6 (2): (2-{((2R,4aR,5S,6R,7aS)-5-[(4-chloro-3-cyclopropylphenoxy)methyl]-6-hydroxyoctahydrocyclopenta[b]pyran-2-yl}-1,3-thiazol-4-yl) methyl acetate (Compound 6-2)

TLC: Rf 0.34 (hexane:ethyl acetate=4:6);
$^1$H-NMR (CDCl$_3$): δ 0.66, 1.00, 1.60-1.87, 1.94-2.20, 2.12, 2.20-2.30, 2.39-2.48, 3.87, 4.00, 4.16, 4.26, 5.16-5.23, 6.44, 6.62, 7.22, 7.30.

Reference Example 16: isopropyl 2-[(2R,4aR,5S, 6R,7aS)-5-({[tert-butyl(diphenyl)silyl]oxy}methyl)-6-hydroxyoctahydrocyclopenta[b]pyran-2-yl]-1,3-thiazole-4-carboxylate (Reference compound 16)

The same procedures as in Example 1→Example 3 were carried out except that Reference compound 8 was used in place of Compound A, thereby producing the title compound having the following physical property value.

TLC: Rf 0.20 (hexane:ethyl acetate=3:1).

Reference Example 17: isopropyl 2-[(2R,4aR,5S, 6R,7aS)-5-({[tert-butyl(diphenyl)silyl]oxy}methyl)-6-(tetrahydro-2H-pyran-2-yloxy)octahydrocyclopenta[b]pyran-2-yl]-1,3-thiazole-4-carboxylate (Reference compound 17)

Dichloromethane (220 mL) and pyridinium paratoluenesulfonate (2.3 g) were added to Reference compound 16 (54.8 g) under nitrogen stream. 3,4-Dihydro-2H-pyran (15.9 g) was added to the mixed solution at room temperature, and the resulting solution was stirred in a water bath overnight. A saturated aqueous sodium hydrogen carbonate solution (200 mL) was added to the reaction solution, and the reaction solution was extracted with ethyl acetate. The organic layer was washed with water and saturated brine, then dried over anhydrous sodium sulfate, and then filtrated. The filtrate was concentrated under reduced pressure to produce the title compound having the following physical property value. The compound thus produced was used in the subsequent reaction without purification.

TLC: Rf 0.50 (hexane:ethyl acetate=3:1).

Reference Example 18: isopropyl 2-[(2R,4aR,5S, 6R,7aS)-5-(hydroxymethyl)-6-(tetrahydro-2H-pyran-2-yloxy)octahydrocyclopenta[b]pyran-2-yl]-1,3-thiazole-4-carboxylate (Reference compound 18)

The same procedure as in Example 5 was carried out except that Reference compound 17 was used in place of Reference compound 14, thereby producing the title compound having the following physical property value.

TLC: Rf 0.40 (hexane:ethyl acetate=1:2).

Reference Example 19: isopropyl 2-[(2R,4aR,5S, 6R,7aS)-5-formyl-6-(tetrahydro-2H-pyran-2-yloxy) octahydrocyclopenta[b]pyran-2-yl]-1,3-thiazole-4-carboxylate (Reference compound 19)

Dichloromethane (3.0 mL) and dimethyl sulfoxide (1.5 mL) were added to Reference compound 18 (300 mg) under argon stream, and the mixed solution was stirred at 0° C. for 5 minutes. Triethylamine (589 µL) and a sulfur trioxide pyridine complex (336 mg) were added to the resulting solution, and the resulting solution was stirred at room temperature for 4.5 hours. A 1 M aqueous hydrochloric acid solution was added to the reaction solution, and the reaction solution was extracted with ethyl acetate. The organic layer was washed with a saturated aqueous sodium hydrogen carbonate solution and saturated brine, then dried over anhydrous sodium sulfate, and then filtrated. The filtrate was concentrated under reduced pressure to produce the title compound having the following physical property value. The compound thus produced was used in the subsequent reaction without purification.

TLC: Rf 0.81 (hexane:ethyl acetate=1:2).

Reference Example 20: isopropyl 2-[(2R,4aR,5S, 6R,7aS)-5-[(2,3-dihydro-1H-inden-5-ylamino) methyl]-6-(tetrahydro-2H-pyran-2-yloxy)octahydrocyclopenta[b]pyran-2-yl]-1,3-thiazole-4-carboxylate (Reference compound 20)

Dichloromethane (3.0 mL), 5-aminoindane (94 mg) and acetic acid (80 µL) were added to Reference compound 19

(298 mg) under argon stream, and the mixed solution was stirred at 0° C. for 5 minutes. Sodium triacetoxyborohydride (179 mg) was added to the resulting solution, and the resulting solution was stirred at room temperature for 30 minutes. Saturated brine was added to the reaction solution, and the reaction solution was extracted with ethyl acetate. The organic layer was dried over anhydrous sodium sulfate, and then filtrated. The filtrate was concentrated under reduced pressure, and the residue was purified by silica gel column chromatography (hexane:ethyl acetate=9:1→2:1) to produce the title compound (357 mg) having the following physical property value.

TLC: Rf 0.45 (hexane:ethyl acetate=2:1).

Example 7: isopropyl 2-{((2R,4aR,5S,6R,7aS)-5-[(2,3-dihydro-1H-inden-5-ylamino)methyl]-6-hydroxyoctahydrocyclopenta[b]pyran-2-yl}-1,3-thiazole-4-carboxylate (Compound 7)

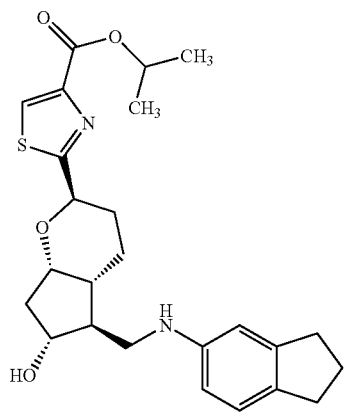 [SMILES: CC(C)OC(=O)c1csc([C@H]2CC[C@@H]3[C@@H](CNc4ccc5c(c4)CCC5)[C@H](O)C[C@@H]3O2)n1]

Paratoluenesulfonic acid monohydrate (5.2 mg) and methanol (2.0 mL) were added to Reference compound 20 (150 mg) under argon stream, and the mixed solution was stirred at room temperature for 1 hour. Subsequently, paratoluenesulfonic acid monohydrate (5.2 mg) was added to the resulting solution, and the resulting solution was stirred at room temperature for 4.5 hours. Water was added to the reaction solution, and the reaction solution was extracted with ethyl acetate. The organic layer was washed with saturated brine, dried over anhydrous sodium sulfate, and then filtrated. The filtrate was concentrated under reduced pressure, and the residue was purified by silica gel column chromatography (hexane:ethyl acetate=9:1→2:1) to produce the title compound (123 mg) having the following physical property values.

TLC: Rf 0.24 (hexane:ethyl acetate=2:1);
$^1$H-NMR (CDCl$_3$): δ 1.39, 1.61-1.72, 1.91, 2.04, 2.11-2.20, 2.27, 2.60, 2.82, 3.01, 3.24, 4.05, 4.19, 5.19, 5.27, 6.45, 6.55, 7.04, 8.14.

Example 8: 2-{(2R,4aR,5S,6R,7aS)-5-[(2,3-dihydro-1H-inden-5-ylamino)methyl]-6-hydroxyoctahydrocyclopenta[b]pyran-2-yl}-1,3-thiazole-4-carboxylic acid (Compound 8)

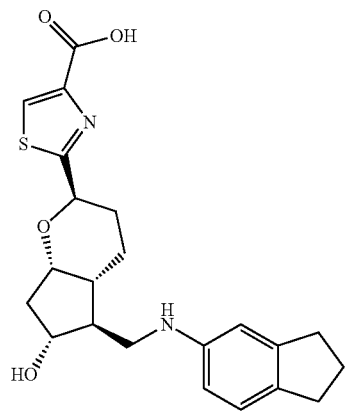 [SMILES: O=C(O)c1csc([C@H]2CC[C@@H]3[C@@H](CNc4ccc5c(c4)CCC5)[C@H](O)C[C@@H]3O2)n1]

The same procedure as in Example 1 was carried out except that compound 7 was used in place of Compound A, thereby producing the title compound having the following physical property values.

TLC: Rf 0.48 (chloroform:methanol:acetic acid=9:1:0.1);
$^1$H-NMR (CDCl$_3$): δ 1.62-1.71, 1.92, 1.95-2.08, 2.14-2.27, 2.81, 3.02, 3.25, 4.07, 4.15, 5.18, 6.46, 6.57, 7.03, 8.29.

Example B: ethyl 2-((2R,4aR,5S,6R,7aS)-6-acetyloxy-5-((3,4-dicyclopropylphenoxy)methyl)octahydrocyclopenta[b]pyran-2-yl)thiazole-4-carboxylate (compound B)

The same procedure as in Example A was carried out except that 3,4-dicyclopropylphenol was used in place of 3,5-difluorophenol, thereby producing the title compound having the following physical property values.

TLC: Rf 0.63 (hexane:ethyl acetate=1:1).
$^1$H-NMR (CDCl$_3$): δ 0.60, 0.68, 0.87-0.99, 1.40, 1.69-1.76, 1.90-2.05, 2.08, 2.08-2.28, 2.39-2.49, 4.00, 4.33, 4.43, 5.09, 5.17, 6.47, 6.60, 6.91, 8.16.

Example C: methyl 2-((2R,4aR,5S,6R,7aS)-5-((3,4-dicyclopropylphenoxy)methyl)-6-hydroxyoctahydrocyclopenta[b]pyran-2-yl)thiazole-4-carboxylate (compound C)

Methanol (2.0 mL) and potassium carbonate (87 mg) were added to compound B (110 mg) under argon stream, and the mixed solution was stirred at room temperature for 1 hour. The reaction solution was filtrated through Celite, and then the filtrate was concentrated under reduced pressure, and the residue was purified by silica gel column chromatography (hexane:ethyl acetate=4:1→0:100) to produce the title compound (17 mg) having the following physical property values.

TLC: Rf 0.30 (hexane:ethyl acetate=1:1).
$^1$H-NMR (CDCl$_3$): δ 0.62, 0.68, 0.87-1.00, 1.41, 1.62-1.75, 1.81-1.90, 1.95-2.29, 2.33-2.45, 2.67, 3.86-3.91, 4.01-4.04, 4.16, 4.25, 4.43, 5.21, 6.48, 6.61, 6.90, 8.18.

Example D: methyl 2-((2R,4aR,5S,6S,7aS)-5-((3,4-dicyclopropylphenoxy)methyl)-6-(formyloxy)octahydrocyclopenta[b]pyran-2-yl)thiazole-4-carboxylate (compound D)

Tetrahydrofuran (0.20 mL), formic acid (5.0 mg) and triphenylphosphine (19 mg) were added to compound C (17 mg) under argon stream, and the mixed solution was stirred. 2.2 M diethyl azocarboxylate/tetrahydrofuran (33 μL) was added dropwise to the resulting solution, and the resulting solution was stirred at room temperature overnight. Formic acid (5.0 mg) and triphenylphosphine (19 mg) were added to the reaction solution, then 2.2 M diethyl azocarboxylate/tetrahydrofuran (33 μL) was added dropwise to the reaction solution, and then the reaction solution was stirred at 50° C. overnight. The reaction solution was purified by silica gel column chromatography (hexane:ethyl acetate=9:1→1:1) to produce the title compound (15 mg) having the following physical property values.

TLC: Rf 0.74 (hexane:ethyl acetate=1:1).
$^1$H-NMR (CDCl$_3$): δ 0.62, 0.68, 0.87-0.98, 1.40, 1.60-1.66, 2.02-2.33, 2.61-2.67, 3.92-4.04, 4.31, 4.41, 5.11, 5.60, 6.46, 6.60, 6.90, 7.96, 8.16.

Example 9: 2-{(2R,4aR,5S,6S,7aS)-5-[(3,4-dicyclopropylphenoxy)methyl]-6-hydroxyoctahydrocyclopenta[b]pyran-2-yl}-1,3-thiazole-4-carboxylic acid (Compound 9)

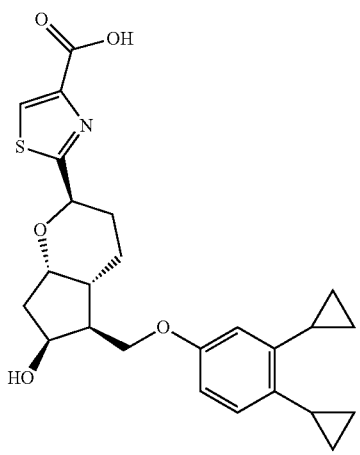 [SMILES: O=C(O)c1csc([C@H]2CC[C@@H]3[C@@H](COc4ccc(C5CC5)c(C5CC5)c4)[C@@H](O)C[C@@H]3O2)n1]

Methanol (0.40 mL), dimethoxyethane (0.40 mL) and a 2 M aqueous sodium hydroxide solution (0.16 mL) were added to compound D (6.0 mg) under argon stream, and the mixed solution was stirred at room temperature for 1 hour. AG50W-X8 resin (trade name) (100 mg) was added to the reaction solution, and the reaction solution was shaken at room temperature for 30 minutes. The resulting solution was filtrated through a glass filter, and then the filtrate was concentrated under reduced pressure to produce the title compound (4.7 mg) having the following physical property values.

TLC: Rf 0.33 (dichloromethane:methanol:acetic acid=10:1:0.1);
$^1$H-NMR (CDCl$_3$): δ 0.62, 0.67, 0.91, 0.97, 1.95-2.30, 2.42-2.51, 4.10, 4.30, 4.63, 5.09, 6.51, 6.65, 6.92, 8.27.

Examples 9 (1) to (45)

The same procedures as in Example A→Example C→Example D→Example 9 were carried out except that, in place of 3,5-difluorophenol, a corresponding substituted phenol was used. In this manner, the following compounds were produced.

Example 9 (1): 2-{(2R,4aR,5S,6S,7aS)-5-[(2,3-dihydro-1H-inden-5-yloxy)methyl]-6-hydroxyoctahydrocyclopenta[b]pyran-2-yl}-1,3-thiazole-4-carboxylic acid (Compound 9-1)

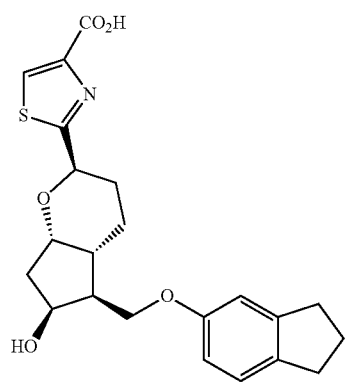 [SMILES: O=C(O)c1csc([C@H]2CC[C@@H]3[C@@H](COc4ccc5c(c4)CCC5)[C@@H](O)C[C@@H]3O2)n1]

TLC: Rf 0.14 (dichloromethane:methanol:water=90:10:1);
$^1$H-NMR (DMSO-d$_6$): δ 1.42-1.60, 1.90-2.25, 2.69-2.84, 3.86, 4.10, 4.19, 4.28, 4.60, 5.07, 6.66, 6.78, 7.07, 8.42.

Example 9 (2): 2-{(2R,4aR,5S,6S,7aS)-5-[(4-chloro-3-methylphenoxy)methyl]-6-hydroxyoctahydrocyclopenta[b]pyran-2-yl}-1,3-thiazole-4-carboxylic acid (Compound 9-2)

TLC: Rf 0.39 (chloroform:methanol:acetic acid=9:1:0.1);
$^1$H-NMR (CDCl$_3$): δ 1.60, 1.97-2.08, 2.16, 2.23, 2.34, 2.48, 4.10, 4.31, 4.63, 5.10, 6.70, 6.80, 7.22, 8.28.

Example 9 (3): 2-{(2R,4aR,5S,6S,7aS)-5-[(3-chloro-4-methylphenoxy)methyl]-6-hydroxyoctahydrocyclopenta[b]pyran-2-yl}-1,3-thiazole-4-carboxylic acid (Compound 9-3)

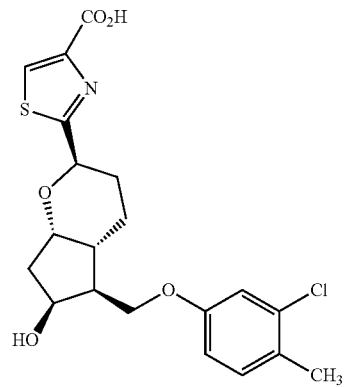 [SMILES: Cc1ccc(OC[C@@H]2[C@H]3CC[C@H](c4nc(C(=O)O)cs4)O[C@H]3C[C@@H]2O)cc1Cl]

TLC: Rf 0.60 (dichloromethane:methanol:water=80:20:1);
$^1$H-NMR (DMSO-d$_6$): δ 1.43-1.59, 1.91-2.01, 2.05-2.29, 2.23, 3.91, 4.10-4.23, 4.28, 4.62, 5.07, 6.82, 6.97, 7.22, 8.43.

Example 9 (4): 2-{(2R,4aR,5S,6S,7aS)-5-[(3-ethyl-4-methylphenoxy)methyl]-6-hydroxyoctahydrocyclopenta[b]pyran-2-yl}-1,3-thiazole-4-carboxylic acid (Compound 9-4)

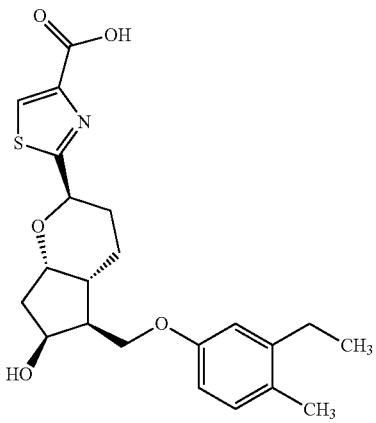 [SMILES: CCc1cc(OC[C@@H]2[C@H]3CC[C@H](c4nc(C(=O)O)cs4)O[C@H]3C[C@@H]2O)ccc1C]

TLC: Rf 0.50 (chloroform:methanol:acetic acid=9:1:0.1);
¹H-NMR (CDCl₃): δ 1.20, 1.58, 1.97-2.21, 2.23, 2.49, 2.59, 4.13, 4.32, 4.65, 5.10, 6.67, 6.74, 7.04, 8.28.

Example 9 (5): 2-[(2R,4aR,5S,6S,7aS)-5-{[(4-fluoro-2,3-dihydro-1H-inden-5-yl)oxy]methyl}-6-hydroxyoctahydrocyclopenta[b]pyran-2-yl]-1,3-thiazole-4-carboxylic acid (Compound 9-5)

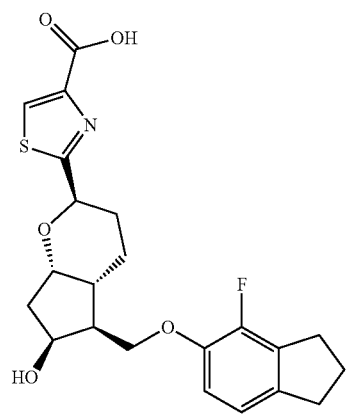 [SMILES: O=C(O)c1csc([C@H]2CC[C@@H]3[C@@H](COc4ccc5c(c4F)CCC5)[C@@H](O)C[C@@H]3O2)n1]

TLC: Rf 0.51 (chloroform:methanol:acetic acid=9:1:0.1);
¹H-NMR (CDCl₃): δ 1.57, 1.97-2.05, 2.06-2.24, 2.87, 2.94, 4.18, 4.32, 4.68, 5.10, 6.82, 6.89, 8.28.

Example 9 (6): 2-{(2R,4aR,5S,6S,7aS)-5-[(4-ethyl-3-methylphenoxy)methyl]-6-hydroxyoctahydrocyclopenta[b]pyran-2-yl}-1,3-thiazole-4-carboxylic acid (Compound 9-6)

TLC: Rf 0.43 (chloroform:methanol:acetic acid=9:1:0.1);
¹H-NMR (CDCl₃): δ 1.17, 1.58, 1.96-2.17, 2.22, 2.28, 2.49, 2.56, 4.12, 4.31, 4.63, 5.09, 6.69, 6.71, 7.05, 8.27.

Example 9 (7): 2-{(2R,4aR,5S,6S,7aS)-5-[(4-chloro-3-cyclopropylphenoxy)methyl]-6-hydroxyoctahydrocyclopenta[b]pyran-2-yl}-1,3-thiazole-4-carboxylic acid (Compound 9-7)

TLC: Rf 0.46 (dichloromethane:methanol=10:1) COOH Silica plate;
¹H-NMR (CDCl₃): δ 0.69, 1.04, 1.27, 1.56-1.62, 1.95-2.29, 2.49, 4.03-4.17, 4.31, 4.64, 5.10, 6.48, 6.68, 7.25, 8.27.

Example 9 (8): 2-{(2R,4aR,5S,6S,7aS)-5-[(3-chloro-4-ethylphenoxy)methyl]-6-hydroxyoctahydrocyclopenta[b]pyran-2-yl}-1,3-thiazole-4-carboxylic acid (Compound 9-8)

TLC: Rf 0.37 (dichloromethane:methanol=10:1) COOH Silica plate;
¹H-NMR (CDCl₃): δ 1.20, 1.57, 1.98-2.10, 2.23, 2.49, 2.68, 4.11, 4.31, 4.63, 5.10, 6.77, 6.93, 7.15, 8.27.

Example 9 (9): 2-{(2R,4aR,5S,6S,7aS)-5-[(3-cyclopropyl-4-methylphenoxy)methyl]-6-hydroxyoctahydrocyclopenta[b]pyran-2-yl}-1,3-thiazole-4-carboxylic acid (Compound 9-9)

TLC: Rf 0.41 (dichloromethane:methanol=10:1) COOH Silica plate;
¹H-NMR (CDCl₃): δ 0.64, 0.93, 1.45-1.75, 1.89, 1.98-2.23, 2.35, 2.47, 4.12, 4.32, 4.64, 5.10, 6.55, 6.66, 7.05, 8.28.

Example 9 (10): 2-{(2R,4aR,5S,6S,7aS)-5-[(4-chloro-3-fluorophenoxy)methyl]-6-hydroxyoctahydrocyclopenta[b]pyran-2-yl}-1,3-thiazole-4-carboxylic acid (Compound 9-10)

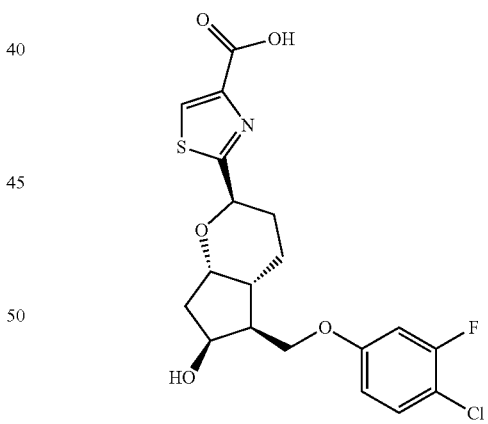

TLC: Rf 0.48 (dichloromethane:methanol=10:1) COOH Silica plate;
¹H-NMR (CDCl₃): δ 1.62, 1.97-2.05, 2.18, 2.21, 2.22, 2.49, 2.34, 4.05, 4.16, 4.30, 4.63, 5.10, 6.66, 6.74, 7.29, 8.28.

Example 9 (11): 2-{(2R,4aR,5S,6S,7aS)-5-[(4-fluoro-3-methylphenoxy)methyl]-6-hydroxyoctahydrocyclopenta[b]pyran-2-yl}-1,3-thiazole-4-carboxylic acid (Compound 9-11)

TLC: Rf 0.56 (dichloromethane:methanol=10:1) COOH Silica plate;

¹H-NMR (CDCl₃): δ 1.59, 1.96-2.04, 2.20, 2.25, 2.48, 4.05-4.15, 4.32, 4.65, 5.10, 6.70, 6.74, 6.91, 8.28.

Example 9 (12): 2-{(2R,4aR,5S,6S,7aS)-6-hydroxy-5-[(5,6,7,8-tetrahydro-2-naphthalenyloxy)methyl]octahydrocyclopenta[b]pyran-2-yl}-1,3-thiazole-4-carboxylic acid (Compound 9-12)

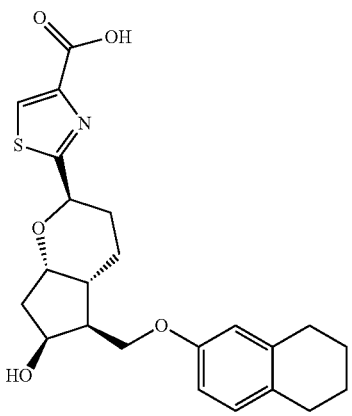 [SMILES: O=C(O)c1csc([C@H]2CC[C@@H]3[C@@H](COc4ccc5c(c4)CCCC5)[C@@H](O)C[C@@H]3O2)n1]

TLC: Rf 0.62 (dichloromethane:methanol=10:1) COOH Silica plate;

¹H-NMR (CDCl₃): δ 1.59, 1.77, 1.96-2.18, 2.23, 2.50, 2.71, 4.11, 4.31, 4.64, 5.09, 6.64, 6.69, 6.97, 8.27.

Example 9 (13): 2-{(2R,4aR,5S,6S,7aS)-5-[(3-cyclopropyl-4-fluorophenoxy)methyl]-6-hydroxyoctahydrocyclopenta[b]pyran-2-yl}-1,3-thiazole-4-carboxylic acid (Compound 9-13)

TIC: Rf 0.41 (dichloromethane:methanol=10:1) COOH Silica plate;

¹H-NMR (CDCl₃): δ 0.72, 0.99, 1.56, 1.97-2.07, 2.17, 2.23, 2.46, 4.07, 4.13, 4.30, 4.64, 5.10, 6.41, 6.64, 6.91, 8.27.

Example 9 (14): 2-{(2R,4aR,5S,6S,7aS)-5-[(3-chloro-4-fluorophenoxy)methyl]-6-hydroxyoctahydrocyclopenta[b]pyran-2-yl}-1,3-thiazole-4-carboxylic acid (Compound 9-14)

TLC: Rf 0.33 (dichloromethane:methanol=10:1) COOH Silica plate;

¹H-NMR (CDCl₃): δ 1.59, 1.97-2.08, 2.11-2.24, 2.49, 4.05, 4.13, 4.31, 4.63, 5.10, 6.78, 6.96, 7.05, 8.28.

Example 9 (15): 2-{(2R,4aR,5S,6S,7aS)-5-[(3,4-dichlorophenoxy)methyl]-6-hydroxyoctahydrocyclopenta[b]pyran-2-yl}-1,3-thiazole-4-carboxylic acid (Compound 9-15)

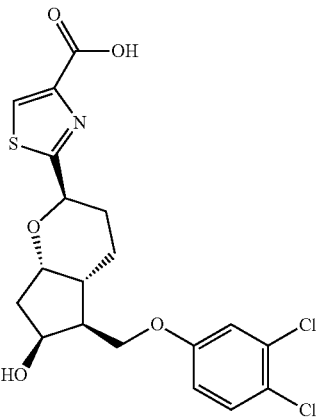 [SMILES: O=C(O)c1csc([C@H]2CC[C@@H]3[C@@H](COc4ccc(Cl)c(Cl)c4)[C@@H](O)C[C@@H]3O2)n1]

TLC: Rf 0.35 (dichloromethane:methanol=10:1) COOH Silica plate;

¹H-NMR (CDCl₃): δ 1.59, 1.98-2.11, 2.16, 2.22-2.35, 2.48, 4.06, 4.16, 4.30, 4.63, 5.10, 6.78, 7.03, 7.33, 8.28.

Example 9 (16): 2-{(2R,4aR,5S,6S,7aS)-5-[(bicyclo[4.2.0]octa-1,3,5-trien-3-yloxy)methyl]-6-hydroxyoctahydrocyclopenta[b]pyran-2-yl}-1,3-thiazole-4-carboxylic acid (Compound 9-16)

TLC: Rf 0.41 (dichloromethane:methanol=10:1) COOH Silica plate;

¹H-NMR (CDCl₃): δ 1.56, 1.96-2.12, 2.13-2.20, 2.23, 2.50, 3.11, 4.11, 4.30, 4.64, 5.10, 6.69, 6.75, 6.94, 8.27.

Example 9 (17): 2-{(2R,4aR,5S,6S,7aS)-5-[(4-ethyl-3-fluorophenoxy)methyl]-6-hydroxyoctahydrocyclopenta[b]pyran-2-yl}-1,3-thiazole-4-carboxylic acid (Compound 9-17)

TLC: Rf 0.43 (dichloromethane:methanol=10:1) COOH Silica plate;

¹H-NMR (CDCl₃): δ 1.19, 1.58, 1.97-2.11, 2.14-2.32, 2.49, 2.60, 4.10, 4.31, 4.64, 5.10, 6.61, 6.64, 7.08, 8.28.

Example 9 (18): 2-[(2R,4aR,5S,6S,7aS)-5-{[(7-fluoro-2,3-dihydro-1H-inden-5-yl)oxy]methyl}-6-hydroxyoctahydrocyclopenta[b]pyran-2-yl]-1,3-thiazole-4-carboxylic acid (Compound 9-18)

TLC: Rf 0.44 (dichloromethane:methanol=10:1) COOH Silica plate;

¹H-NMR (CDCl₃): δ 1.61, 1.97-2.30, 2.51, 2.89, 4.12, 4.30, 4.64, 5.11, 6.43, 6.61, 8.28.

Example 9 (19): 2-{(2R,4aR,5S,6S,7aS)-6-hydroxy-5-[(3-methoxy-4-methylphenoxy)methyl]octahydrocyclopenta[b]pyran-2-yl}-1,3-thiazole-4-carboxylic acid (Compound 9-19)

TLC: Rf 0.40 (dichloromethane:methanol=10:1) COOH Silica plate;

¹H-NMR (CDCl₃): δ 1.58-1.66, 1.98-2.34, 2.44-2.57, 3.80, 4.14, 4.34, 4.64, 5.11, 6.40-6.46, 7.03, 8.29.

Example 9 (20): 2-{(2R,4aR,5S,6S,7aS)-6-hydroxy-5-[(4-methyl-3-propylphenoxy)methyl]octahydrocyclopenta[b]pyran-2-yl}-1,3-thiazole-4-carboxylic acid (Compound 9-20)

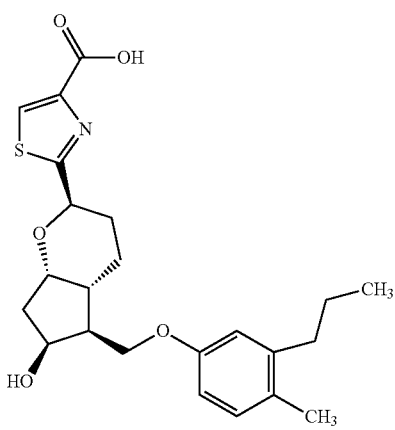 [SMILES: CCCc1cc(OC[C@@H]2[C@H]3CC[C@H](c4nc(C(=O)O)cs4)O[C@H]3C[C@@H]2O)ccc1C]

TLC: Rf 0.42 (dichloromethane:methanol=10:1) COOH Silica plate;
¹H-NMR (CDCl₃): δ 0.99, 1.50-1.70, 1.96-2.34, 2.41-2.59, 4.13, 4.32, 4.66, 5.10, 6.64-6.75, 7.04, 8.28.

Example 9 (21): 2-[(2R,4aR,5S,6S,7aS)-6-hydroxy-5-{[3-methyl-4-(methylthio)phenoxy]methyl}octahydrocyclopenta[b]pyran-2-yl]-1,3-thiazole-4-carboxylic acid (Compound 9-21)

TLC: Rf 0.37 (dichloromethane:methanol=10:1) COOH Silica plate;
¹H-NMR (CDCl₃): δ 1.50-1.70, 1.94-2.33, 2.38, 2.40, 2.42-2.56, 4.12, 4.32, 4.65, 5.10, 6.73-6.81, 7.19, 8.27.

Example 9 (22): 2-{(2R,4aR,5S,6S,7aS)-5-[(2,3-dihydro-1-benzofuran-6-yloxy)methyl]-6-hydroxyoctahydrocyclopenta[b]pyran-2-yl}-1,3-thiazole-4-carboxylic acid (Compound 9-22)

TLC: Rf 0.30 (dichloromethane:methanol=10:1) COOH Silica plate;
¹H-NMR (CDCl₃): δ 1.50-1.70, 1.94-2.33, 2.41-2.54, 3.13, 4.11, 4.30, 4.58, 4.63, 5.10, 6.40-6.45, 7.04, 8.26.

Example 9 (23): 2-{(2R,4aR,5S,6S,7aS)-5-[(3,4-diethylphenoxy)methyl]-6-hydroxyoctahydrocyclopenta[b]pyran-2-yl}-1,3-thiazole-4-carboxylic acid (Compound 9-23)

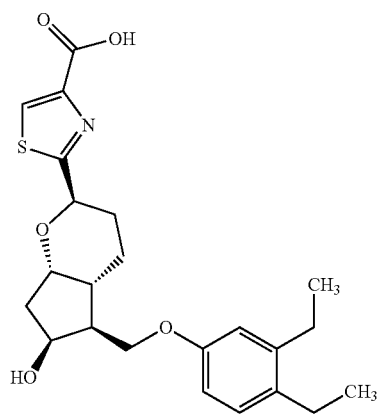 [SMILES: CCc1ccc(OC[C@@H]2[C@H]3CC[C@H](c4nc(C(=O)O)cs4)O[C@H]3C[C@@H]2O)cc1CC]

TLC: Rf 0.37 (dichloromethane:methanol=4:1);
¹H-NMR (CDCl₃): δ 1.19, 1.22, 1.60, 1.97-2.29, 2.49, 2.60, 2.62, 4.13, 4.32, 4.65, 5.10, 6.71, 6.75, 7.08, 8.27.

Example 9 (24): 2-{(2R,4aR,5S,6S,7aS)-5-[(4-fluoro-3-isopropylphenoxy)methyl]-6-hydroxyoctahydrocyclopenta[b]pyran-2-yl}-1,3-thiazole-4-carboxylic acid (Compound 9-24)

TLC: Rf 0.28 (dichloromethane:methanol=10:1) COOH Silica plate;
¹H-NMR (CDCl₃): δ 1.22, 1.49-2.40, 3.17, 3.94, 4.03, 4.25, 4.47, 4.93, 6.62, 6.72, 6.87, 7.93.

Example 9 (25): 2-[(2R,4aR,5S,6S,7aS)-6-hydroxy-5-{[(4-methyl-3-(methylthio)phenoxy]methyl}octahydrocyclopenta[b]pyran-2-yl]-1,3-thiazole-4-carboxylic acid (Compound 9-25)

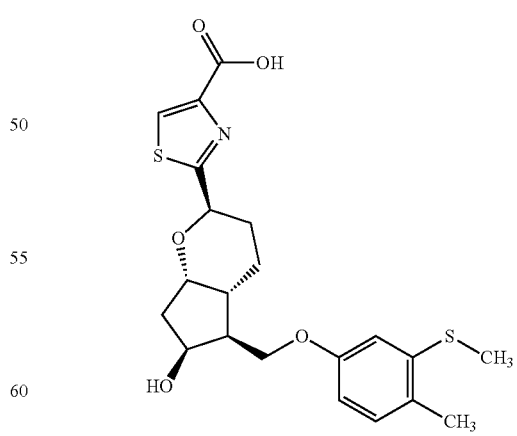

TLC: Rf 0.28 (dichloromethane:methanol=10:1) COOH Silica plate;
¹H-NMR (CDCl₃): δ 1.50-1.65, 1.95-2.34, 2.44, 2.45-2.56, 4.14, 4.32, 4.66, 5.11, 6.64, 6.74, 7.03, 8.28.

Example 9 (26): 2-[(2R,4aR,5S,6S,7aS)-6-hydroxy-5-{[3-(methoxymethyl)-4-methylphenoxy]methyl}octahydrocyclopenta[b]pyran-2-yl]-1,3-thiazole-4-carboxylic acid (Compound 9-26)

TLC: Rf 0.50 (dichloromethane:methanol=10:1) COOH Silica plate;
$^1$H-NMR (CDCl$_3$): δ 1.48-1.61, 1.93-2.30, 2.40-2.58, 3.48, 4.14, 4.32, 4.41, 4.64, 5.09, 6.76, 6.95, 7.06, 8.27.

Example 9 (27): 2-[(2R,4aR,5S,6S,7aS)-6-hydroxy-5-{[4-(methoxymethyl)-3-methylphenoxy]methyl}octahydrocyclopenta[b]pyran-2-yl]-1,3-thiazole-4-carboxylic acid (Compound 9-27)

TLC: Rf 0.50 (dichloromethane:methanol=10:1) COOH Silica plate;
$^1$H-NMR (CDCl$_3$): δ 1.48-1.61, 1.93-2.35, 2.41-2.56, 3.36, 4.13, 4.31, 4.39, 4.64, 5.10, 6.68-6.78, 7.20, 8.27.

Example 9 (28): 2-[(2R,4aR,5S,6S,7aS)-6-hydroxy-5-({4-methyl-3-[(E)-1-propen-1-yl]phenoxy}methyl)octahydrocyclopenta[b]pyran-2-yl]-1,3-thiazole-4-carboxylic acid (Compound 9-28)

TLC: Rf 0.48 (dichloromethane:methanol=10:1) COOH Silica plate;
$^1$H-NMR (CDCl$_3$): δ 1.49-1.62, 1.90, 1.95-2.31, 2.42-2.57, 4.14, 4.31, 4.65, 5.10, 6.10, 6.54, 6.70, 6.96, 7.02, 8.27.

Example 9 (29): 2-[(2R,4aR,5S,6S,7aS)-6-hydroxy-5-{[3-methoxy-4-(methoxymethyl)phenoxy]methyl}octahydrocyclopenta[b]pyran-2-yl]-1,3-thiazole-4-carboxylic acid (Compound 9-29)

TLC: Rf 0.45 (dichloromethane:methanol=10:1) COOH Silica plate;
$^1$H-NMR (CDCl$_3$): δ 1.48-1.61, 1.93-2.33, 2.41-2.56, 3.38, 3.82, 4.15, 4.32, 4.42, 4.66, 5.10, 6.46, 6.50, 7.21, 8.27.

Example 9 (30): 2-{(2R,4aR,5S,6S,7aS)-5-[(4-chloro-3-pentylphenoxy)methyl]-6-hydroxyoctahydrocyclopenta[b]pyran-2-yl}-1,3-thiazole-4-carboxylic acid (Compound 9-30)

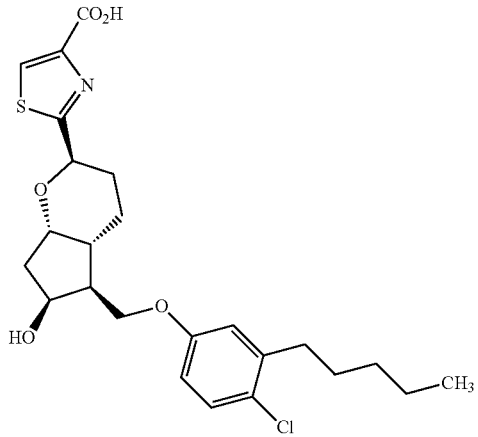 [SMILES: CCCCCc1cc(OC[C@@H]2[C@H]3CC[C@H](c4nc(C(=O)O)cs4)O[C@H]3C[C@@H]2O)ccc1Cl]

TLC: Rf 0.43 (chloroform:methanol:acetic acid=90:10:1);
$^1$H-NMR (CDCl$_3$): δ 0.85-0.98, 1.30-1.46, 1.50-1.69, 1.98-2.37, 2.42-2.58, 2.67, 4.04-4.19, 4.29-4.38, 4.64, 5.10, 6.69, 6.78, 7.22, 8.28.

Example 9 (31): 2-[(2R,4aR,5S,6S,7aS)-6-hydroxy-5-{[4-methyl-3-(1-propyn-1-yl)phenoxy]methyl}octahydrocyclopenta[b]pyran-2-yl]-1,3-thiazole-4-carboxylic acid (Compound 9-31)

TLC: Rf 0.50 (dichloromethane:methanol=4:1);
$^1$H-NMR (CDCl$_3$): δ 1.55-1.62, 2.04-2.11, 2.09, 2.14, 2.28, 2.34, 2.48, 4.12, 4.31, 4.63, 5.09, 6.75, 6.94, 7.05, 8.27.

Example 9 (32): 2-[(2R,4aR,5S,6S,7aS)-5-({3-[(dimethylamino)methyl]-4-methylphenoxy}methyl)-6-hydroxyoctahydrocyclopenta[b]pyran-2-yl]-1,3-thiazole-4-carboxylic acid (Compound 9-32)

TLC: Rf 0.53 (ethyl acetate) DIOL Silica plate;
$^1$H-NMR (DMSO-d$_6$): δ 1.54, 1.91, 2.15, 2.20, 2.26, 2.42, 2.71, 3.16, 3.86, 4.11, 4.19, 4.28, 4.62, 5.06, 6.70, 6.81, 7.03, 8.36.

Example 9 (33): 2-{((2R,4aR,5S,6S,7aS)-6-hydroxy-5-[(6,7,8,9-tetrahydro-5H-benzo[7]annulen-2-yloxy)methyl]octahydrocyclopenta[b]pyran-2-yl}-1,3-thiazole-4-carboxylic acid (Compound 9-33)

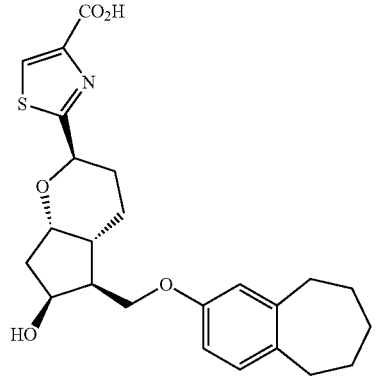 [SMILES: O=C(O)c1csc([C@H]2CC[C@@H]3[C@@H](COc4ccc5c(c4)CCCCC5)[C@@H](O)C[C@@H]3O2)n1]

TLC: Rf 0.48 (chloroform:methanol:acetic acid=90:10:1);
$^1$H-NMR (CDCl$_3$): δ 1.50-1.69, 1.78-1.87, 1.95-2.31, 2.48, 2.70-2.79, 4.12, 4.31, 4.65, 5.10, 6.63, 6.69, 6.99, 8.28.

Example 9 (34): 2-[(2R,4aR,5S,6S,7aS)-5-{[4-ethyl-3-(ethylthio)phenoxy]methyl}-6-hydroxyoctahydrocyclopenta[b]pyran-2-yl]-1,3-thiazole-4-carboxylic acid (Compound 9-34)

TLC: Rf 0.23 (chloroform:methanol:acetic acid=90:10:1);
$^1$H-NMR (CDCl$_3$): δ 1.20, 1.34, 1.50-1.63, 1.96-2.35, 2.43-2.55, 2.69, 2.92, 4.10-4.16, 4.32, 4.65, 5.10, 6.69, 6.84, 7.08, 8.28.

Example 9 (35): 2-{(2R,4aR,5S,6S,7aS)-5-[(3-cyclopropyl-4-ethylphenoxy)methyl]-6-hydroxyoctahydrocyclopenta[b]pyran-2-yl}-1,3-thiazole-4-carboxylic acid (Compound 9-35)

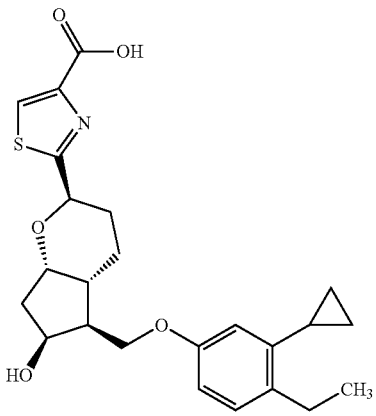 [SMILES: CCc1ccc(OC[C@@H]2[C@H]3CC[C@H](c4nc(C(=O)O)cs4)O[C@H]3C[C@@H]2O)cc1C1CC1]

TLC: Rf 0.55 (chloroform:methanol:acetic acid=90:10:1);
$^1$H-NMR (CDCl$_3$): δ 0.65, 0.93, 1.23, 1.49-1.62, 1.89-2.34, 2.41-2.52, 4.11, 4.32, 4.65, 5.11, 6.53, 6.70, 7.07, 8.30.

Example 9 (36): 2-{(2R,4aR,5S,6S,7aS)-5-[(3-cyclobutyl-4-ethylphenoxy)methyl]-6-hydroxyoctahydrocyclopenta[b]pyran-2-yl}-1,3-thiazole-4-carboxylic acid (Compound 9-36)

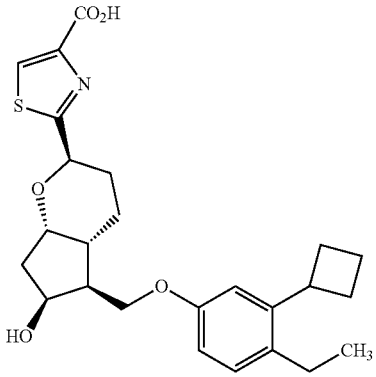 [SMILES: CCc1ccc(OC[C@@H]2[C@H]3CC[C@H](c4nc(C(=O)O)cs4)O[C@H]3C[C@@H]2O)cc1C1CCC1]

TLC: Rf 0.26 (chloroform:methanol:acetic acid=90:10:1);
$^1$H-NMR (CDCl$_3$): δ 1.17, 1.51-1.67, 1.79-1.90, 1.95-2.38, 2.44-2.61, 3.67, 4.16, 4.33, 4.67, 5.11, 6.72, 6.87, 7.06, 8.30.

Example 9 (37): 2-{(2R,4aR,5S,6S,7aS)-5-[(2',3'-dihydrospiro[cyclopropane-1,1'-inden]-6'-yloxy)methyl]-6-hydroxyoctahydrocyclopenta[b]pyran-2-yl}-1,3-thiazole-4-carboxylic acid (Compound 9-37)

TLC: Rf 0.22 (chloroform:methanol:acetic acid=90:10:1);
$^1$H-NMR (CDCl$_3$): δ 0.83-0.98, 1.51-1.63, 1.95-2.34, 2.41-2.54, 2.97, 4.11, 4.32, 4.64, 5.10, 6.23, 6.68, 7.09, 8.30.

Example 9 (38): 2-{(2R,4aR,5S,6S,7aS)-5-[(3',4'-dihydro-2'H-spiro[cyclopropane-1,1'-naphthalen]-7'-yloxy)methyl]-6-hydroxyoctahydrocyclopenta[b]pyran-2-yl}-1,3-thiazole-4-carboxylic acid (Compound 9-38)

TLC: Rf 0.35 (chloroform:methanol:acetic acid=90:10:1);
$^1$H-NMR (CDCl$_3$): δ 0.77-0.85, 0.92-0.99, 1.40-1.58, 1.60-1.67, 1.82-2.30, 2.37-2.51, 2.81, 4.07, 4.30, 4.61, 5.07, 6.21, 6.64, 6.97, 8.24.

Example 9 (39): 2-[(2R,4aR,5S,6S,7aS)-5-{[3-(cyclopropylmethyl)-4-ethylphenoxy]methyl}-6-hydroxyoctahydrocyclopenta[b]pyran-2-yl]-1,3-thiazole-4-carboxylic acid (Compound 9-39)

TLC: Rf 0.35 (chloroform:methanol:acetic acid=90:10:1);
$^1$H-NMR (CDCl$_3$): δ 0.18-0.24, 0.53-0.60, 0.98, 1.18, 1.48-1.61, 1.95-2.32, 2.42-2.63, 4.14, 4.32, 4.64, 5.10, 6.74, 6.94, 7.09, 8.27.

Example 9 (40): 2-[(2R,4aR,5S,6S,7aS)-6-hydroxy-5-{[(1-methyl-1,2,3,4-tetrahydro-7-quinolinyl)oxy]methyl}octahydrocyclopenta[b]pyran-2-yl]-1,3-thiazole-4-carboxylic acid (Compound 9-40)

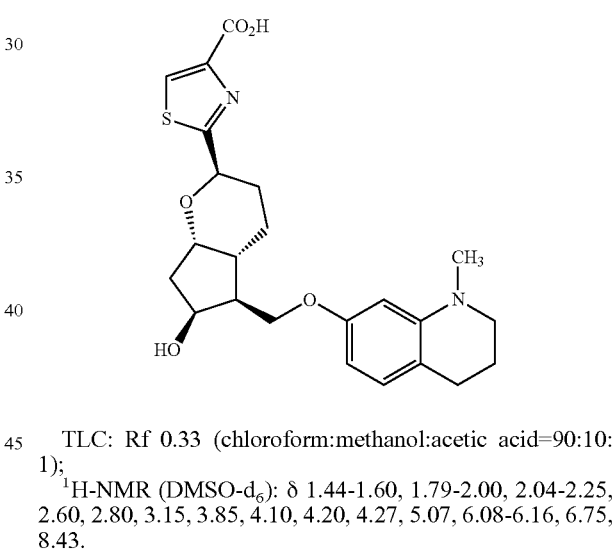

TLC: Rf 0.33 (chloroform:methanol:acetic acid=90:10:1);
$^1$H-NMR (DMSO-d$_6$): δ 1.44-1.60, 1.79-2.00, 2.04-2.25, 2.60, 2.80, 3.15, 3.85, 4.10, 4.20, 4.27, 5.07, 6.08-6.16, 6.75, 8.43.

Example 9 (41): 2-{(2R,4aR,5S,6S,7aS)-5-[(5,6,7,8,9,10-hexahydrobenzo[8]annulen-2-yloxy)methyl]-6-hydroxyoctahydrocyclopenta[b]pyran-2-yl}-1,3-thiazole-4-carboxylic acid (Compound 9-41)

TLC: Rf 0.53 (chloroform:methanol:acetic acid=90:10:1);
$^1$H-NMR (CDCl$_3$): δ 1.30-1.42, 1.50-1.74, 1.99-2.34, 2.43-2.56, 2.66-2.77, 4.14, 4.32, 4.66, 5.11, 6.67-6.73, 7.02, 8.30.

Example 9 (42): 2-{(2R,4aR,5S,6S,7aS)-5-[(3-cyclopentyl-4-ethylphenoxy)methyl]-6-hydroxyoctahydrocyclopenta[b]pyran-2-yl}-1,3-thiazole-4-carboxylic acid (Compound 9-42)

TLC: Rf 0.53 (chloroform:methanol:acetic acid=90:10:1);

¹H-NMR (CDCl₃): δ 1.19, 1.50-1.90, 1.99-2.34, 2.43-2.56, 2.64, 3.19, 4.14, 4.32, 4.66, 5.11, 6.70, 6.83, 7.07, 8.30.

Example 9 (43): 2-{(2R,4aR,5S,6S,7aS)-5-[(4-cyclobutyl-3-cyclopropylphenoxy)methyl]-6-hydroxyoctahydrocyclopenta[b]pyran-2-yl}-1,3-thiazole-4-carboxylic acid (Compound 9-43)

TLC: Rf 0.57 (chloroform:methanol:acetic acid=90:10:1);
¹H-NMR (CDCl₃): δ 0.58-0.67, 0.85-0.95, 1.50-1.64, 1.79-2.55, 3.85, 4.11, 4.32, 4.64, 5.10, 6.53, 6.74, 7.16, 8.29.

Example 9 (44): 2-{(2R,4aR,5S,6S,7aS)-5-[(3-cyclobutyl-4-cyclopropylphenoxy)methyl]-6-hydroxyoctahydrocyclopenta[b]pyran-2-yl}-1,3-thiazole-4-carboxylic acid (Compound 9-44)

TLC: Rf 0.57 (chloroform:methanol:acetic acid=90:10:1);
¹H-NMR (CDCl₃): δ 0.52-0.61, 0.80-0.91, 1.50-1.66, 1.75-2.60, 3.92, 4.15, 4.33, 4.66, 5.11, 6.66, 6.84, 6.91, 8.29.

Example 9 (45): 2-[(2R,4aR,5R,6S,7aS)-5-{[(3-cyclopropyl-4-ethylphenyl)thio]methyl}-6-hydroxyoctahydrocyclopenta[b]pyran-2-yl]-1,3-thiazole-4-carboxylic acid (Compound 9-45)

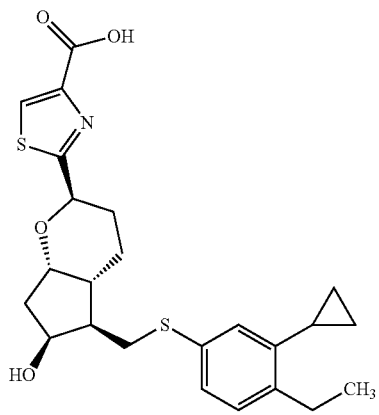 [SMILES: CCc1ccc(SC[C@@H]2[C@H]3CC[C@H](c4nc(C(=O)O)cs4)O[C@H]3C[C@@H]2O)cc1C1CC1]

TLC: Rf 0.48 (dichloromethane:methanol=4:1);
¹H-NMR (CDCl₃): δ 0.67, 0.96, 1.25, 1.51, 1.86-1.99, 2.01-2.28, 2.80, 2.95, 3.11, 4.27, 4.52, 5.05, 7.00, 7.11, 7.17, 8.28.

Example 10: (2R,4aR,5S,6S,7aS)-5-[(3,4-dicyclopropylphenoxy)methyl]-2-[4-(hydroxymethyl)-1,3-thiazol-2-yl]octahydrocyclopenta[b]pyran-6-ol (Compound 10)

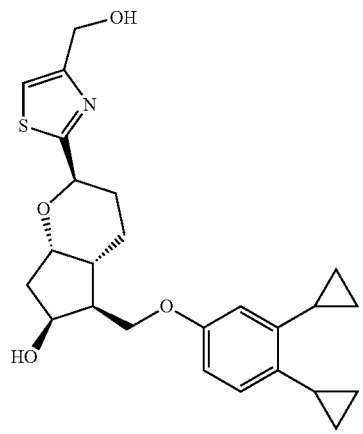 [SMILES: OCc1csc([C@H]2CC[C@@H]3[C@@H](COc4ccc(C5CC5)c(C5CC5)c4)[C@@H](O)C[C@@H]3O2)n1]

Tetrahydrofuran (0.36 mL) and lithium borohydride (2.0 mg) were added to compound D (9.0 mg) under argon stream, and then methanol (3.6 μL) was added dropwise to the mixed solution, and the resulting solution was stirred at 50° C. for 2 hours. A 1 M aqueous hydrochloric acid solution was added to the reaction solution, and the reaction solution was extracted with ethyl acetate. The organic layer was washed with a saturated aqueous sodium hydrogen carbonate solution and saturated brine, then dried over anhydrous magnesium sulfate, and then filtrated. The filtrate was concentrated under reduced pressure, and the residue was purified by silica gel column chromatography (hexane:ethyl acetate=4:6→0:100→ethyl acetate:methanol=95:5) to produce the title compound (5.4 mg) having the following physical property values.

TLC: Rf 0.15 (hexane:ethyl acetate=2:8);
¹H-NMR (CDCl₃): δ 0.59-0.70, 0.86-1.00, 1.49-1.62, 1.93-2.26, 2.44-2.57, 4.09, 4.34, 4.63, 4.75, 5.08, 6.51, 6.65, 6.91, 7.18.

Examples 10 (1) to (42)

The same procedures as in Example A→Example C→Example D→Example 10 were carried out except that, in place of 3,5-difluorophenol, a corresponding substituted phenol was used. In this manner, the following compounds were produced.

Example 10 (1): (2R,4aR,5S,6S,7aS)-5-[(2,3-di-hydro-1H-inden-5-yloxy)methyl]-2-[4-(hydroxymethyl)-1,3-thiazol-2-yl]octahydrocyclopenta[b]pyran-6-ol (Compound 10-1)

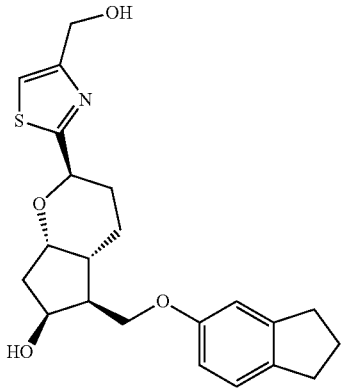 [SMILES: OCc1csc([C@H]2CC[C@@H]3[C@@H](COc4ccc5c(c4)CCC5)[C@@H](O)C[C@@H]3O2)n1]

TLC: Rf 0.10 (hexane:ethyl acetate=1:1);
$^1$H-NMR (CDCl$_3$): δ 1.50-1.68, 1.93-2.27, 2.43-2.58, 2.79-2.92, 3.91, 4.12, 4.33, 4.65, 4.76, 5.08, 6.71, 6.81, 7.11, 7.18.

Example 10 (2): (2R,4aR,5S,6S,7aS)-5-[(4-chloro-3-methylphenoxy)methyl]-2-[4-(hydroxymethyl)-1,3-thiazol-2-yl]octahydrocyclopenta[b]pyran-6-ol (Compound 10-2)

TLC: Rf 0.62 (ethyl acetate);
$^1$H-NMR (CDCl$_3$): δ 1.57, 1.87, 1.91-2.09, 2.20, 2.32, 2.51, 4.08, 4.13, 4.34, 4.64, 4.76, 5.09, 6.70, 6.81, 7.19, 7.22.

Example 10 (3): (2R,4aR,5S,6S,7aS)-5-[(3-ethyl-4-methylphenoxy)methyl]-2-[4-(hydroxymethyl)-1,3-thiazol-2-yl]octahydrocyclopenta[b]pyran-6-ol (Compound 10-3)

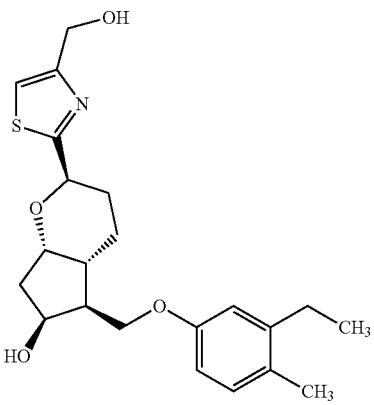 [SMILES: CCc1cc(OC[C@@H]2[C@H]3CC[C@H](c4nc(CO)cs4)O[C@H]3C[C@@H]2O)ccc1C]

TLC: Rf 0.45 (ethyl acetate);
$^1$H-NMR (CDCl$_3$): δ 1.20, 1.57, 1.93-2.10, 2.12-2.21, 2.23, 2.52, 2.59, 4.12, 4.33, 4.65, 4.76, 5.08, 6.67, 6.74, 7.04, 7.18.

Example 10 (4): (2R,4aR,5S,6S,7aS)-5-[(4-ethyl-3-methylphenoxy)methyl]-2-[4-(hydroxymethyl)-1,3-thiazol-2-yl]octahydrocyclopenta[b]pyran-6-ol (Compound 10-4)

TLC: Rf 0.36 (hexane:ethyl acetate=1:2);
$^1$H-NMR (CDCl$_3$): δ 1.18, 1.58, 1.96, 1.97-2.13, 2.19, 2.28, 2.50, 2.56, 4.12, 4.34, 4.64, 4.75, 5.08, 6.70, 6.73, 7.05, 7.18.

Example 10 (5): (2R,4aR,5S,6S,7aS)-5-[(4-chloro-3-cyclopropylphenoxy)methyl]-2-[4-(hydroxymethyl)-1,3-thiazol-2-yl]octahydrocyclopenta[b]pyran-6-ol (Compound 10-5)

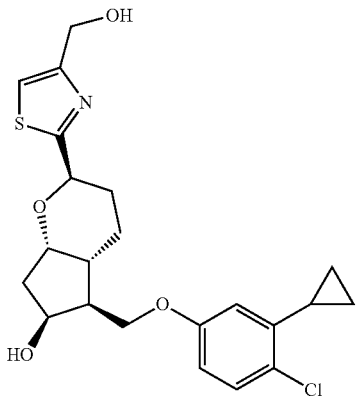 [SMILES: OCc1csc([C@H]2CC[C@@H]3[C@@H](COc4ccc(Cl)c(C5CC5)c4)[C@@H](O)C[C@@H]3O2)n1]

TLC: Rf 0.64 (ethyl acetate);
$^1$H-NMR (CDCl$_3$): δ 0.69, 1.01, 1.53, 1.87, 1.92-2.23, 2.50, 4.07, 4.15, 4.32, 4.63, 4.78, 5.09, 6.49, 6.67, 7.18, 7.24.

Example 10 (6): (2R,4aR,5S,6S,7aS)-5-[(3-cyclopropyl-4-methylphenoxy)methyl]-2-[4-(hydroxymethyl)-1,3-thiazol-2-yl]octahydrocyclopenta[b]pyran-6-ol (Compound 10-6)

TLC: Rf 0.51 (ethyl acetate);
$^1$H-NMR (CDCl$_3$): δ 0.62, 0.92, 1.57, 1.71, 1.82, 1.92-2.13, 2.15-2.29, 2.34, 2.43, 2.71, 3.90, 4.02, 4.17, 4.26, 4.78, 5.20, 6.46, 6.62, 7.01, 7.21.

Example 10 (7): (2R,4aR,5S,6S,7aS)-2-[4-(hydroxymethyl)-1,3-thiazol-2-yl]-5-[(5,6,7,8-tetrahydro-2-naphthalenyloxy)methyl]octahydrocyclopenta[b]pyran-6-ol (Compound 10-7)

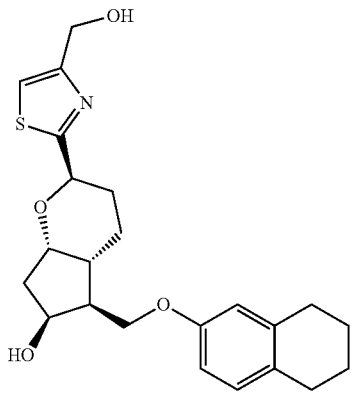 [SMILES: OCc1csc([C@H]2CC[C@@H]3[C@@H](COc4ccc5c(c4)CCCC5)[C@@H](O)C[C@@H]3O2)n1]

TLC: Rf 0.60 (ethyl acetate);
$^1$H-NMR (CDCl$_3$): δ 1.56, 1.77, 1.92-2.07, 2.15-2.22, 2.50, 2.71, 4.11, 4.34, 4.64, 4.76, 5.08, 6.64, 6.68, 6.97, 7.18.

Example 10 (8): (2R,4aR,5S,6S,7aS)-5-[(3-chloro-4-fluorophenoxy)methyl]-2-[4-(hydroxymethyl)-1,3-thiazol-2-yl]octahydrocyclopenta[b]pyran-6-ol (Compound 10-8)

TLC: Rf 0.46 (ethyl acetate);
$^1$H-NMR (CDCl$_3$): δ 1.59, 1.93-2.03, 2.07-2.24, 2.52, 4.04, 4.13, 4.33, 4.63, 4.76, 5.09, 6.77, 6.95, 7.05, 7.18.

Example 10 (9): (2R,4aR,5S,6S,7aS)-2-[4-(hydroxymethyl)-1,3-thiazol-2-yl]-5-[(3-methoxy-4-methylphenoxy)methyl]octahydrocyclopenta[b]pyran-6-ol (Compound 10-9)

TLC: Rf 0.32 (ethyl acetate:hexane=2:1);
$^1$H-NMR (CDCl$_3$): δ 1.55-1.63, 1.93-2.25, 2.46-2.58, 3.80, 4.14, 4.34, 4.66, 4.76, 5.09, 6.40-6.45, 7.02, 7.19.

Example 10 (10): (2R,4aR,5S,6S,7aS)-2-[4-(hydroxymethyl)-1,3-thiazol-2-yl]-5-[(4-methyl-3-propylphenoxy)methyl]octahydrocyclopenta[b]pyran-6-ol (Compound 10-10)

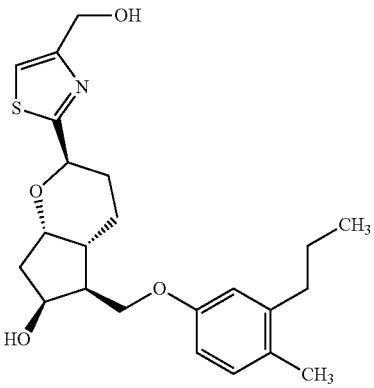 [SMILES: CCCc1cc(OC[C@@H]2[C@H]3CC[C@H](c4nc(CO)cs4)O[C@H]3C[C@@H]2O)ccc1C]

TLC: Rf 0.40 (ethyl acetate:hexane=2:1);
$^1$H-NMR (CDCl$_3$): δ 0.99, 1.50-1.70, 1.94-2.24, 2.46-2.58, 4.12, 4.35, 4.66, 4.77, 5.09, 6.68, 6.73, 7.03, 7.19.

Example 10 (11): (2R,4aR,5S,6S,7aS)-2-[4-(hydroxymethyl)-1,3-thiazol-2-yl]-5-{[3-methyl-4-(methylthio)phenoxy]methyl}octahydrocyclopenta[b]pyran-6-ol (Compound 10-11)

TLC: Rf 0.33 (ethyl acetate:hexane=2:1);
$^1$H-NMR (CDCl$_3$): δ 1.50-1.63, 1.94-2.25, 2.38, 2.40, 2.42-2.58, 4.13, 4.35, 4.65, 4.76, 5.09, 6.73-6.81, 7.16-7.22.

Example 10 (12): (2R,4aR,5S,6S,7aS)-2-[4-(hydroxymethyl)-1,3-thiazol-2-yl]-5-{[4-methyl-3-(methylthio)phenoxy]methyl}octahydrocyclopenta[b]pyran-6-ol (Compound 10-12)

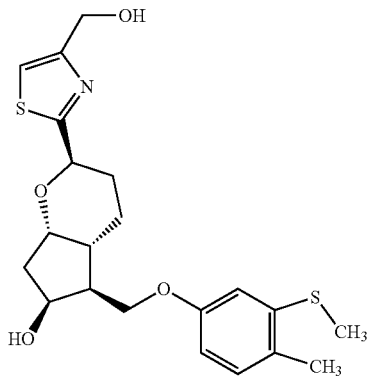 [SMILES: CSc1cc(OC[C@@H]2[C@H]3CC[C@H](c4nc(CO)cs4)O[C@H]3C[C@@H]2O)ccc1C]

TLC: Rf 0.73 (ethyl acetate);
$^1$H-NMR (CDCl$_3$): δ 1.48-1.61, 1.93-2.23, 2.26, 2.46, 2.47-2.58, 4.12, 4.34, 4.65, 4.76, 5.09, 6.62, 6.72, 7.03, 7.18.

Example 10 (13): (2R,4aR,5S,6S,7aS)-2-[4-(hydroxymethyl)-1,3-thiazol-2-yl]-5-{([4-(methoxymethyl)-3-methylphenoxy]methyl}octahydrocyclopenta[b]pyran-6-ol (Compound 10-13)

TLC: Rf 0.56 (ethyl acetate);
$^1$H-NMR (CDCl$_3$): δ 1.48-1.61, 1.91-2.39, 2.43-2.58, 3.36, 4.13, 4.34, 4.39, 4.64, 4.75, 5.08, 6.73, 6.75, 7.16-7.23.

Example 10 (14): (2R,4aR,5S,6S,7aS)-2-[4-(hydroxymethyl)-1,3-thiazol-2-yl]-5-({4-methyl-3-[(1E)-1-propen-1-yl]phenoxy}methyl)octahydrocyclopenta[b]pyran-6-ol (Compound 10-14)

TLC: Rf 0.65 (ethyl acetate);
$^1$H-NMR (CDCl$_3$): δ 1.49-1.62, 1.84-2.31, 2.44-2.58, 4.11, 4.34, 4.65, 4.76, 5.08, 6.09, 6.53, 6.70, 6.96, 7.02, 7.18.

Example 10 (15): (2R,4aR,5S,6S,7aS)-5-[(3-cyclopropyl-4-ethylphenoxy)methyl]-2-[4-(hydroxymethyl)-1,3-thiazol-2-yl]octahydrocyclopenta[b]pyran-6-ol (Compound 10-15)

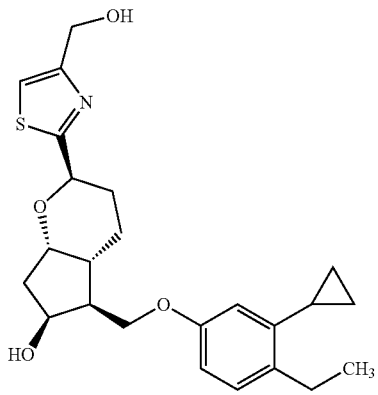 [SMILES: CCc1ccc(OC[C@@H]2[C@H]3CC[C@H](c4nc(CO)cs4)O[C@H]3C[C@@H]2O)cc1C1CC1]

TLC: Rf 0.56 (ethyl acetate);
$^1$H-NMR (CDCl$_3$): δ 0.65, 0.94, 1.24, 1.51-1.62, 1.89-2.01, 2.06-2.10, 2.10-2.23, 2.50, 2.77, 4.11, 4.35, 4.65, 4.77, 5.09, 6.53, 6.71, 7.08, 7.19.

Example 10 (16): (2R,4aR,5S,6S,7aS)-2-[4-(hydroxymethyl)-1,3-thiazol-2-yl]-5-[(6,7,8,9-tetrahydro-5H-benzo[7]annulen-2-yloxy)methyl]octahydrocyclopenta[b]pyran-6-ol (Compound 10-16)

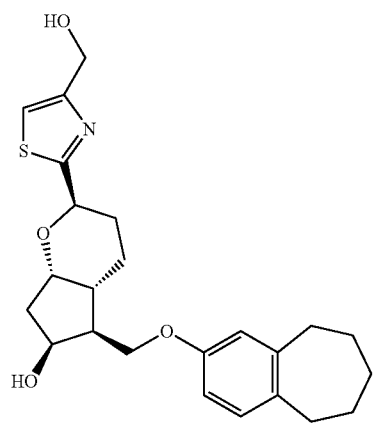 [SMILES: OCc1csc([C@H]2CC[C@@H]3[C@@H](COc4ccc5c(c4)CCCCC5)[C@@H](O)C[C@@H]3O2)n1]

TLC: Rf 0.41 (hexane:ethyl acetate=2:8);
$^1$H-NMR (CDCl$_3$): δ 1.50-1.69, 1.78-1.87, 1.94-2.28, 2.32, 2.46-2.57, 2.70-2.79, 4.12, 4.34, 4.65, 4.76, 5.09, 6.64, 6.71, 7.01, 7.19.

Example 10 (17): (2R,4aR,5S,6S,7aS)-5-[(3-cyclobutyl-4-ethylphenoxy)methyl]-2-[4-(hydroxymethyl)-1,3-thiazol-2-yl]octahydrocyclopenta[b]pyran-6-ol (Compound 10-17)

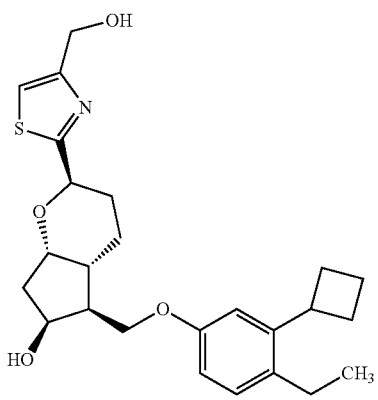 [SMILES: CCc1ccc(OC[C@@H]2[C@H]3CC[C@H](c4nc(CO)cs4)O[C@H]3C[C@@H]2O)cc1C1CCC1]

TLC: Rf 0.35 (hexane:ethyl acetate=1:4);
$^1$H-NMR (CDCl$_3$): δ 1.17, 1.55, 1.86, 1.94-2.25, 2.32, 2.55, 3.67, 4.16, 4.36, 4.66, 4.77, 5.10, 6.72, 6.88, 7.06, 7.19.

Example 10 (18): (2R,4aR,5S,6S,7aS)-5-[(2',3'-dihydrospiro[cyclopropane-1,1'-inden]-6'-yloxy)methyl]-2-[4-(hydroxymethyl)-1,3-thiazol-2-yl]octahydrocyclopenta[b]pyran-6-ol (Compound 10-18)

TLC: Rf 0.31 (hexane:ethyl acetate=1:4);
$^1$H-NMR (CDCl$_3$): δ 0.90, 1.50-1.61, 1.92-2.09, 2.10-2.23, 2.50, 2.97, 4.10, 4.34, 4.77, 5.09, 6.23, 6.68, 7.09, 7.19.

Example 10 (19): (2R,4aR,5S,6S,7aS)-5-{[3-(cyclopropylmethyl)-4-ethylphenoxy]methyl}-2-[4-(hydroxymethyl)-1,3-thiazol-2-yl]octahydrocyclopenta[b]pyran-6-ol (Compound 10-19)

TLC: Rf 0.38 (hexane:ethyl acetate=1:4);
$^1$H-NMR (CDCl$_3$): δ 0.21, 0.57, 0.99, 1.19, 1.49-1.62, 1.94-2.24, 2.54, 2.59, 4.15, 4.35, 4.67, 4.77, 5.09, 6.75, 6.94, 7.09, 7.19.

Example 10 (20): (2R,4aR,5S,6S,7aS)-2-[4-(hydroxymethyl)-1,3-thiazol-2-yl]-5-{[(1-methyl-1,2,3,4-tetrahydro-7-quinolinyl)oxy]methyl}octahydrocyclopenta[b]pyran-6-ol (Compound 10-20)

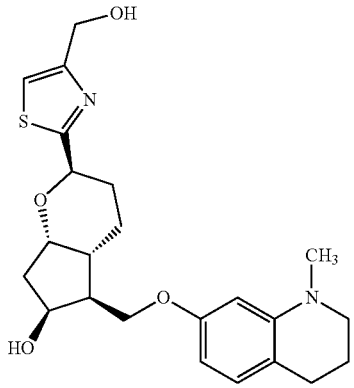 [SMILES: CN1CCCc2ccc(OC[C@@H]3[C@H]4CC[C@H](c5nc(CO)cs5)O[C@H]4C[C@@H]3O)cc21]

TLC: Rf 0.48 (ethyl acetate);
$^1$H-NMR (CDCl$_3$): δ 1.50-1.62, 1.91-2.03, 2.05-2.24, 2.49, 2.70, 2.87, 3.21, 4.12, 4.35, 4.67, 4.76, 5.09, 6.16, 6.19, 6.85, 7.19.

Example 10 (21): (2R,4aR,5S,6S,7aS)-5-[(3-chloro-4-methylphenoxy)methyl]-2-[4-(hydroxymethyl)-1,3-thiazol-2-yl]octahydrocyclopenta[b]pyran-6-ol (Compound 10-21)

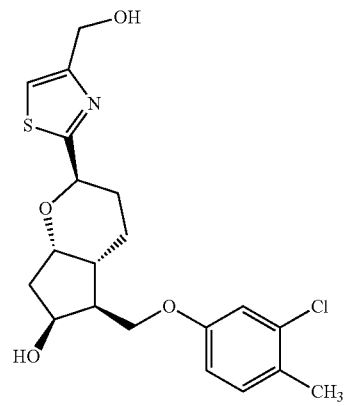 [SMILES: Cc1ccc(OC[C@@H]2[C@H]3CC[C@H](c4nc(CO)cs4)O[C@H]3C[C@@H]2O)cc1Cl]

TLC: Rf 0.19 (hexane:ethyl acetate=3:7);
$^1$H-NMR (CDCl$_3$): δ 1.50-1.72, 1.93-2.27, 2.30, 2.43-2.58, 4.05-4.18, 4.34, 4.64, 4.76, 5.09, 6.74, 6.95, 7.11, 7.19.

Example 10 (22): (2R,4aR,5S,6S,7aS)-5-{[(4-fluoro-2,3-dihydro-1H-inden-5-yl)oxy]methyl}-2-[4-(hydroxymethyl)-1,3-thiazol-2-yl]octahydrocyclopenta[b]pyran-6-ol (Compound 10-22)

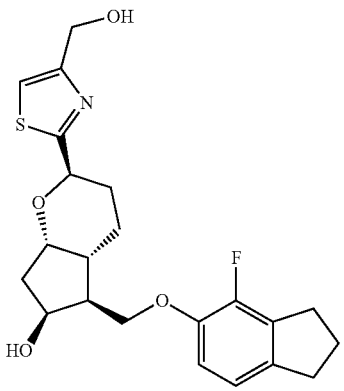 [SMILES: OCc1csc([C@H]2CC[C@@H]3[C@@H](COc4ccc5c(c4F)CCC5)[C@@H](O)C[C@@H]3O2)n1]

TLC: Rf 0.32 (hexane:ethyl acetate=1:2);
$^1$H-NMR (CDCl$_3$): δ 1.50-1.63, 1.93-2.05, 2.11, 2.17-2.24, 2.54, 2.87, 2.93, 4.17, 4.34, 4.68, 4.75, 5.08, 6.81, 6.85, 7.18.

Example 10 (23): (2R,4aR,5S,6S,7aS)-5-[(3-chloro-4-ethylphenoxy)methyl]-2-[4-(hydroxymethyl)-1,3-thiazol-2-yl]octahydrocyclopenta[b]pyran-6-ol (Compound 10-23)

TLC: Rf 0.62 (ethyl acetate);
$^1$H-NMR (CDCl$_3$): δ 1.20, 1.56, 1.93-2.23, 2.51, 2.68, 4.05-4.16, 4.33, 4.64, 4.76, 5.09, 6.77, 6.93, 7.12, 7.18.

Example 10 (24): (2R,4aR,5S,6S,7aS)-5-[(4-chloro-3-fluorophenoxy)methyl]-2-[4-(hydroxymethyl)-1,3-thiazol-2-yl]octahydrocyclopenta[b]pyran-6-ol (Compound 10-24)

TLC: Rf 0.53 (ethyl acetate);
$^1$H-NMR (CDCl$_3$): δ 1.69, 1.94-2.03, 2.05-2.23, 2.52, 4.05, 4.15, 4.34, 4.63, 4.76, 5.09, 5.29, 6.74, 7.18, 7.27.

Example 10 (25): (2R,4aR,5S,6S,7aS)-5-[(4-fluoro-3-methylphenoxy)methyl]-2-[4-(hydroxymethyl)-1,3-thiazol-2-yl]octahydrocyclopenta[b]pyran-6-ol (Compound 10-25)

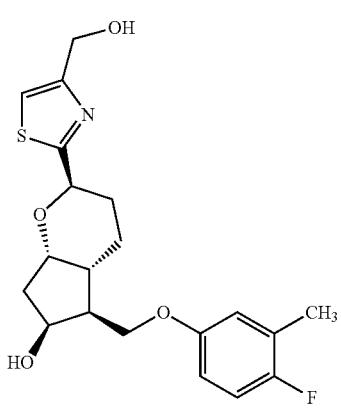 [SMILES: Cc1cc(OC[C@@H]2[C@H]3CC[C@H](c4nc(CO)cs4)O[C@H]3C[C@@H]2O)ccc1F]

TLC: Rf 0.50 (ethyl acetate);
¹H-NMR (CDCl₃): δ 1.56, 1.98-2.08, 2.11-2.23, 2.25, 2.50, 4.07, 4.12, 4.34, 4.64, 4.76, 5.09, 6.67, 6.73, 6.90, 7.18.

Example 10 (26): (2R,4aR,5S,6S,7aS)-5-[(3-cyclopropyl-4-fluorophenoxy)methyl]-2-[4-(hydroxymethyl)-1,3-thiazol-2-yl]octahydrocyclopenta[b]pyran-6-ol (Compound 10-26)

TLC: Rf 0.54 (ethyl acetate);
¹H-NMR (CDCl₃): δ 0.70, 0.99, 1.55, 1.93, 1.97-2.10, 2.15-2.23, 2.49, 4.05, 4.10, 4.33, 4.63, 4.76, 5.08, 6.41, 6.64, 6.90, 7.18.

Example 10 (27): (2R,4aR,5S,6S,7aS)-5-[(3,4-dichlorophenoxy)methyl]-2-[4-(hydroxymethyl)-1,3-thiazol-2-yl]octahydrocyclopenta[b]pyran-6-ol (Compound 10-27)

TLC: Rf 0.50 (ethyl acetate);
¹H-NMR (CDCl₃): δ 1.59, 1.94-2.05, 2.09-2.24, 2.52, 4.07, 4.16, 4.35, 4.63, 4.76, 5.09, 6.79, 7.04, 7.19, 7.33.

Example 10 (28): (2R,4aR,5S,6S,7aS)-5-[(bicyclo[4.2.0]octa-1,3,5-trien-3-yloxy)methyl]-2-[4-(hydroxymethyl)-1,3-thiazol-2-yl]octahydrocyclopenta[b]pyran-6-ol (Compound 10-28)

TLC: Rf 0.50 (ethyl acetate);
¹H-NMR (CDCl₃): δ 1.55, 1.96, 2.01-2.10, 2.19, 2.51, 3.11, 4.11, 4.33, 4.65, 4.76, 5.09, 6.69, 6.75, 6.95, 7.18.

Example 10 (29): (2R,4aR,5S,6S,7aS)-5-[(4-ethyl-3-fluorophenoxy)methyl]-2-[4-(hydroxymethyl)-1,3-thiazol-2-yl]octahydrocyclopenta[b]pyran-6-ol (Compound 10-29)

TLC: Rf 0.33 (ethyl acetate:hexane=2:1);
¹H-NMR (CDCl₃): δ 1.19, 1.58, 1.89, 1.91-2.17, 2.23, 2.50, 2.61, 4.10, 4.34, 4.65, 4.74, 5.09, 6.61, 6.67, 7.09, 7.19.

Example 10 (30): (2R,4aR,5S,6S,7aS)-5-{[(7-fluoro-2,3-dihydro-1H-inden-5-yl)oxy]methyl}-2-[4-(hydroxymethyl)-1,3-thiazol-2-yl]octahydrocyclopenta[b]pyran-6-ol (Compound 10-30)

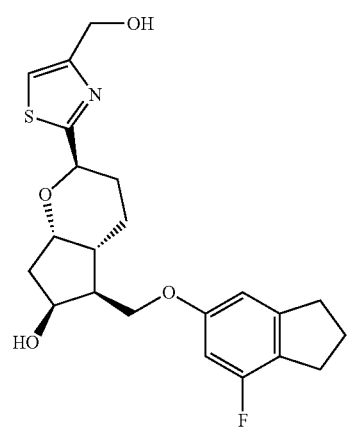 [SMILES: OCc1csc([C@H]2CC[C@@H]3[C@@H](COc4cc(F)c5c(c4)CCC5)[C@@H](O)C[C@@H]3O2)n1]

TLC: Rf 0.73 (ethyl acetate);
¹H-NMR (CDCl₃): δ 1.57, 1.89-2.02, 2.10, 2.12-2.25, 2.50, 2.91, 4.11, 4.33, 4.62, 4.75, 5.09, 6.43, 6.62, 7.19.

Example 10 (31): (2R,4aR,5S,6S,7aS)-5-[(2,3-dihydro-1-benzofuran-6-yloxy)methyl]-2-[4-(hydroxymethyl)-1,3-thiazol-2-yl]octahydrocyclopenta[b]pyran-6-ol (Compound 10-31)

TLC: Rf 0.26 (ethyl acetate:hexane=2:1);
¹H-NMR (CDCl₃): δ 1.50-1.66, 1.92-2.24, 2.43-2.57, 3.14, 4.10, 4.34, 4.58, 4.63, 4.77, 5.08, 6.38-6.44, 7.05, 7.18.

Example 10 (32): (2R,4aR,5S,6S,7aS)-5-[(3,4-diethylphenoxy)methyl]-2-[4-(hydroxymethyl)-1,3-thiazol-2-yl]octahydrocyclopenta[b]pyran-6-1 (Compound 10-32)

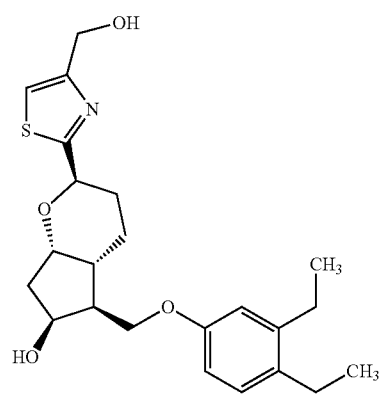 [SMILES: CCc1ccc(OC[C@@H]2[C@H]3CC[C@H](c4nc(CO)cs4)O[C@H]3C[C@@H]2O)cc1CC]

TLC: Rf 0.57 (hexane:ethyl acetate=1:2);
¹H-NMR (CDCl₃): δ 1.19, 1.22, 1.51-1.63, 1.93-2.05, 2.09, 2.16-2.23, 2.51, 2.59, 2.61, 4.14, 4.34, 4.65, 4.75, 5.08, 6.71, 6.75, 7.07, 7.18.

Example 10 (33): (2R,4aR,5S,6S,7aS)-5-[(4-fluoro-3-isopropylphenoxy)methyl]-2-[4-(hydroxymethyl)-1,3-thiazol-2-yl]octahydrocyclopenta[b]pyran-6-ol (Compound 10-33)

TLC: Rf 0.73 (ethyl acetate);
¹H-NMR (CDCl₃): δ 1.24, 1.49-1.62, 1.94-2.26, 2.43-2.58, 3.20, 4.10, 4.34, 4.66, 4.76, 5.09, 6.67, 6.77, 6.91, 7.18.

Example 10 (34): (2R,4aR,5S,6S,7aS)-2-[4-(hydroxymethyl)-1,3-thiazol-2-yl]-5-{[3-(methoxymethyl)-4-methylphenoxy]methyl}octahydrocyclopenta[b]pyran-6-ol (Compound 10-34)

¹H-NMR (CDCl₃): δ 1.48-1.61, 1.91-2.29, 2.41-2.58, 3.42, 4.14, 4.34, 4.41, 4.64, 4.75, 5.08, 6.76, 6.94, 7.06, 7.18.

Example 10 (35): (2R,4aR,5S,6S,7aS)-2-[4-(hydroxymethyl)-1,3-thiazol-2-yl]-5-{[3-methoxy-4-(methoxymethyl)phenoxy]methyl}octahydrocyclopenta[b]pyran-6-ol (Compound 10-35)

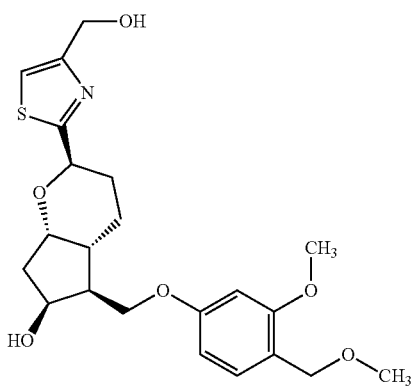 [SMILES: COCc1ccc(OC[C@@H]2[C@H]3CC[C@H](c4nc(CO)cs4)O[C@H]3C[C@@H]2O)cc1OC]

TLC: Rf 0.59 (ethyl acetate);
¹H-NMR (CDCl₃): δ 1.48-1.61, 1.91-2.27, 2.43-2.60, 3.38, 3.82, 4.14, 4.35, 4.42, 4.65, 4.75, 5.09, 6.46, 6.50, 7.19, 7.23.

Example 10 (36): (2R,4aR,5S,6S,7aS)-5-[(4-chloro-3-pentylphenoxy)methyl]-2-[4-(hydroxymethyl)-1,3-thiazol-2-yl]octahydrocyclopenta[b]pyran-6-ol (Compound 10-36)

TLC: Rf 0.22 (hexane:ethyl acetate=1:1);
¹H-NMR (CDCl₃): δ 0.86-0.98, 1.30-1.43, 1.50-1.69, 1.89-2.28, 2.42-2.58, 2.66, 4.03-4.19, 4.31-4.39, 4.64, 4.76, 5.08, 6.69, 6.78, 7.19, 7.23.

Example 10 (37): (2R,4aR,5S,6S,7aS)-2-[4-(hydroxymethyl)-1,3-thiazol-2-yl]-5-{[4-methyl-3-(1-propyn-1-yl)phenoxy]methyl}octahydrocyclopenta[b]pyran-6-ol (Compound 10-37)

TLC: Rf 0.48 (hexane:ethyl acetate=1:4);
¹H-NMR (CDCl₃): δ 1.52-1.62, 1.92-2.07, 2.09, 2.14-2.21, 2.34, 2.50, 4.11, 4.33, 4.63, 4.75, 5.08, 6.75, 6.94, 7.05, 7.18.

Example 10 (38): (2R,4aR,5S,6S,7aS)-5-({3-[(dimethylamino)methyl]-4-methylphenoxy}methyl)-2-[4-(hydroxymethyl)-1,3-thiazol-2-yl]octahydrocyclopenta[b]pyran-6-ol (Compound 10-38)

TLC: Rf 0.12 (ethyl acetate:methanol=4:1);
¹H-NMR (CDCl₃): δ 1.57, 1.92-2.10, 2.16-2.34, 2.25, 2.27, 2.51, 2.34, 4.13, 4.33, 4.63, 4.75, 5.08, 6.74, 6.90, 7.05, 7.18.

Example 10 (39): (2R,4aR,5S,6S,7aS)-5-{[4-ethyl-3-(ethylthio)phenoxy]methyl}-2-[4-(hydroxymethyl)-1,3-thiazol-2-yl]octahydrocyclopenta[b]pyran-6-ol (Compound 10-39)

TLC: Rf 0.52 (ethyl acetate);
¹H-NMR (CDCl₃): δ 1.20, 1.34, 1.50-1.63, 1.94-2.28, 2.43-2.57, 2.68, 2.92, 3.48, 4.12, 4.34, 4.65, 4.76, 5.09, 6.70, 6.85, 7.08, 7.18.

Example 10 (40): (2R,4aR,5S,6S,7aS)-5-[(3',4'-dihydro-2'H-spiro[cyclopropane-1,1'-naphthalen]-7'-yloxy)methyl]-2-[4-(hydroxymethyl)-1,3-thiazol-2-yl]octahydrocyclopenta[b]pyran-6-ol (Compound 10-40)

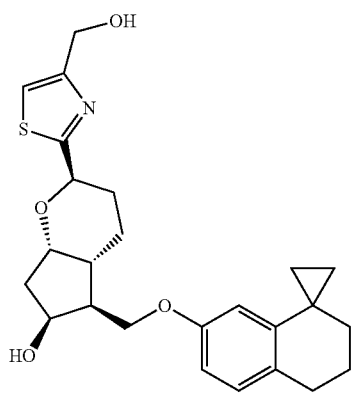 [SMILES: OCc1csc([C@H]2CC[C@@H]3[C@@H](COc4ccc5c(c4)C4(CCC5)CC4)[C@@H](O)C[C@@H]3O2)n1]

TLC: Rf 0.34 (hexane:ethyl acetate=1:4);
¹H-NMR (CDCl₃): δ 0.80, 0.94, 1.48-1.60, 1.66, 1.85, 1.98-2.10, 2.15-2.22, 2.50, 2.81, 4.09, 4.33, 4.64, 4.76, 5.09, 6.22, 6.64, 6.98, 7.19.

Example 10 (41): (2R,4aR,5S,6S,7aS)-5-[(5,6,7,8,9,10-hexahydrobenzo[8]annulen-2-yloxy)methyl]-2-[4-(hydroxymethyl)-1,3-thiazol-2-yl]octahydrocyclopenta[b]pyran-6-ol (Compound 10-41)

TLC: Rf 0.52 (hexane:ethyl acetate=2:8);
¹H-NMR (CDCl₃): δ 1.30-1.42, 1.50-1.73, 1.94-2.29, 2.43-2.57, 2.64-2.76, 4.13, 4.35, 4.66, 4.76, 5.09, 6.67-6.73, 7.01, 7.19.

Example 10 (42): (2R,4aR,5S,6S,7aS)-5-[(3-cyclopentyl-4-ethylphenoxy)methyl]-2-[4-(hydroxymethyl)-1,3-thiazol-2-yl]octahydrocyclopenta[b]pyran-6-ol (Compound 10-42)

TLC: Rf 0.51 (hexane:ethyl acetate=2:8);
¹H-NMR (CDCl₃): δ 1.18, 1.50-1.90, 1.92-2.30, 2.43-2.59, 2.64, 3.18, 4.13, 4.35, 4.66, 4.76, 5.09, 6.70, 6.83, 7.07, 7.19.

Examples 11 (1) to (6)

The same procedures as in Example A→Example C→Example D→Example 9→Example 3 were carried out except that 3,5-difluorophenol or a corresponding substituted phenol was used. In this manner, the following compounds were produced.

Example 11 (1): isopropyl 2-[(2R,4aR,5S,6S,7aS)-6-hydroxy-5-{[4-methyl-3-(methylthio)phenoxy]methyl}octahydrocyclopenta[b]pyran-2-yl]-1,3-thiazole-4-carboxylate (Compound 11-1)

TLC: Rf 0.41 (hexane:ethyl acetate, 1:1);
$^1$H-NMR (CDCl$_3$): δ 1.38, 1.51-1.59, 1.96-2.08, 2.15-2.23, 2.26, 2.46, 2.49, 4.10-4.15, 4.35, 4.64, 5.10, 5.26, 6.61, 6.72, 7.03, 8.12.

Example 11 (2): isopropyl 2-{(2R,4aR,5S,6S,7aS)-5-[(2,3-dihydro-1H-inden-5-yloxy)methyl]-6-hydroxyoctahydrocyclopenta[b]pyran-2-yl}-1,3-thiazole-4-carboxylate (Compound 11-2)

TLC: Rf 0.57 (hexane:ethyl acetate=1:1);
$^1$H-NMR (CDCl$_3$): δ 1.38, 1.50-1.70, 1.96-2.33, 2.41-2.55, 2.79-2.92, 4.12, 4.35, 4.64, 5.10, 5.26, 6.70, 6.81, 7.11, 8.11.

Example 11 (3): isopropyl 2-{(2R,4aR,5S,6S,7aS)-5-[(3-cyclopropyl-4-ethylphenoxy)methyl]-6-hydroxyoctahydrocyclopenta[b]pyran-2-yl}-1,3-thiazole-4-carboxylate (Compound 11-3)

TLC: Rf 0.51 (hexane:ethyl acetate, 1:1);
$^1$H-NMR (CDCl$_3$): δ 0.65, 0.94, 1.23, 1.37, 1.52, 1.89-1.98, 1.99-2.07, 2.14-2.44, 2.46, 2.76, 4.10, 4.35, 4.64, 5.10, 5.26, 6.52, 6.69, 7.06, 8.11.

Example 11 (4): isopropyl 2-{(2R,4aR,5S,6S,7aS)-6-hydroxy-5-[(6,7,8,9-tetrahydro-5H-benzo[7]annulen-2-yloxy)methyl]octahydrocyclopenta[b]pyran-2-yl}-1,3-thiazole-4-carboxylate (Compound 11-4)

TLC: Rf 0.35 (hexane:ethyl acetate=2:1);
$^1$H-NMR (CDCl$_3$): δ 1.38, 1.50-1.64, 1.81, 1.96-2.08, 2.18, 2.25, 2.48, 2.74, 4.13, 4.35, 4.64, 5.11, 5.27, 6.64, 6.71, 7.00, 8.13.

Example 11 (5): isopropyl 2-{(2R,4aR,5S,6S,7aS)-5-[(3-cyclobutyl-4-ethylphenoxy)methyl]-6-hydroxyoctahydrocyclopenta[b]pyran-2-yl}-1,3-thiazole-4-carboxylate (Compound 11-5)

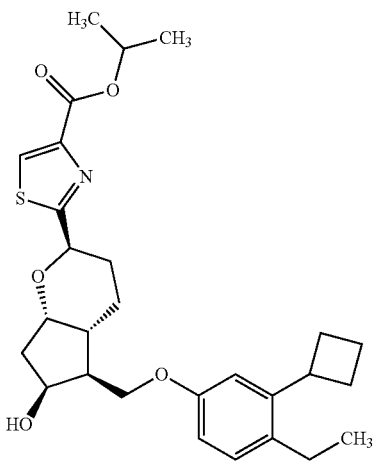 [SMILES: CCc1ccc(OC[C@@H]2[C@H]3CC[C@H](c4nc(C(=O)OC(C)C)cs4)O[C@H]3C[C@@H]2O)cc1C1CCC1]

TLC: Rf 0.58 (hexane:ethyl acetate=6:4);
$^1$H-NMR (CDCl$_3$): δ 1.17, 1.38, 1.50-1.62, 1.79-1.90, 1.95-2.39, 2.43-2.61, 3.67, 4.15, 4.37, 4.66, 5.11, 5.27, 6.72, 6.87, 7.06, 8.13.

Example 11 (6): isopropyl 2-{(2R,4aR,5S,6S,7aS)-5-[(3,4-dicyclopropylphenoxy)methyl]-6-hydroxyoctahydrocyclopenta[b]pyran-2-yl}-1,3-thiazole-4-carboxylate (Compound 11-6)

TLC: Rf 0.55 (hexane:ethyl acetate=6:4);
$^1$H-NMR (CDCl$_3$): δ 0.59-0.71, 0.88-1.01, 1.38, 1.49-1.62, 1.95-2.32, 2.41-2.51, 4.10, 4.35, 4.63, 5.10, 5.27, 6.52, 6.66, 6.91, 8.13.

Example 12: 2-{(2R,4aR,5S,6S,7aS)-5-[(3-cyclopropyl-4-ethylphenoxy)methyl]-6-hydroxyoctahydrocyclopenta[b]pyran-2-yl}-N-ethyl-1,3-thiazole-4-carboxamide (Compound 12)

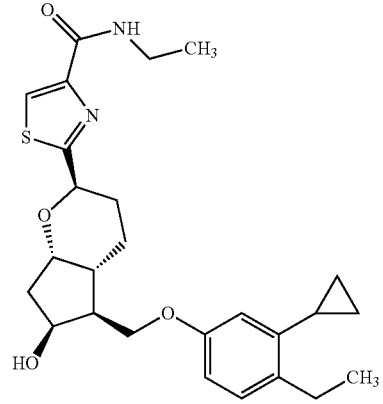 [SMILES: CCNC(=O)c1csc([C@H]2CC[C@@H]3[C@@H](COc4ccc(CC)c(C5CC5)c4)[C@@H](O)C[C@@H]3O2)n1]

N,N-Dimethylformamide (0.5 mL), a 2 M ethylamine/tetrahydrofuran solution (112 μL), 1-ethyl-3-(3-dimethylaminopropyl)carbodiimide hydrochloride (43 mg), 1-hydroxybenzotriazole (30 mg) and triethylamine (94 μL) were added to compound 9 (35) (50 mg) under argon stream, and the mixed solution was stirred at room temperature for 20 hours. Subsequently, the resulting solution was stirred at 50° C. for 3 hours, and further stirred at 80° C. for 3 hours. A 1 M aqueous hydrochloric acid solution was added to the reaction solution, and the reaction solution was extracted with ethyl acetate. The organic layer was washed with water and saturated brine, then dried over anhydrous sodium sulfate, and then filtrated. The filtrate was concentrated under reduced pressure, and the residue was purified by silica gel column chromatography (hexane:ethyl acetate=1:1→0:100) to produce the title compound (29.6 mg) having the following properties.

TLC: Rf 0.67 (ethyl acetate);
$^1$H-NMR (CDCl$_3$): δ 0.95, 1.24, 1.26, 1.57-1.61, 1.91-2.10, 2.18, 2.20, 2.50, 2.76, 4.11, 4.31, 4.65, 5.07, 6.53, 6.70, 7.08, 7.26, 8.10.

Reference Example 24: methyl 2-[(2R,4aR,5S,6S,7aS)-5-({[tert-butyl(diphenyl)silyl]oxy}methyl)-6-hydroxyoctahydrocyclopenta[b]pyran-2-yl]-1,3-thiazole-4-carboxylate (Reference compound 24)

The same procedures as in Example C→Example D→Example C were carried out except that Reference compound 8 was used in place of compound B, thereby producing the title compound having the following physical property value.

TLC: Rf 0.39 (hexane:ethyl acetate=2:1).

Reference Example 25: methyl 2-[(2R,4aR,5S,6R,7aS)-5-({[tert-butyl(diphenyl)silyl]oxy}methyl)-6-methoxyoctahydrocyclopenta[b]pyran-2-yl]-1,3-thiazole-4-carboxylate (Reference compound 25)

Acetonitrile (2.0 mL), silver oxide (336 mg) and iodomethane (90 µL) were added to Reference compound 24 (400 mg) under argon stream, and the mixed solution was stirred at room temperature overnight. The reaction solution was filtrated through Celite (trade name), and then the filtrate was concentrated under reduced pressure. The residue was purified by silica gel column chromatography (hexane:ethyl acetate=95:5→0:100) to produce the title compound (89.5 mg) having the following physical property value.

TLC: Rf 0.53 (hexane:ethyl acetate=2:1).

Examples 13 (1) to (6)

The same procedure as in Example 5 was carried out except that Reference compound 25 was used in place of Reference compound 14, thereby producing a compound. Subsequently, the same procedures as in Example A→Example 9 were carried out except that the resulting compound was used in place of Reference compound 9 and, in place of 3,5-difluorophenol, a corresponding substituted phenol was used. In this manner, the following compounds were produced.

Example 13 (1): 2-{(2R,4aR,5S,6S,7aS)-5-[(4-chloro-3-methylphenoxy)methyl]-6-methoxyoctahydrocyclopenta[b]pyran-2-yl}-1,3-thiazole-4-carboxylic acid (Compound 13-1)

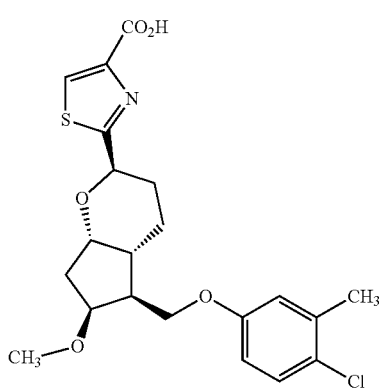

TLC: Rf 0.61 (chloroform:methanol:acetic acid=9:1:0.1);
$^1$H-NMR (CDCl$_3$): δ 1.59, 1.93-2.08, 2.17, 2.30, 2.34, 2.47, 3.25, 3.90, 3.99, 4.17, 4.27, 5.09, 6.69, 6.79, 7.21, 8.27.

Example 13 (2): 2-{(2R,4aR,5S,6S,7aS)-5-[(4-ethyl-3-methylphenoxy)methyl]-6-methoxyoctahydrocyclopenta[b]pyran-2-yl}-1,3-thiazole-4-carboxylic acid (Compound 13-2)

TLC: Rf 0.67 (dichloromethane:methanol=4:1);
$^1$H-NMR (CDCl$_3$): δ 1.18, 1.64, 1.90-2.06, 2.17, 2.28, 2.47, 2.56, 3.26, 3.91, 4.00, 4.17, 4.27, 5.08, 6.70, 6.72, 7.04, 8.25.

Example 13 (3): 2-{(2R,4aR,5S,6S,7aS)-5-[(3-ethyl-4-methylphenoxy)methyl]-6-methoxyoctahydrocyclopenta[b]pyran-2-yl}-1,3-thiazole-4-carboxylic acid (Compound 13-3)

TLC: Rf 0.67 (dichloromethane:methanol=4:1);
$^1$H-NMR (CDCl$_3$): δ 1.21, 1.62, 1.88-2.06, 2.16, 2.23, 2.29, 2.48, 2.59, 3.27, 3.91, 4.00, 4.18, 4.27, 5.08, 6.66, 6.74, 7.03, 8.25.

Example 13 (4): 2-{(2R,4aR,5S,6S,7aS)-6-methoxy-5-[(4-methyl-3-propylphenoxy)methyl]octahydrocyclopenta[b]pyran-2-yl})-1,3-thiazole-4-carboxylic acid (Compound 13-4)

TLC: Rf 0.63 (dichloromethane:methanol=4:1);
$^1$H-NMR (CDCl$_3$): δ 0.99, 1.63, 1.90-2.04, 2.13-2.23, 2.23, 2.54, 3.26, 3.91, 4.00, 4.17, 4.26, 5.08, 6.66, 6.71, 7.02, 8.25.

Example 13 (5): 2-{(2R,4aR,5S,6S,7aS)-5-[(3,4-dichlorophenoxy)methyl]-6-methoxyoctahydrocyclopenta[b]pyran-2-yl}-1,3-thiazole-4-carboxylic acid (Compound 13-5)

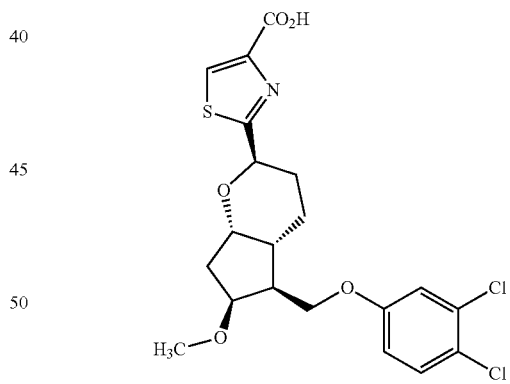

TLC: Rf 0.53 (chloroform:methanol:acetic acid=90:10:1);
$^1$H-NMR (CDCl$_3$): δ 1.57-1.64, 1.90-2.39, 2.41-2.54, 3.25, 3.91, 3.99, 4.17, 4.27, 5.09, 6.77, 7.01, 7.31, 8.26.

Example 13 (6): 2-[(2R,4aR,5S,6S,7aS)-6-methoxy-5-{[4-methyl-3-(methylthio)phenoxy]methyl}octahydrocyclopenta[b]pyran-2-yl]-1,3-thiazole-4-carboxylic acid (Compound 13-6)

TLC: Rf 0.52 (chloroform:methanol:acetic acid=90:10:1);

¹H-NMR (CDCl₃): δ 1.57-1.64, 1.90-2.10, 2.12-2.23, 2.26, 2.26-2.59, 2.41-2.53, 2.46, 3.26, 3.93, 4.01, 4.19, 4.28, 5.09, 6.62, 6.72, 7.02, 8.27.

Examples 14 (1) to (6)

The same procedure as in Example 5 was carried out except that Reference compound 25 was used in place of Reference compound 14, thereby producing a compound. Subsequently, the same procedures as in Example A→Example 10 were carried out except that the resulting compound was used in place of Reference compound 9 and, in place of 3,5-difluorophenol, a corresponding substituted phenol was used. In this manner, the following compounds were produced.

Example 14 (1): (2-{(2R,4aR,5S,6S,7aS)-5-[(4-chloro-3-methylphenoxy)methyl]-6-methoxyoctahydrocyclopenta[b]pyran-2-yl}-1,3-thiazol-4-yl)methanol (Compound 14-1)

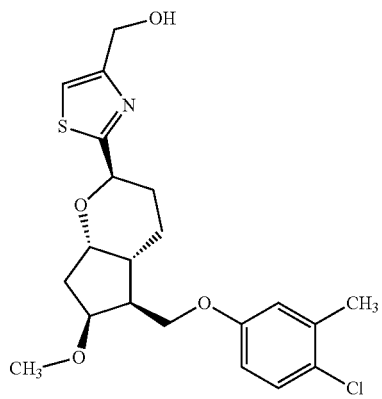

TLC: Rf 0.52 (ethyl acetate);
¹H-NMR (CDCl₃): δ 1.61, 1.91-2.10, 2.15, 2.26, 2.34, 2.49, 3.25, 3.89, 4.00, 4.16, 4.29, 4.76, 5.07, 6.68, 6.78, 7.16, 7.20.

Example 14 (2): (2-{(2R,4aR,5S,6S,7aS)-5-[(4-ethyl-3-methylphenoxy)methyl]-6-methoxyoctahydrocyclopenta[b]pyran-2-yl}-1,3-thiazol-4-yl)methanol (Compound 14-2)

TLC: Rf 0.52 (hexane:ethyl acetate=1:2);
¹H-NMR (CDCl₃): δ 1.18, 1.64, 1.90-2.06, 2.10-2.24, 2.28, 2.49, 2.56, 3.26, 3.90, 4.00, 4.17, 4.29, 4.75, 5.07, 6.70, 6.72, 7.04, 7.16.

Example 14 (3): (2-{(2R,4aR,5S,6S,7aS)-5-[(3-ethyl-4-methylphenoxy)methyl]-6-methoxyoctahydrocyclopenta[b]pyran-2-yl}-1,3-thiazol-4-yl)methanol (Compound 14-3)

TLC: Rf 0.52 (hexane:ethyl acetate=1:2);
¹H-NMR (CDCl₃): δ 1.21, 1.64, 1.91-2.06, 2.10-2.19, 2.23, 2.49, 2.59, 3.26, 3.91, 4.01, 4.18, 4.30, 4.75, 5.07, 6.66, 6.74, 7.02, 7.16.

Example 14 (4): (2-f{(2R,4aR,5S,6S,7aS)-6-methoxy-5-[(4-methyl-3-propylphenoxy)methyl]octahydrocyclopenta[b]pyran-2-yl}-1,3-thiazol-4-yl)methanol (Compound 14-4)

TLC: Rf 0.38 (hexane:ethyl acetate=1:1);
¹H-NMR (CDCl₃): δ 0.99, 1.64, 1.92-2.06, 2.10-2.22, 2.26, 2.46, 2.54, 3.26, 3.91, 4.01, 4.17, 4.28, 4.75, 5.06, 6.66, 6.71, 7.01, 7.16.

Example 14 (5): (2-{(2R,4aR,5S,6S,7aS)-5-[(3,4-dichlorophenoxy)methyl]-6-methoxyoctahydrocyclopenta[b]pyran-2-yl}-1,3-thiazol-4-yl)methanol (Compound 14-5)

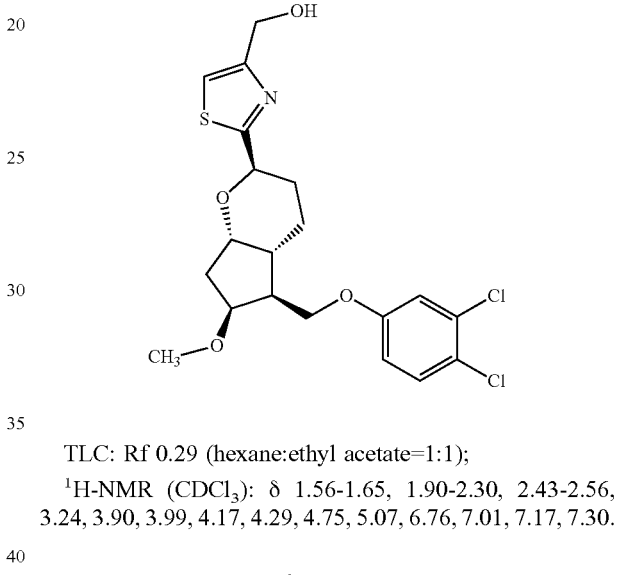

TLC: Rf 0.29 (hexane:ethyl acetate=1:1);
¹H-NMR (CDCl₃): δ 1.56-1.65, 1.90-2.30, 2.43-2.56, 3.24, 3.90, 3.99, 4.17, 4.29, 4.75, 5.07, 6.76, 7.01, 7.17, 7.30.

Example 14 (6): {2-[(2R,4aR,5S,6S,7aS)-6-methoxy-5-{[4-methyl-3-(methylthio)phenoxy]methyl}octahydrocyclopenta[b]pyran-2-yl]-1,3-thiazol-4-yl}methanol (Compound 14-6)

TLC: Rf 0.31 (hexane:ethyl acetate=1:1);
¹H-NMR (CDCl₃): δ 1.57-1.64, 1.90-2.21, 2.26, 2.44-2.55, 3.26, 3.92, 4.01, 4.19, 4.30, 4.75, 5.07, 6.62, 6.73, 7.02, 7.16.

Examples 15 (1) to (2)

The same procedures as in Reference example 12→Example C→Example D→Example C→Reference example 17→Example 5→Reference example 19 were carried out except that Reference compound 9 was used in place of Reference compound 11, thereby producing a compound. Subsequently, the same procedures as in Reference example 20→Example 7→Example 9 were carried out except that the resulting compound was used in place of Reference compound 19 and 4-chloro-3-methylaniline or 4-ethyl-3-methylaniline was used in place of 5-aminoindane. In this manner, the following compounds were produced.

Example 15 (1): 2-[(2R,4aR,5S,6S,7aS)-5-{[(4-chloro-3-methylphenyl)amino]methyl}-6-hydroxyoctahydrocyclopenta[b]pyran-2-yl]-1,3-thiazole-4-carboxylic acid (Compound 15-1)

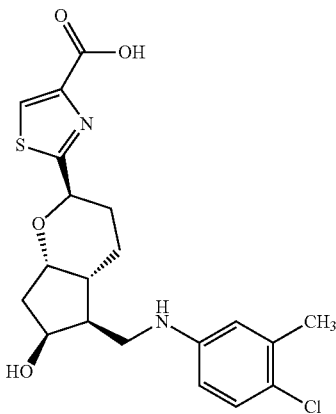 [SMILES: Cc1cc(NC[C@@H]2[C@H]3CC[C@H](c4nc(C(=O)O)cs4)O[C@H]3C[C@@H]2O)ccc1Cl]

TLC: Rf 0.34 (dichloromethane:methanol=10:1) COOH Silica plate;
$^1$H-NMR (CDCl$_3$): δ 1.50-2.42, 3.21, 3.34, 4.27, 4.59, 5.07, 6.67, 6.75, 7.18, 8.27.

Example 15 (2): 2-[(2R,4aR,5S,6S,7aS)-5-{[(4-ethyl-3-methylphenyl)amino]methyl}-6-hydroxyoctahydrocyclopenta[b]pyran-2-yl]-1,3-thiazole-4-carboxylic acid (Compound 15-2)

TLC: Rf 0.32 (chloroform:methanol:acetic acid=90:10:1);
$^1$H-NMR (DMSO-d$_6$): δ 1.06, 1.40-1.55, 1.73-1.99, 2.00-2.20, 2.14, 2.41, 2.99, 3.11, 4.13-4.24, 4.51, 5.04, 6.31-6.40, 6.82, 8.42.

Example 16: (2R,4aR,5S,6S,7aS)-5-{[(4-chloro-3-methylphenyl)amino]methyl}-2-[4-(hydroxymethyl)-1,3-thiazol-2-yl]octahydrocyclopenta[b]pyran-6-ol (Compound 16)

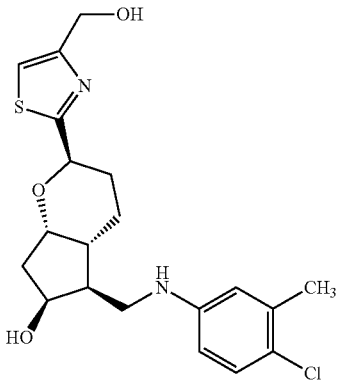 [SMILES: Cc1cc(NC[C@@H]2[C@H]3CC[C@H](c4nc(CO)cs4)O[C@H]3C[C@@H]2O)ccc1Cl]

The same procedures as in Reference example 12→Example C→Example D→Example C→Reference example 17→Example 5→Reference example 19 were carried out except that Reference compound 9 was used in place of Reference compound 11, thereby producing a compound. The same procedures as in Reference example 20→Example 7→Example 10 were carried out except that the resulting compound was used in place of Reference compound 19 and 4-chloro-3-methylaniline was used in place of 5-aminoindane, thereby producing the title compound having the following physical property values.
TLC: Rf 0.57 (ethyl acetate);
$^1$H-NMR (CDCl$_3$): δ 1.89-2.01, 2.04-2.20, 3.19, 3.27, 4.32, 4.55, 4.75, 5.07, 6.45, 6.57, 7.12, 7.18.

Reference Example 26: ethyl 5-[(2R,4aR,5S,6R,7aS)-6-(acetyloxy)-5-({[tert-butyl(diphenyl)silyl]oxy}methyl)octahydrocyclopenta[b]pyran-2-yl]furan-2-carboxylate (Reference compound 26)

Acetonitrile (10 mL) was added to Reference compound 5 (510 mg) under argon stream, and the mixed solution was stirred at 0° C. for 5 minutes. A 5-ethoxycarbonyl-2-furanyl zinc bromide/0.5 M tetrahydrofuran solution (4.0 mL) was added to the resulting solution and then stirred at 0° C. for 5 minutes. Subsequently, aluminum chloride (266 mg) was added to the resulting solution, and then stirred at 0° C. for 1 hour and further stirred at room temperature for 30 minutes. Water and a 1 M aqueous hydrochloric acid solution were added to the reaction solution, and the reaction solution was extracted with ethyl acetate, then dried over anhydrous magnesium sulfate, and then filtrated. The filtrate was concentrated under reduced pressure, and the residue was purified by silica gel column chromatography (hexane:ethyl acetate=9:1→2:1) to produce the title compound (300 mg) having the following physical property value.
TLC: Rf 0.36 (hexane:ethyl acetate=4:1).

Example 17: 5-{(2R,4aR,5S,6R,7aS)-5-[(4-chloro-3-methylphenoxy)methyl]-6-hydroxyoctahydrocyclopenta[b]pyran-2-yl}-2-furoic acid (Compound 17)

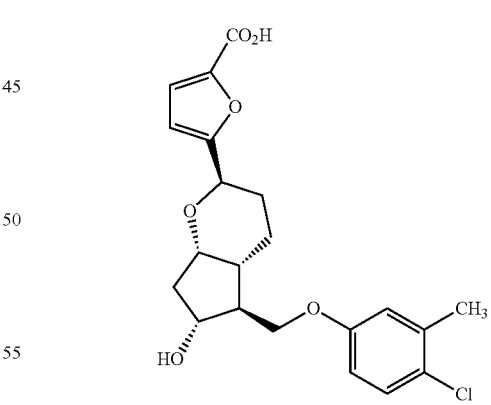

The same procedure as in Reference example 9 was carried out except that Reference compound 26 was used in place of Reference compound 8, thereby producing a compound. Subsequently, the same procedures as in Example A→Example 9 were carried out except that the resulting compound was used in place of Reference compound 9 and 4-chloro-3-methylphenol was used in place of 3,5-difluorophenol, thereby producing the title compound having the following physical property values.

TLC: Rf 0.17 (dichloromethane:methanol:water=80:20:1);

$^1$H-NMR (DMSO-d$_6$): δ 1.55-1.82, 1.91-2.21, 2.28, 3.79-4.01, 4.08, 4.80-4.91, 6.57, 6.78, 6.94, 7.14, 7.26.

Example 17 (1): 2-{(2R,4aR,5S,6R,7aS)-5-[(4-chloro-3-methylphenoxy)methyl]-6-hydroxyoctahydrocyclopenta[b]pyran-2-yl}-1,3-oxazole-4-carboxylic acid (Compound 17-1)

The same procedures as in Reference example 26→Example 17 were carried out except that, in place of 5-ethoxycarbonyl-2-furanyl zinc bromide, a corresponding oxazole derivative was used, thereby producing the title compound having the following physical property values.

TLC: Rf 0.12 (dichloromethane:methanol=4:1);

$^1$H-NMR (CDCl$_3$): δ 1.75, 1.87, 1.95, 2.05-2.20, 2.33, 2.46, 3.92, 4.02, 4.09, 4.16, 5.12, 6.65, 6.76, 7.20, 8.34.

Example 18: (2R,4aR,5S,6R,7aS)-5-[(4-chloro-3-methylphenoxy)methyl]-2-[5-(hydroxymethyl)-2-furyl]octahydrocyclopenta[b]pyran-6-ol (Compound 18)

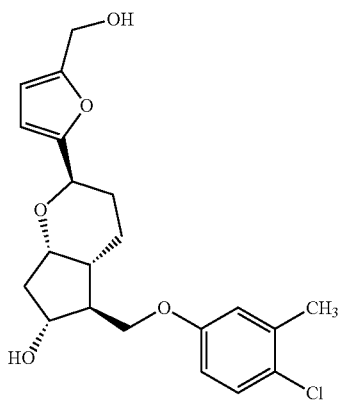 [SMILES: Cc1cc(OC[C@@H]2[C@H]3CC[C@H](c4ccc(CO)o4)O[C@H]3C[C@H]2O)ccc1Cl]

The same procedure as in Reference example 9 was carried out except that Reference compound 26 was used in place of Reference compound 8, thereby producing a compound. Subsequently, the same procedures as in Example A→Example 2 were carried out except that the resulting compound was used in place of Reference compound 9 and 4-chloro-3-methylphenol was used in place of 3,5-difluorophenol, thereby producing the title compound having the following physical property values.

TLC: Rf 0.27 (hexane:ethyl acetate=20:80);

$^1$H-NMR (DMSO-d$_6$): δ 1.65-1.89, 1.90-2.19, 2.33, 2.39-2.48, 2.85, 3.91, 4.00, 4.04-4.16, 4.61, 4.99, 6.23-6.27, 6.65, 6.76, 7.20.

Example 18 (1): (2R,4aR,5S,6R,7aS)-5-[(4-chloro-3-methylphenoxy)methyl]-2-[4-(hydroxymethyl)-1,3-oxazol-2-yl]octahydrocyclopenta[b]pyran-6-ol (Compound 18-1)

The same procedures as in Reference example 26→Example 18 were carried out except that, in place of 5-ethoxycarbonyl-2-furanyl zinc bromide, a corresponding oxazole derivative was used, thereby producing the title compound having the following physical property values.

TLC: Rf 0.58 (ethyl acetate);

$^1$H-NMR (CDCl$_3$): δ 1.75, 1.83, 1.97, 2.05, 2.11-2.21, 2.34, 2.46, 2.70, 3.92, 4.03, 4.14, 4.62, 5.06, 6.65, 6.76, 7.20, 7.61.

Example 19: isopropyl 5-{(2R,4aR,5S,6R,7aS)-5-[(4-chloro-3-methylphenoxy)methyl]-6-hydroxyoctahydrocyclopenta[b]pyran-2-yl}-2-furoate (Compound 19)

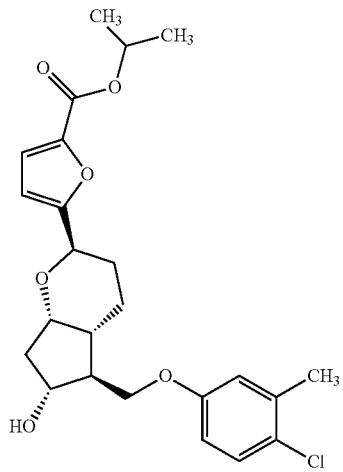 [SMILES: Cc1cc(OC[C@@H]2[C@H]3CC[C@H](c4ccc(C(=O)OC(C)C)o4)O[C@H]3C[C@H]2O)ccc1Cl]

The same procedure as in Reference example 9 was carried out except that Reference compound 26 was used in place of Reference compound 8, thereby producing a compound. Subsequently, the same procedures as in Example A→Example 9→Example 3 were carried out except that the resulting compound was used in place of Reference compound 9 and 4-chloro-3-methylphenol was used in place of 3,5-difluorophenol, thereby producing the title compound having the following physical property values.

TLC: Rf 0.38 (hexane:ethyl acetate=1:1);

$^1$H-NMR (CDCl$_3$): δ 1.34, 1.72, 1.84, 1.93, 2.00-2.23, 2.33, 2.79, 3.91, 4.00, 4.12, 5.05, 5.21, 6.41, 6.65, 6.76, 7.11, 7.20.

Example 20: 5-{(2R,4aR,5S,6S,7aS)-5-[(4-chloro-3-methylphenoxy)methyl]-6-hydroxyoctahydrocyclopenta[b]pyran-2-yl}-2-furoic acid (Compound 20)

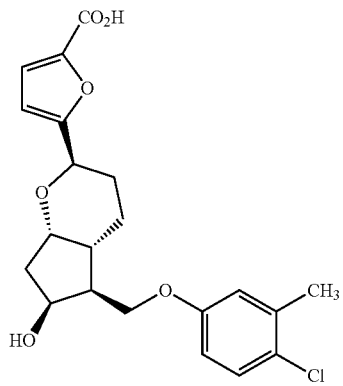 [SMILES: Cc1cc(OC[C@@H]2[C@H]3CC[C@H](c4ccc(C(=O)O)o4)O[C@H]3C[C@@H]2O)ccc1Cl]

The same procedures as in Example C→Example D→Example C→Reference example 17→Example 5 were carried out except that Reference compound 26 was used in place of compound B, thereby producing a compound. Subsequently, the same procedures as in Example A→Example 7→Example 9 were carried out except that the resulting compound was used in place of Reference compound 9 and 4-chloro-3-methylphenol was used in place of 3,5-difluorophenol, thereby producing the title compound having the following physical property values.

TLC: Rf 0.15 (hexane:ethyl acetate=1:2);

$^1$H-NMR (CDCl$_3$): δ 1.53-1.65, 1.86-2.21, 2.34, 2.45-2.58, 4.03-4.18, 4.22, 4.62, 4.97, 6.44, 6.69, 6.80, 7.21, 7.27.

Examples 20 (1) to (3)

The same procedure as in Reference example 26 was carried out except that 5-ethoxycarbonyl-2-furanyl zinc bromide or a corresponding furan or oxazole derivative was used, thereby producing a compound. The same procedures as in Example C→Example D→Example C→Reference example 17→Example 5 were carried out except that the resulting compound was used, thereby producing a compound. The same procedures as in Example A→Example 7→Example 9 were carried out except that the resulting compound was used in place of Reference compound 9 and, in place of 3,5-difluorophenol, a corresponding substituted phenol was used. In this manner, the following compounds were produced.

Example 20 (1): 5-{(2R,4aR,5S,6S,7aS)-5-[(4-ethyl-3-methylphenoxy)methyl]-6-hydroxyoctahydrocyclopenta[b]pyran-2-yl}-2-furoic acid (Compound 20-1)

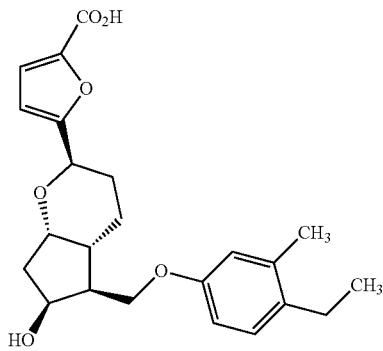 [SMILES: CCc1ccc(OC[C@@H]2[C@H]3CC[C@H](c4ccc(C(=O)O)o4)O[C@H]3C[C@@H]2O)cc1C]

TLC: Rf 0.15 (hexane:ethyl acetate=1:2);

$^1$H-NMR (CDCl$_3$): δ 1.20, 1.53-1.65, 1.86-2.21, 2.23, 2.45-2.63, 4.13, 4.22, 4.63, 4.97, 6.44, 6.67, 6.76, 7.04, 7.28.

Example 20 (2): 2-{(2R,4aR,5S,6S,7aS)-5-[(3-ethyl-4-methylphenoxy)methyl]-6-hydroxyoctahydrocyclopenta[b]pyran-2-yl}-1,3-oxazole-4-carboxylic acid (Compound 20-2)

TLC: Rf 0.19 (hexane:ethyl acetate=1:3);

$^1$H-NMR (CDCl$_3$): δ 1.20, 1.59-1.68, 1.87-1.98, 2.03-2.24, 2.49-2.63, 4.10-4.18, 4.64, 5.01, 6.67, 6.74, 7.03, 8.33.

Example 20 (3): 4-{(2R,4aR,5S,6S,7aS)-5-[(4-chloro-3-methylphenoxy)methyl]-6-hydroxyoctahydrocyclopenta[b]pyran-2-yl}-2-furoic acid (Compound 20-3)

TLC: Rf 0.49 (chloroform:methanol:acetic acid=90:10:1);

$^1$H-NMR (CDCl$_3$): δ 1.46-1.77, 1.86-2.21, 2.34, 2.45-2.61, 4.03-4.18, 4.64, 4.89, 6.69, 6.79, 7.21, 7.28, 7.53.

Example 21: (2R,4aR,5S,6S,7aS)-5-[(4-chloro-3-methylphenoxy)methyl]-2-[5-(hydroxymethyl)-2-furyl]octahydrocyclopenta[b]pyran-6-ol (Compound 21)

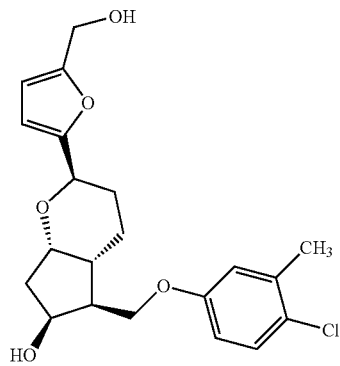 [SMILES: Cc1cc(OC[C@@H]2[C@H]3CC[C@H](c4ccc(CO)o4)O[C@H]3C[C@@H]2O)ccc1Cl]

The same procedures as in Example C→Example D→Example C→Reference example 17→Example 5 were carried out except that Reference compound 26 was used in place of compound B, thereby producing a compound. The same procedures as in Example A→Example 7→Example 2 were carried out except that the resulting compound was used in place of Reference compound 9 and 4-chloro-3-methylphenol was used in place of 3,5-difluorophenol, thereby producing the title compound having the following physical property values.

TLC: Rf 0.20 (hexane:ethyl acetate=1:2);

$^1$H-NMR (CDCl$_3$): δ 1.53-1.65, 1.84-2.20, 2.34, 2.45-2.58, 4.03-4.20, 4.22, 4.57-4.68, 4.89, 6.19-6.26, 6.70, 6.80, 7.22.

Examples 21 (1) to (3)

The same procedure as in Reference example 26 was carried out except that 5-ethoxycarbonyl-2-furanyl zinc bromide or a corresponding furan or oxazole derivative was used, thereby producing a compound. The same procedures as in Example C→Example D→Example C→Reference example 17→Example 5 were carried out except that the resulting compound was used. The same procedures as in Example A→Example 7→Example 2 were carried out except that, in place of 3,5-difluorophenol, a corresponding substituted phenol was used. In this manner, the following compounds were produced.

Example 21 (1): (2R,4aR,5S,6S,7aS)-5-[(4-ethyl-3-methylphenoxy)methyl]-2-[5-(hydroxymethyl)-2-furyl]octahydrocyclopenta[b]pyran-6-ol (Compound 21-1)

TLC: Rf 0.22 (hexane:ethyl acetate=1:2);
$^1$H-NMR (CDCl$_3$): δ 1.18, 1.53-1.65, 1.79-2.19, 2.28, 2.45-2.63, 4.13, 4.53-4.68, 4.89, 6.22-6.28, 6.67-6.75, 7.05.

Example 21 (2): (2R,4aR,5S,6S,7aS)-5-[(3-ethyl-4-methylphenoxy)methyl]-2-[4-(hydroxymethyl)-1,3-oxazol-2-yl]octahydrocyclopenta[b]pyran-6-ol (Compound 21-2)

$^1$H-NMR (CDCl$_3$): δ 1.21, 1.57-1.67, 1.86-1.97, 2.00-2.21, 2.23, 2.50-2.63, 4.13, 4.19, 4.60-4.70, 4.97, 6.67, 6.74, 7.04, 7.61.

Example 21 (3): (2R,4aR,5S,6S,7aS)-5-[(4-chloro-3-methylphenoxy)methyl]-2-[5-(hydroxymethyl)-3-furyl]octahydrocyclopenta[b]pyran-6-ol (Compound 21-3)

TLC: Rf 0.13 (hexane:ethyl acetate=1:1);
$^1$H-NMR (CDCl$_3$): δ 1.63-1.78, 1.81-2.19, 2.34, 2.47-2.61, 4.01-4.19, 4.57-4.68, 4.83, 6.31, 6.69, 6.79, 7.21, 7.29.

Reference Example 27: (2R,4aR,5S,6R,7aS)-5-({[tert-butyl(diphenyl)silyl]oxy}methyl)-6-hydroxyoctahydrocyclopenta[b]pyran-2-carbonitrile (Reference compound 27)

The same procedure as in Example C was carried out except that Reference compound 6 was used in place of compound B, thereby producing the title compound having the following physical property value.
TLC: Rf 0.28 (hexane:ethyl acetate=7:3).

Reference Example 28: (2R,4aR,5S,6R,7aS)-5-({[tert-butyl(diphenyl)silyl]oxy}methyl)-2-cyanooctahydrocyclopenta[b]pyran-6-yl benzoate (Reference compound 28)

Pyridine (10 mL) and benzoyl chloride (0.47 mL) were added to Reference compound 27 (1.47 g) under argon stream, and the mixed solution was stirred at room temperature for 1 hour. A 1 M aqueous hydrochloric acid solution was added to the reaction solution, and the reaction solution was extracted with ethyl acetate. The organic layer was washed with a saturated aqueous sodium hydrogen carbonate solution and saturated brine, then dried over anhydrous sodium sulfate, and then filtrated. The filtrate was concentrated under reduced pressure, and the residue was purified by silica gel column chromatography (hexane:ethyl acetate=100:0→85:15) to produce the title compound (1.68 g) having the following physical property value.
TLC: Rf 0.64 (hexane:ethyl acetate=7:3).

Reference Example 29: (2R,4aR,5S,6R,7aS)-5-({[tert-butyl(diphenyl)silyl]oxy}methyl)-2-cyano-2-methyloctahydrocyclopenta[b]pyran-6-yl benzoate (Reference compound 29)

Tetrahydrofuran (6.64 mL), N,N'-dimethylpropyleneurea (1.66 mL) and iodomethane (1.03 mL) were added to Reference compound 28 (892 mg) under argon stream, and the mixed solution was stirred at −40° C. for 10 minutes. 2 M Lithium diisopropylamide/tetrahydrofuran (1.98 mL) was added dropwise to the resulting solution slowly, and the resulting solution was stirred at −40° C. for 1 hour. A saturated aqueous ammonium chloride solution was added to the reaction solution, and the reaction solution was extracted with ethyl acetate. The organic layer was washed with a saturated aqueous sodium hydrogen carbonate solution and saturated brine, then dried over anhydrous magnesium sulfate, and then filtrated. The filtrate was concentrated under reduced pressure, and the residue was purified by silica gel column chromatography (hexane:ethyl acetate=100:0→85:15) to produce the title compound (293 mg) having the following physical property value.
TLC: Rf 0.29 (hexane:ethyl acetate=9:1).

Example 22: 2-{(2R,4aR,5S,6R,7aS)-5-[(4-chloro-3-cyclopropylphenoxy)methyl]-6-hydroxy-2-methyl-octahydrocyclopenta[b]pyran-2-yl}-1,3-thiazole-4-carboxylic acid (Compound 22)

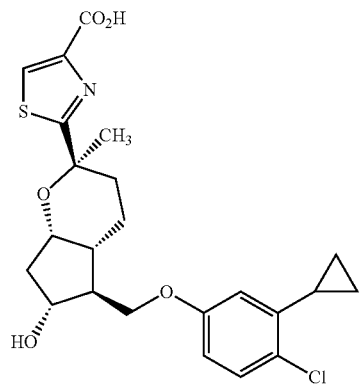 [SMILES: C[C@]1(c2nc(C(=O)O)cs2)CC[C@@H]2[C@@H](COc3ccc(Cl)c(C4CC4)c3)[C@H](O)C[C@@H]2O1]

The same procedures as in Reference example 7→Reference example 8→Example 5 were carried out except that Reference compound 29 was used in place of Reference compound 6, thereby producing a compound. The same procedures as in Example A→Example C→Example 9 were carried out except that the resulting compound was used in place of Reference compound 9 and 4-chloro-3-cyclopropylphenol was used in place of 3,5-difluorophenol, thereby producing the title compound having the following physical property values.
TLC: Rf 0.55 (chloroform:methanol:acetic acid=90:10:1);
$^1$H-NMR (CDCl$_3$): δ 0.66, 1.00, 1.56, 1.67-1.81, 1.90-2.20, 2.40-2.49, 2.50-2.59, 3.87, 3.99, 4.08-4.19, 4.22, 6.43, 6.61, 7.21, 8.29.

Examples 22 (1) to (3)

The same procedure as in Example 22 was carried out except that, in place of 4-chloro-3-cyclopropylphenol, a corresponding substituted phenol was used. In this manner, the following compounds were produced.
201

Example 22 (1): 2-{(2R,4aR,5S,6R,7aS)-5-[(4-ethyl-3-methylphenoxy)methyl]-6-hydroxy-2-methyloctahydrocyclopenta[b]pyran-2-yl}-1,3-thiazole-4-carboxylic acid (Compound 22-1)

TLC: Rf 0.55 (chloroform:methanol:acetic acid=90:10:1);

¹H-NMR (CDCl₃): δ 1.17, 1.56, 1.69-1.83, 1.90-2.15, 2.26, 2.40-2.60, 3.90, 4.03, 4.12, 4.17, 6.62-6.69, 7.03, 8.29.

Example 22 (2): 2-[(2R,4aR,5S,6R,7aS)-6-hydroxy-2-methyl-5-{[4-methyl-3-(methylthio)phenoxy]methyl}octahydrocyclopenta[b]pyran-2-yl]-1,3-thiazole-4-carboxylic acid (Compound 22-2)

TLC: Rf 0.46 (dichloromethane:methanol:acetic acid=10:1:0.1);

¹H-NMR (CDCl₃): δ 1.56, 1.69-1.83, 1.90-2.15, 2.24, 2.40-2.60, 3.91, 4.04, 4.12, 4.19, 6.56, 6.68, 7.02, 8.30.

Example 22 (3): 2-{(2R,4aR,5S,6R,7aS)-5-[(3-cyclopropyl-4-ethylphenoxy)methyl]-6-hydroxy-2-methyloctahydrocyclopenta[b]pyran-2-yl}-1,3-thiazole-4-carboxylic acid (Compound 22-3)

TLC: Rf 0.53 (chloroform:methanol:acetic acid=90:10:1);

¹H-NMR (CDCl₃): δ 0.60-0.68, 0.88-0.97, 1.22, 1.56, 1.68-1.82, 1.85-2.15, 2.40-2.60, 2.75, 3.89, 4.02, 4.12, 4.17, 6.48, 6.65, 7.05, 8.30.

Examples 23 (1) to (2)

The same procedures as in Reference example 7→Reference example 8→Example 5 were carried out except that Reference compound 29 was used in place of Reference compound 6, thereby producing a compound. The same procedures as in Example A→Example C→Example 10 were carried out except that the resulting compound was used in place of Reference compound 9 and 4-methyl-3-thiomethylphenol or 3-cyclopropyl-4-ethyl phenol was used in place of 3,5-difluorophenol. In this manner, the following compounds were produced.

Example 23 (1): (2R,4aR,5S,6R,7aS)-2-[4-(hydroxymethyl)-1,3-thiazol-2-yl]-2-methyl-5-{[4-methyl-3-(methylthio)phenoxy]methyl}octahydrocyclopenta[b]pyran-6-ol (Compound 23-1)

TLC: Rf 0.15 (hexane:ethyl acetate=2:8);

¹H-NMR (CDCl₃): δ 1.54, 1.68-1.78, 1.90-2.05, 2.19, 2.24, 2.44, 2.44-2.50, 2.94, 3.89, 4.02, 4.11-4.22, 4.75, 6.56, 6.68, 7.01, 7.18.

Example 23 (2): (2R,4aR,5S,6R,7aS)-5-[(3-cyclopropyl-4-ethylphenoxy)methyl]-2-[4-(hydroxymethyl)-1,3-thiazol-2-yl]-2-methyloctahydrocyclopenta[b]pyran-6-ol (Compound 23-2)

TLC: Rf 0.40 (hexane:ethyl acetate=3:7);

¹H-NMR (CDCl₃): δ 0.60-0.67, 0.88-0.96, 1.22, 1.53, 1.65-1.78, 1.85-2.10, 2.23-2.32, 2.40-2.49, 2.75, 2.95, 3.87, 4.00, 4.10-4.21, 4.75, 6.48, 6.65, 7.05, 7.18.

Example 24: 2-[(2R,4aR,5S,6S,7aS)-5-{[4-ethyl-3-(methylamino)phenoxy]methyl}-6-hydroxy-2-methyloctahydrocyclopenta[b]pyran-2-yl]-1,3-thiazole-4-carboxylic acid (Compound 24)

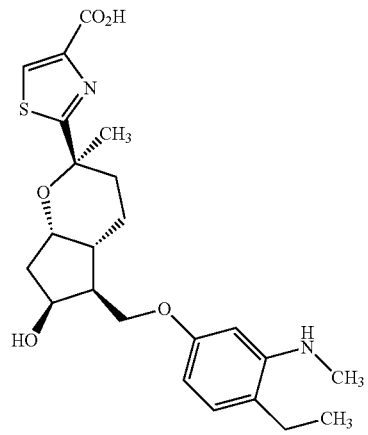 [SMILES: CCc1ccc(OC[C@@H]2[C@H]3CC[C@](C)(c4nc(C(=O)O)cs4)O[C@H]3C[C@@H]2O)cc1NC]

The same procedures as in Reference example 7→Reference example 8→Example 5 were carried out except that Reference compound 29 was used in place of Reference compound 6, thereby producing a compound. The same procedures as in Example A→Example C→Example D→Example 9 were carried out except that the resulting compound was used in place of Reference compound 9 and 4-ethyl-3-methylaminophenol was used in place of 3,5-difluorophenol, thereby producing the title compound having the following physical property values.

TLC: Rf 0.59 (chloroform:methanol:acetic acid=90:10:1);

¹H-NMR (CDCl₃): δ 1.21, 1.50, 1.56-1.69, 1.81-2.04, 2.22, 2.33-2.58, 2.87, 4.09-4.18, 4.68, 6.20, 6.27, 6.96, 8.26.

Examples 24 (1) to (4)

The same procedure as in Reference example 29 was carried out except that iodomethane or iodoethane was used, thereby producing a compound. The same procedure as in Example 24 was carried out except that the resulting compound was used in place of Reference compound 29 and 4-ethyl-3-methylaminophenol or a corresponding substituted phenol was used. In this manner, the following compounds were produced.

Example 24 (1): 2-[(2R,4aR,5S,6S,7aS)-2-ethyl-5-{[4-ethyl-3-(methylamino)phenoxy]methyl}-6-hydroxyoctahydrocyclopenta[b]pyran-2-yl]-1,3-thiazole-4-carboxylic acid (Compound 24-1)

TLC: Rf 0.32 (dichloromethane:methanol=4:1);

¹H-NMR (CDCl₃): δ 0.76, 1.21, 1.28, 1.59, 1.78, 1.85-1.97, 2.24, 2.34, 2.38, 2.53, 2.87, 4.10-4.13, 4.68, 6.19, 6.26, 6.95, 8.27.

Example 24 (2): 2-[(2R,4aR,5S,6S,7aS)-6-hydroxy-2-methyl-5-{[4-methyl-3-(methylthio)phenoxy]methyl}octahydrocyclopenta[b]pyran-2-yl]-1,3-thiazole-4-carboxylic acid (Compound 24-2)

TLC: Rf 0.41 (dichloromethane:methanol:acetic acid=10:1:0.1);

$^1$H-NMR (CDCl$_3$): δ 1.51, 1.62, 1.93-1.99, 2.20, 2.26, 2.39-2.46, 2.46, 2.52, 4.08-4.18, 4.68, 6.62, 6.72, 7.04, 8.27.

Example 24 (3): 2-{(2R,4aR,5S,6S,7aS)-5-[(3,4-dicyclopropylphenoxy)methyl]-6-hydroxy-2-methyloctahydrocyclopenta[b]pyran-2-yl}-1,3-thiazole-4-carboxylic acid (Compound 24-3)

TLC: Rf 0.53 (dichloromethane:methanol:acetic acid=10:1:0.1);
$^1$H-NMR (CDCl$_3$): δ 0.62, 0.66, 0.91, 0.97, 1.50, 1.51-1.67, 1.82-2.02, 2.03-2.12, 2.14-2.28, 2.35-2.57, 3.49, 4.08, 4.13, 4.66, 6.50, 6.65, 6.91, 8.26.

Example 24 (4): 2-{(2R,4aR,5S,6S,7aS)-5-[(3-cyclopropyl-4-ethylphenoxy)methyl]-6-hydroxy-2-methyloctahydrocyclopenta[b]pyran-2-yl}-1,3-thiazole-4-carboxylic acid (Compound 24-4)

TLC: Rf 0.29 (chloroform:methanol:acetic acid=90:10:1);
$^1$H-NMR (CDCl$_3$): δ 0.62-0.69, 0.90-0.98, 1.24, 1.50, 1.57-1.68, 1.88-2.06, 2.22, 2.37-2.57, 2.77, 4.06-4.17, 4.67, 6.53, 6.71, 7.08, 8.29.

Example 25: (2R,4aR,5S,6S,7aS)-5-{[4-ethyl-3-(methylamino)phenoxy]methyl}-2-[4-(hydroxymethyl)-1,3-thiazol-2-yl]-2-methyloctahydrocyclopenta[b]pyran-6-ol (Compound 25)

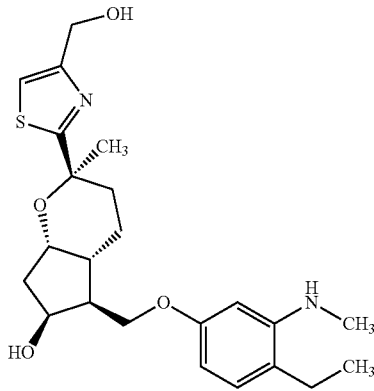 [SMILES: CCc1ccc(OC[C@@H]2[C@H]3CC[C@](C)(c4nc(CO)cs4)O[C@H]3C[C@@H]2O)cc1NC]

The same procedures as in Reference example 7→Reference example 8→Example 5 were carried out except that Reference compound 29 was used in place of Reference compound 6, thereby producing a compound. The same procedures as in Example A→Example C→Example D→Example 10 were carried out except that the resulting compound was used in place of Reference compound 9 and 4-ethyl-3-methylaminophenol was used in place of 3,5-difluorophenol, thereby producing the title compound having the following physical property values.
TLC: Rf 0.58 (hexane:ethyl acetate=1:9);
$^1$H-NMR (CDCl$_3$): δ 1.21, 1.48, 1.56-1.69, 1.83-1.99, 2.05-2.28, 2.30-2.47, 2.48-2.61, 2.87, 4.13, 4.19, 4.69, 4.75, 6.20, 6.27, 6.96, 7.16.

Examples 25 (1) to (4)

The same procedure as in Reference example 29 was carried out except that iodomethane or iodoethane was used, thereby producing a compound. The same procedure as in Example 25 was carried out except that the resulting compound was used in place of Reference compound 29 and 4-ethyl-3-methylaminophenol or a corresponding substituted phenol was used. In this manner, the title compounds having the following physical property values were produced.

Example 25 (1): (2R,4aR,5S,6S,7aS)-2-ethyl-5-{[4-ethyl-3-(methylamino)phenoxy]methyl}-2-[4-(hydroxymethyl)-1,3-thiazol-2-yl]octahydrocyclopenta[b]pyran-6-ol (Compound 25-1)

TLC: Rf 0.42 (ethyl acetate);
$^1$H-NMR (CDCl$_3$): δ 0.78, 1.21, 1.28, 1.58-1.64, 1.76, 1.85-1.93, 2.11, 2.20, 2.26-2.33, 2.41, 2.52, 2.87, 4.11, 4.20, 4.68, 4.75, 6.19, 6.26, 6.95, 7.16.

Example 25 (2): (2R,4aR,5S,6S,7aS)-2-[4-(hydroxymethyl)-1,3-thiazol-2-yl]-2-methyl-5-{[4-methyl-3-(methylthio)phenoxy]methyl}octahydrocyclopenta[b]pyran-6-ol (Compound 25-2)

TLC: Rf 0.17 (hexane:ethyl acetate=2:8);
$^1$H-NMR (CDCl$_3$): δ 1.48, 1.62, 1.87-1.98, 2.21, 2.26, 2.31-2.40, 2.46, 2.53, 4.08-4.13, 4.19, 4.68, 4.74, 6.62, 6.72, 7.03, 7.15.

Example 25 (3): (2R,4aR,5S,6S,7aS)-5-[(3-cyclopropyl-4-ethylphenoxy)methyl]-2-[4-(hydroxymethyl)-1,3-thiazol-2-yl]-2-methyloctahydrocyclopenta[b]pyran-6-ol (Compound 25-3)

TLC: Rf 0.45 (hexane:ethyl acetate=1:4);
$^1$H-NMR (CDCl$_3$): δ 0.65, 0.94, 1.23, 1.55, 1.61, 1.86-1.97, 2.01, 2.15, 2.20, 2.35, 2.52, 2.77, 4.09, 4.19, 4.67, 4.75, 6.53, 6.71, 7.08, 7.17.

Example 25 (4): (2R,4aR,5S,6S,7aS)-5-[(3-cyclopropyl-4-propylphenoxy)methyl]-2-[4-(hydroxymethyl)-1,3-thiazol-2-yl]-2-methyloctahydrocyclopenta[b]pyran-6-ol (Compound 25-4)

TLC: Rf 0.49 (hexane:ethyl acetate=3:7);
$^1$H-NMR (CDCl$_3$): δ 0.60-0.67, 0.90-1.02, 1.47, 1.50-1.70, 1.80-2.02, 2.18-2.30, 2.52, 2.70, 4.03-4.15, 4.19, 4.67, 4.75, 6.51, 6.69, 7.05, 7.17.

Pharmacological Experimental Example

In Vitro Test
(1) Measurement of Agonist Activity on Various Prostanoid Receptors
Using Chem1 cells or CHO cells in which various prostanoid receptors were forcibly expressed, respectively, agonist activities of test compounds on various prostanoid receptors was determined employing, as a measure, an intracellular cyclic AMP (hereinbelow, abbreviated as "cAMP") production amount or an intracellular calcium concentration.
<Compound Treatment>
The test compound and a control substance (PGE$_2$ and PGF$_{2\alpha}$) were dissolved in dimethyl sulfoxide (DMSO) to prepare a 10 mmol/L solution. The 10 mmol/L solution thus prepared was thawed upon use, then serially diluted with DMSO, and then diluted with a buffer solution for measurement use or a buffer solution for measurement use 2, and then the resulting solution was subjected to an experiment.
<Cell Culturing>

Cells forcibly expressing various prostanoid receptors were standing-cultured at 37° C. in the presence of 5% $CO_2$ using a DMEM medium (Sigma) (for culturing FP-Chem1) containing inactivated (56° C., 30 minutes) 9.8 vol % nondialysed-FBS (Life Technologies), 1 vol % Non Essential Amino Acids (Life Technologies), 10 mmol/L HEPES Buffer Solution (Life Technologies), 0.5 vol % GENETICIN (Life Technologies) and 1% penicillin-streptomycin (Life Technologies) or an α-MEM medium (Sigma) (for culturing EP2-CHO) containing inactivated (56° C., 30 minutes) 9.8 vol % dialysed-FBS (Life Technologies) and penicillin-streptomycin-glutamine (Life Technologies). Subculturing was carried out by the following manner.

The medium was removed, and washed with a phosphate-buffered physiological saline not containing $Ca^{2+}$ and $Mg^{2+}$ one time. A proper amount of trypsin-EDTA (Life Technologies) was added, and this was incubated at room temperature, cells were peeled, and a medium having a volume which is 10-fold a volume of trypsin-EDTA was added to stop an enzymatic reaction. After cells were recovered into a centrifuging tube, and centrifuged at room temperature for 3 minutes at 120 g, the supernatant was removed. Cells were suspended in a proper amount of a medium, and seeded in a culturing flask.

(1-1) Measurement of EP2 Agonist Activity (Measurement of cAMP Concentration)

On the measurement day, a medium was removed, and EP2-CHO was washed with a phosphate-buffered physiological saline containing 2 mmol/L EDTA and not containing $Ca^{2+}$ and $Mg^{2+}$ one time. A proper amount of the phosphate-buffered physiological saline containing 2 mmol/L EDTA and not containing $Ca^{2+}$ and $Mg^{2+}$ was added, this was incubated at 37° C. in the presence of 5% $CO_2$, cells were peeled, cells were recovered into a centrifuging tube, and centrifuged at room temperature for 3 minutes at 550 g, and the supernatant was removed. Cells were suspended in a proper amount of a buffer solution for measurement 1 (MEM medium (Invitrogen) containing 1.0 w/v % bovine serum albumin (Sigma) and 2 µmol/L diclofenac (Sigma)), and centrifuged at room temperature for 3 minutes at 200 g, and the supernatant was removed. Cells were suspended in a buffer solution for measurement 2 (MEM medium (Invitrogen) containing 1.0 w/v % bovine serum albumin (Sigma), 2 µmol/L diclofenac (Sigma) and 1 mmol/L 3-isobutyl-1-methylxanthine), and each 25 µL of the suspension was dispensed into a 96-well ½ area plate so that the cell number per well became $1.25 \times 10^6$. A buffer solution for measurement 2 (25 µL) containing an agonist at a variety of concentrations was added to carry out a reaction at room temperature for 30 minutes. Measurement of a cAMP concentration was carried out using the cAMP HTRF HiRange kit (CIS bio International). According to the two step protocol of the kit manual, each 25 µL of cAMP-D2 and Cryptase diluted with a lysis buffer were added, and this was incubated at room temperature for 1 hour. After incubation for 1 hour, time resolution fluorescence at 620 nm and 660 nm when excited at 340 nm was measured using SpectraMax M5e (Molecular Device), and a ratio (TRF ratio) was obtained, thereby, a cAMP concentration was calculated from a calibration line.

(1-2) Measurement of FP Agonist Activity (Measurement of Intracellular Calcium Concentration)

Regarding FP-Chem1, by the same method as that of subculturing, cells were peeled and suspended and, before two days from measurement, the suspension was seeded on a 96-well UV plate so that the cell number per well became $0.5 \times 10^4$, and standing-cultured at 37° C. in the presence of 5% $CO_2$. On the measurement day, after the medium was removed from each well of the 96-well UV plate, each well was washed with a phosphate-buffered physiological saline not containing $Ca^{2+}$ and $Mg^{2+}$ one time. To each well was added 120 µL of a buffer solution for measurement (Hank's balanced salt solution (Invitrogen) containing 0.1 w/v % bovine serum albumin, 2.8 µmol/L diclofenac, 1.25 mmol/L Probenecid and 20 mmol/L HEPES (Invitrogen)) containing FLIPR Calcium 5 Assay Kit (Molecular Devices), and this was incubated at room temperature for about 60 minutes under light-shielding conditions, which was subjected to an experiment.

The 96-well UV plate was set in a fluorescent spectral photometer (FDSS-7000EX, Hamamatsu Photonics K.K.), and an intracellular calcium concentration was measured. A buffered solution for measurement (30 µL) containing an agonist at a variety of concentrations was added to carry out a reaction. Measurement of an intracellular calcium concentration was carried out by irradiating cells with excited light having a wavelength of 485 nm, and measuring a fluorescent intensity at 525 nm.

<Results>

Using the measurement values obtained by the above-mentioned method, an $EC_{50}$ value was calculated as an index for agonist activity of the compound according to the present invention on human EP2 and a human FP receptor.

The results are shown in the following tables.

TABLE 1

| Ex. | 1(4) | 1(5) | 1(6) | 1(7) | 1(12) | 1(13) | 1(15) | 1(16) |
|---|---|---|---|---|---|---|---|---|
| EP2 agonist activity EC50 (nM) | 0.50 | 0.90 | 7.5 | 3.3 | 19 | 1.1 | 14 | 5.5 |

| Ex. | 1(17) | 1(19) | 1(22) | 1(27) | 9 | 9(1) | 9(3) | 9(4) |
|---|---|---|---|---|---|---|---|---|
| EP2 agonist activity EC50 (nM) | 0.82 | 2.4 | 2.3 | 12 | 2.8 | 0.86 | 0.16 | 0.33 |

| Ex. | 9(5) | 9(12) | 9(23) | 9(25) | 9(33) | 9(35) | 9(36) |
|---|---|---|---|---|---|---|---|
| EP2 agonist activity EC50 (nM) | 0.91 | 6.4 | 1.6 | 0.074 | 1.6 | 2.4 | 3.5 |

As shown above, the compounds according to the present invention exerted potent EP2 agonist activities. Any of the compounds had an FP agonist activity (an $EC_{50}$ value) of 10 µM or more.

On the other hand, compounds having an analogous structure to that of the compound according to the present invention, i.e., the following compound which is disclosed in International Publication No. 2011/013651 pamphlet:

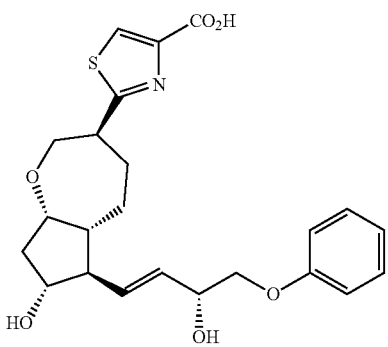 [SMILES: O=C(O)c1csc([C@H]2CC[C@@H]3[C@@H](/C=C/[C@@H](O)COc4ccccc4)[C@H](O)C[C@@H]3OC2)n1]

the following compound which is disclosed in Japanese Patent Laying-Open No. S61-218588:

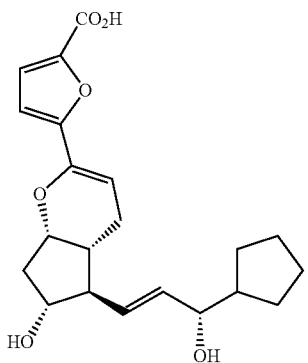 [SMILES: O=C(O)c1ccc(C2=CC[C@@H]3[C@@H](/C=C/[C@@H](O)C4CCCC4)[C@H](O)C[C@@H]3O2)o1]

and the following compound which is disclosed in Japanese Patent Laying-Open No. S55-89261:

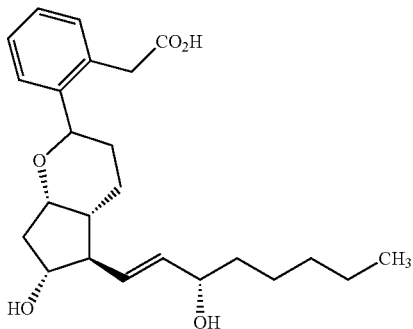

were also determined on their EP2 agonist activities. All of the compounds had $EC_{50}$ values of 10 μM or more, which were extremely poor compared with those of the compounds according to the present application.

In Vivo Test

As can be easily understood by a person skilled in the art, in an in vivo test, since regarding all test compounds, carboxylic acid which is an active body has poor corneal permeability, pharmacological action of the active body was evaluated by ocular instillation administration of a compound which had been converted into an ester such as an ethyl ester or an isopropyl ester, or an alcohol.

(2) Intraocular Pressure Lowering Activity

A test compound-containing solution (30 μL) which had been adjusted to each of various concentrations was ocular instillation-administered to the left or right eye of a male monkey (a cynomolgus monkey) under consciousness. An intraocular pressure after administration was measured with time from administration initiation to after 24 hours. Upon measurement of an intraocular pressure, a cynomolgus monkey was fixed on a monkey chair, and the monkey was anesthetized by ocular instillation-administering an ocular surface anesthetic (Benoxil eye drops 0.4% Santen Pharmaceutical Co., Ltd.). After mounting of a blepharostat (Handaya Co., Ltd.), an intraocular pressure of both eyes was measured (7 to 8 examples per group) using a pneumatic applanation flat tonometer (Model 30 Classic, REICHERT). A difference between an intraocular pressure value before the administration of a test substance and an intraocular pressure value after the administration of the test substance was calculated as an intraocular pressure lowering rate in accordance with the following equation, and the sustainability of intraocular eye lowering action was evaluated using a maximum intraocular pressure lowering rate during measurement.

$$\text{Intraocular pressure lowering rate}(\%) = \frac{\begin{pmatrix}\text{intraocular pressure value before}\\\text{administration of test substance}\end{pmatrix} - \begin{pmatrix}\text{intraocular pressure value after}\\\text{administration of test substance}\end{pmatrix}}{\begin{pmatrix}\text{intraocular pressure value before}\\\text{administration of test substance}\end{pmatrix}} \times 100$$

[Equation 1]

<Results>

The results are shown in the following tables. The administered concentrations were determined based on the EP2 agonist activities measured by the above-mentioned method.

TABLE 2

| Ex. | 2(4) | 2(5) | 2(7) | 2(8) | 2(9) | 2(10) | 2(12) | 2(13) |
|---|---|---|---|---|---|---|---|---|
| Administration concentration (μg/mL) | 100 | 30 | 30 | 30 | 10 | 10 | 10 | 3 |
| Intraocular pressure lowering rate (%) | 40 | 48 | 38 | 55 | 52 | 31 | 43 | 31 |
| Ex. | 2(14) | 2(16) | 3(1) | 3(3) | 3(4) | 10 | 10(1) | 10(3) |
| Administration concentration (μg/mL) | 30 | 30 | 100 | 3 | 30 | 10 | 3 | 1 |
| Intraocular pressure | 45 | 51 | 28 | 33 | 35 | 40 | 29 | 49 |

TABLE 2-continued

| lowering rate (%) | | | | | | | | |
|---|---|---|---|---|---|---|---|---|
| Ex. | 10(7) | 10(12) | 10(15) | 10(16) | 10(17) | 10(21) | 10(22) | 10(32) |
| Administration concentration (μg/mL) | 10 | 0.3 | 3 | 10 | 100 | 1 | 3 | 3 |
| Intraocular pressure lowering rate (%) | 41 | 33 | 37 | 45 | 57 | 44 | 43 | 41 |

As shown above, the compounds according to the present invention exerted a potent intraocular pressure lowering action. Therefore, it was demonstrated that the compounds according to the present invention are effective on an ocular disease which is one type of EP2 receptor-related diseases.

Preparation Examples

Representative preparation examples used in the present invention will be shown below.

1. Injections

Compound 1 (200 g), mannitol (20 g) and distilled water (50 L) were mixed by an ordinary method, the resulting solution was sterilized by an ordinary method and then filled in ampules at a volume of 5 mL per ampule. The ampules were lyophilized by an ordinary method. In this manner, 10,000 ampules each containing 20 mg of active ingredients were produced.

2. Tablets

Compound 2 (50 g), calcium carboxymethyl cellulose (20 g), magnesium stearate (10 g) and crystalline cellulose (920 g) were mixed by an ordinary method, and the resulting mixture was tableted. In this manner, 10,000 tablets each containing 5 mg of active ingredients were produced.

3. Eye Drops

Glycerin (2.5 g) and Polysorbate 80 (500 mg) were added to sterilized purified water, compound 3 (1 mg) was added to dissolve, sterile purified water was added to a total amount of 100 mL, and this was sterile-filtered with a membrane filter, and filled into a predetermined container. In this manner, eye drops were produced.

INDUSTRIAL APPLICABILITY

The compound according to the present invention has a selective EP2 agonist activity and is highly safe, and is therefore useful as a therapeutic agent for EP2 receptor-related diseases, including immune diseases, allergic diseases, neuronal death, dysmenorrhea, premature birth, miscarriage, baldness, ocular diseases, erectile dysfunction, arthritis, lung injury, pulmonary fibrosis, pulmonary emphysema, bronchitis, chronic obstructive pulmonary disease, liver injury, acute hepatitis, cirrhosis, shock, nephritis, renal failure, cardiovascular diseases, systemic inflammatory response syndrome, sepsis, hemophagocytic syndrome, macrophage activation syndrome, Still's disease, Kawasaki disease, burn injury, systemic granuromatous disease, colitis ulcerosa, Crohn's disease, hypercytokinemia on dialysis, multiple organ failure, bone diseases, cartilage injury and others.

The invention claimed is:

1. A compound represented by general formula (I-1):

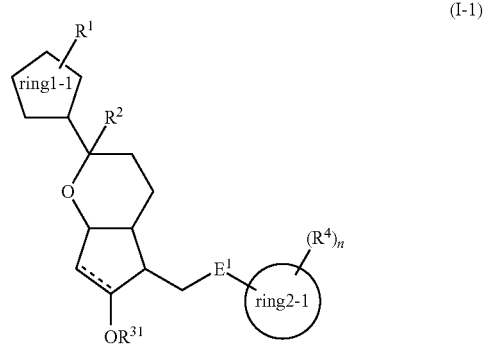

(I-1)

wherein ring 1-1 represents a 5-membered monocyclic aromatic heterocyclic ring;

$R^1$ represents —$(CH_2)_p$—COOH, —$(CH_2)_q$—COOR$^{11}$, —$(CH_2)_r$—OH, —$(CH_2)_s$—OR$^{12}$, —$CH_2NR^{13}R^{14}$ or —$CONR^{13}R^{14}$, p represents an integer of 0 or 1 to 4,
q represents an integer of 0 or 1 to 4,
r represents an integer of 1 to 4,
s represents an integer of 1 to 4,
$R^{11}$ represents a $C_{1-4}$ alkyl group,
$R^{12}$ represents a $C_{1-4}$ alkyl group or a $C_{1-4}$ acyl group,
$R^{13}$ represents a hydrogen atom or a $C_{1-4}$ alkyl group,
$R^{14}$ represents a hydrogen atom, a $C_{1-4}$ alkyl group, a $C_{1-4}$ acyl group or a $R^{15}O(C=O)$—$C_{1-4}$ alkyl group,
or $R^{13}$ and $R^{14}$ together with a nitrogen atom to which $R^{13}$ and $R^{14}$ are bonded represents a saturated 5 to 8-membered cyclic amine,
$R^{15}$ represents a hydrogen atom or a $C_{1-4}$ alkyl group;
$R^2$ represents a hydrogen atom or a $C_{1-4}$ alkyl group;
$R^{31}$ represents a hydrogen atom, a $C_{1-4}$ alkyl group or a $C_{1-4}$ acyl group;
$E^1$ represents —O—, —S— or —NH—;
ring 2-1 represents a benzene ring or a 8- to 15-membered benzene condensed ring which is bound to $E^1$ through a benzene ring;
$R^4$ represents (1) a $C_{1-8}$ alkyl group, (2) a $C_{2-8}$ alkenyl group, (3) a $C_{2-8}$ alkynyl group, (4) a $C_{3-8}$ cycloalkyl group, (5) a $C_{1-8}$ alkoxy group, (6) a $C_{3-8}$ cycloalkyloxy group, (7) a $C_{1-8}$ acyl group, (8) a $C_{1-8}$ acyloxy group, (9) a $C_{1-8}$ alkylthio group, (10) a $C_{3-8}$ cycloalkylthio group, (11) a $C_{1-8}$ alkylsulfinyl group, (12) a $C_{3-8}$ cycloalkylsulfinyl group, (13) a $C_{1-8}$ alkylsulfonyl group, (14) a $C_{3-8}$ cycloalkylsulfonyl group, (15) a $C_{1-8}$ alkoxycarbonyl group, (16) a 5- or 6-membered cyclic group, (17) a (5- or 6-membered cyclic group)-$C_{1-4}$ alkyl group, (18) a (5- or 6-membered cyclic group)-$C_{1-4}$ alkoxy group, (19) a (5- or 6-membered cyclic group)-$C_{1-4}$ acyl group, (20) a halogen atom, (21) a hydroxy group, (22) a nitro group, (23) a cyano group, (24) —$NR^{16}R^{17}$, (25) —$CONR^{18}R^{19}$ or (26) —$SO_2NR^{20}R^{21}$, $R^{16}$, $R^{17}$, $R^{18}$, $R^{19}$, $R^{20}$ and $R^{21}$ each independently represent a hydrogen atom, a $C_{1-8}$ alkyl group, a $C_{1-8}$ acyl group or a $C_{1-8}$ alkylsulfonyl group, n represents an integer of 0 or 1 to 5, wherein multiple $R^4$'s may be the same as or different from each other when n is 2 or more, and each of groups (1) to (19) among the groups for $R^4$ may be substituted with one to three $R^5$'s, $R^5$ represents a $C_{1-4}$ alkyl group, a $C_{1-4}$ alkoxy group, a $C_{1-4}$ acyl group, a $C_{3-8}$ cycloalkyl group, —OH, —$NR^{22}R^{23}$ or a halogen atom, wherein multiple $R^5$'s may be the same as or different from each other when each of groups (1) to (19) is substituted with the multiple R5's, $R^{22}$ and $R^{23}$ each independently represent a hydrogen atom or a $C_{1-4}$ alkyl group;

~~~~ represents a single bond or a double bond; and a single bond,

⁓, attached to an asymmetric carbon represents an α-configuration, a β-configuration or a mixture thereof in an arbitrary ratio, a salt or N-oxide of the compound, or a solvate or prodrug of the compound or the salt or N-oxide.

2. The compound according to claim 1, wherein ring 1-1 represents oxazole, thiazole, furan or thiophene.

3. The compound according to claim 1, wherein the compound is (1) 2-{(2R,4aR,5S,6R,7aS)-6-hydroxy-5-[(3-methyl-4-nitrophenoxy)methyl]octahydrocyclopenta[b]pyran-2-yl}-1,3-thiazole-4-carboxylic acid, (2) 2-{(2R,4aR,5S,6R,7aS)-5-[(4-chloro-3-methylphenoxy)methyl]-6-hydroxyoctahydrocyclopenta[b]pyran-2-yl}-1,3-thiazole-4-carboxylic acid, (3) 2-{(2R,4aR,5S,6R,7aS)-5-[(2,3-dihydro-1H-inden-5-yloxy)methyl]-6-hydroxyoctahydrocyclopenta[b]pyran-2-yl}-1,3-thiazole-4-carboxylic acid, (4) 2-{(2R,4aR,5S,6R,7aS)-5-[(3,4-dimethylphenoxy)methyl]-6-hydroxyoctahydrocyclopenta[b]pyran-2-yl}-1,3-thiazole-4-carboxylic acid, (5) 2-{(2R,4aR,5S,6R,7aS)-6-hydroxy-5-[(1H-indol-5-yloxy)methyl]octahydrocyclopenta[b]pyran-2-yl}-1,3-thiazole-4-carboxylic acid, (6) 2-{(2R,4aR,5S,6R,7aS)-5-[(2,3-dihydro-1H-inden-4-yloxy)methyl]-6-hydroxyoctahydrocyclopenta[b]pyran-2-yl}-1,3-thiazole-4-carboxylic acid, (7) 2-{(2R,4aR,5S,6R,7aS)-5-[(bicyclo[4.2.0]octa-1,3,5-trien-3-yloxy)methyl]-6-hydroxyoctahydrocyclopenta[b]pyran-2-yl}-1,3-thiazole-4-carboxylic acid, (8) 2-{(2R,4aR,5S,6R,7aS)-5-[(1-benzofuran-6-yloxy)methyl]-6-hydroxyoctahydrocyclopenta[b]pyran-2-yl}-1,3-thiazole-4-carboxylic acid, (9) 2-{(2R,4aR,5S,6R,7aS)-5-[(3-ethyl-4-methylphenoxy)methyl]-6-hydroxyoctahydrocyclopenta[b]pyran-2-yl}-1,3-thiazole-4-carboxylic acid,

(10) 2-[(2R,4aR,5S,6R,7aS)-5-{[(4-fluoro-2,3-dihydro-1H-inden-5-yl)oxy]methyl}-6-hydroxyoctahydrocyclopenta[b]pyran-2-yl]-1,3-thiazole-4-carboxylic acid,

(11) 2-{(2R,4aR,5S,6R,7aS)-5-[(4-chloro-3-cyclopropylphenoxy)methyl]-6-hydroxyoctahydrocyclopenta[b]pyran-2-yl}-1,3-thiazole-4-carboxylic acid,

(12) 2-[(2R,4aR,5S,6R,7aS)-6-hydroxy-5-(phenoxymethyl)octahydrocyclopenta[b]pyran-2-yl]-1,3-thiazole-4-carboxylic acid,

(13) (2R,4aR,5S,6R,7aS)-5-[(2,3-dihydro-1H-inden-5-yloxy)methyl]-2-[4-(hydroxymethyl)-1,3-thiazol-2-yl]octahydrocyclopenta[b]pyran-6-ol,

(14) (2R,4aR,5S,6R,7aS)-2-[4-(hydroxymethyl)-1,3-thiazol-2-yl]-5-[(1H-indol-5-yloxy)methyl]octahydrocyclopenta[b]pyran-6-ol,

(15) (2R,4aR,5S,6R,7aS)-5-[(bicyclo[4.2.0]octa-1,3,5-trien-3-yloxy)methyl]-2-[4-(hydroxymethyl)-1,3-thiazol-2-yl]octahydrocyclopenta[b]pyran-6-ol,

(16) (2R,4aR,5S,6R,7aS)-5-[(1-benzofuran-6-yloxy)methyl]-2-[4-(hydroxymethyl)-1,3-thiazol-2-yl]octahydrocyclopenta[b]pyran-6-ol,

(17) (2R,4aR,5S,6R,7aS)-5-[(3-ethyl-4-methylphenoxy)methyl]-2-[4-(hydroxymethyl)-1,3-thiazol-2-yl]octahydrocyclopenta[b]pyran-6-ol,

(18) (2R,4aR,5S,6R,7aS)-5-[(4-chloro-3-cyclopropylphenoxy)methyl]-2-[4-(hydroxymethyl)-1,3-thiazol-2-yl]octahydrocyclopenta[b]pyran-6-ol,

(19) (2R,4aR,5S,6R,7aS)-5-[(3,4-dimethylphenoxy)methyl]-2-[4-(hydroxymethyl)-1,3-thiazol-2-yl]octahydrocyclopenta[b]pyran-6-ol,

(20) (2R,4aR,5S,6R,7aS)-5-[(4-chloro-3-methylphenoxy)methyl]-2-[4-(hydroxymethyl)-1,3-thiazol-2-yl]octahydrocyclopenta[b]pyran-6-ol,

(21) (2R,4aR,5S,6R,7aS)-5-[(2,3-dihydro-1H-inden-4-yloxy)methyl]-2-[4-(hydroxymethyl)-1,3-thiazol-2-yl]octahydrocyclopenta[b]pyran-6-ol,

(22) (2R,4aR,5S,6R,7aS)-5-{[(4-fluoro-2,3-dihydro-1H-inden-5-yl)oxy]methyl}-2-[4-(hydroxymethyl)-1,3-thiazol-2-yl]octahydrocyclopenta[b]pyran-6-ol,

(23) isopropyl 2-[(2R,4aR,5S,6R,7aS)-6-hydroxy-5-(phenoxymethyl)octahydrocyclopenta[b]pyran-2-yl]-1,3-thiazole-4-carboxylate,

(24) isopropyl 2-{(2R,4aR,5S,6R,7aS)-6-hydroxy-5-[(3-methyl-4-nitrophenoxy)methyl]octahydrocyclopenta[b]pyran-2-yl}-1,3-thiazole-4-carboxylate,

(25) isopropyl 2-{(2R,4aR,5S,6R,7aS)-5-[(2,3-dihydro-1H-inden-5-yloxy)methyl]-6-hydroxyoctahydrocyclopenta[b]pyran-2-yl}-1,3-thiazole-4-carboxylate,

(26) 2-{(2R,4aR,5S,6S,7aS)-5-[(3,4-dicyclopropylphenoxy)methyl]-6-hydroxyoctahydrocyclopenta[b]pyran-2-yl}-1,3-thiazole-4-carboxylic acid,

(27) 2-{(2R,4aR,5S,6S,7aS)-5-[(2,3-dihydro-1H-inden-5-yloxy)methyl]-6-hydroxyoctahydrocyclopenta[b]pyran-2-yl}-1,3-thiazole-4-carboxylic acid,

(28) 2-{(2R,4aR,5S,6S,7aS)-5-[(3-chloro-4-methylphenoxy)methyl]-6-hydroxyoctahydrocyclopenta[b]pyran-2-yl}-1,3-thiazole-4-carboxylic acid,

(29) 2-{(2R,4aR,5S,6S,7aS)-5-[(3-ethyl-4-methylphenoxy)methyl]-6-hydroxyoctahydrocyclopenta[b]pyran-2-yl}-1,3-thiazole-4-carboxylic acid,

(30) 2-[(2R,4aR,5S,6S,7aS)-5-{[(4-fluoro-2,3-dihydro-1H-inden-5-yl)oxy]methyl}-6-hydroxyoctahydrocyclopenta[b]pyran-2-yl]-1,3-thiazole-4-carboxylic acid,

(31) 2-{(2R,4aR,5S,6S,7aS)-6-hydroxy-5-[(5,6,7,8-tetrahydro-2-naphthalenyloxy)methyl]octahydrocyclopenta[b]pyran-2-yl}-1,3-thiazole-4-carboxylic acid,

(32) 2-{(2R,4aR,5S,6S,7aS)-5-[(3,4-diethylphenoxy)methyl]-6-hydroxyoctahydrocyclopenta[b]pyran-2-yl}-1,3-thiazole-4-carboxylic acid,

(33) 2-[(2R,4aR,5S,6S,7aS)-6-hydroxy-5-{[4-methyl-3-(methylthio)phenoxy]methyl}octahydrocyclopenta[b]pyran-2-yl]-1,3-thiazole-4-carboxylic acid,

(34) 2-{(2R,4aR,5S,6S,7aS)-6-hydroxy-5-[(6,7,8,9-tetrahydro-5H-benzo[7]annulen-2-yloxy)methyl]octahydrocyclopenta[b]pyran-2-yl}-1,3-thiazole-4-carboxylic acid,

(35) 2-{(2R,4aR,5S,6S,7aS)-5-[(3-cyclopropyl-4-ethylphenoxy)methyl]-6-hydroxyoctahydrocyclopenta[b]pyran-2-yl}-1,3-thiazole-4-carboxylic acid,

(36) 2-{(2R,4aR,5S,6S,7aS)-5-[(3-cyclobutyl-4-ethylphenoxy)methyl]-6-hydroxyoctahydrocyclopenta[b]pyran-2-yl}-1,3-thiazole-4-carboxylic acid,

(37) (2R,4aR,5S,6S,7aS)-5-[(3,4-dicyclopropylphenoxy)methyl]-2-[4-(hydroxymethyl)-1,3-thiazol-2-yl]octahydrocyclopenta[b]pyran-6-ol,

(38) (2R,4aR,5S,6S,7aS)-5-[(2,3-dihydro-1H-inden-5-yloxy)methyl]-2-[4-(hydroxymethyl)-1,3-thiazol-2-yl]octahydrocyclopenta[b]pyran-6-ol,

(39) (2R,4aR,5S,6S,7aS)-5-[(3-ethyl-4-methylphenoxy)methyl]-2-[4-(hydroxymethyl)-1,3-thiazol-2-yl]octahydrocyclopenta[b]pyran-6-ol,

(40) (2R,4aR,5S,6S,7aS)-2-[4-(hydroxymethyl)-1,3-thiazol-2-yl]-5-[(5,6,7,8-tetrahydro-2-naphthalenyloxy)methyl]octahydrocyclopenta[b]pyran-6-ol,

(41) (2R,4aR,5S,6S,7aS)-2-[4-(hydroxymethyl)-1,3-thiazol-2-yl]-5-{[4-methyl-3-(methylthio)phenoxy]methyl}octahydrocyclopenta[b]pyran-6-ol,

(42) (2R,4aR,5S,6S,7aS)-5-[(3-cyclopropyl-4-ethylphenoxy)methyl]-2-[4-(hydroxymethyl)-1,3-thiazol-2-yl]octahydrocyclopenta[b]pyran-6-ol,

(43) (2R,4aR,5S,6S,7aS)-2-[4-(hydroxymethyl)-1,3-thiazol-2-yl]-5-[(6,7,8,9-tetrahydro-5H-benzo[7]annulen-2-yloxy)methyl]octahydrocyclopenta[b]pyran-6-ol,

(44) (2R,4aR,5S,6S,7aS)-5-[(3-cyclobutyl-4-ethylphenoxy)methyl]-2-[4-(hydroxymethyl)-1,3-thiazol-2-yl]octahydrocyclopenta[b]pyran-6-ol,

(45) (2R,4aR,5S,6S,7aS)-5-[(3-chloro-4-methylphenoxy)methyl]-2-[4-(hydroxymethyl)-1,3-thiazol-2-yl]octahydrocyclopenta[b]pyran-6-ol,

(46) (2R,4aR,5S,6S,7aS)-5-{[(4-fluoro-2,3-dihydro-1H-inden-5-yl)oxy]methyl}-2-[4-(hydroxymethyl)-1,3-thiazol-2-yl]octahydrocyclopenta[b]pyran-6-ol or

(47) (2R,4aR,5S,6S,7aS)-5-[(3,4-diethylphenoxy)methyl]-2-[4-(hydroxymethyl)-1,3-thiazol-2-yl]octahydrocyclopenta[b]pyran-6-ol, a salt or N-oxide of the compound, or a solvate or prodrug of the compound or the salt or N-oxide.

4. A pharmaceutical composition comprising a compound represented by general formula (I-1) as defined in claim 1, a salt or N-oxide of the compound, or a solvate or prodrug of the compound or the salt or N-oxide.

5. A therapeutic agent for an EP2 receptor-related disease selected from the group consisting of immune diseases, allergic diseases, neuronal death, premature birth, baldness, ocular diseases, arthritis, lung injury, pulmonary fibrosis, pulmonary emphysema, chronic obstructive pulmonary disease, acute hepatitis, cirrhosis, nephritis, renal failure, cardiovascular diseases, sepsis, macrophage activation syndrome, bone diseases and cartilage injury, the agent comprising a compound represented by general formula (I-1) as defined in claim 1, a salt or N-oxide of the compound, or a solvate or prodrug of the compound or the salt or N-oxide.

6. A method for treating an EP2 receptor-related disease selected from the group consisting of immune diseases, allergic diseases, neuronal death, premature birth, baldness, ocular diseases, arthritis, lung injury, pulmonary fibrosis, pulmonary emphysema, chronic obstructive pulmonary disease, acute hepatitis, cirrhosis, nephritis, renal failure, cardiovascular diseases, sepsis, macrophage activation syndrome, bone diseases and cartilage injury, the method comprising administering an effective amount of a compound represented by general formula (I-1) as defined in claim 1, a salt or N-oxide of the compound, or a solvate or prodrug of the compound or the salt or N-oxide to a mammal.

7. 2-{(2R,4aR,5S,6S,7aS)-5-[(3-cyclopropyl-4-ethylphenoxy)methyl]-6-hydroxyoctahydrocyclopenta[b]pyran-2-yl}-1,3-thiazole-4-carboxylic acid, a salt or N-oxide of the compound, or a solvate or prodrug of the compound or the salt or N-oxide.

8. (2R,4aR,5S,6S,7aS)-5-[(3-cyclopropyl-4-ethylphenoxy)methyl]-2-[4-(hydroxymethyl)-1,3-thiazol-2-yl]octahydrocyclopenta[b]pyran-6-ol, a salt or N-oxide of the compound, or a solvate or prodrug of the compound or the salt or N-oxide.

* * * * *